United States Patent
Plant et al.

(10) Patent No.: US 7,465,805 B2
(45) Date of Patent: Dec. 16, 2008

(54) ISOXAZOLINE DERIVATIVES AND THEIR USE AS HERBICIDES

(75) Inventors: Andrew Plant, Bracknell (GB); Jutta Elisabeth Boehmer, Bracknell (GB); Alison Lindsey Peace, Bracknell (GB)

(73) Assignee: Syngenta Limited (GB)

( * ) Notice: Subject to any disclaimer, the term of this patent is extended or adjusted under 35 U.S.C. 154(b) by 43 days.

(21) Appl. No.: 11/576,541

(22) PCT Filed: Sep. 15, 2005

(86) PCT No.: PCT/GB2005/003568

§ 371 (c)(1),
(2), (4) Date: Apr. 3, 2007

(87) PCT Pub. No.: WO2006/037945

PCT Pub. Date: Apr. 13, 2006

(65) Prior Publication Data

US 2008/0051287 A1    Feb. 28, 2008

(30) Foreign Application Priority Data

Oct. 5, 2004 (GB) .................. 0422112.3
Feb. 7, 2005 (GB) .................. 0502487.2

(51) Int. Cl.
C07D 261/02 (2006.01)
C07D 231/00 (2006.01)
A01N 43/80 (2006.01)
A01N 43/56 (2006.01)
A61K 31/42 (2006.01)

(52) U.S. Cl. ............. 548/240; 548/356.1; 514/378; 514/403

(58) Field of Classification Search ......... 548/240, 548/356.1; 514/378, 403
See application file for complete search history.

(56) References Cited

U.S. PATENT DOCUMENTS

| | | | |
|---|---|---|---|
| 4,556,413 A | 12/1985 | Frater et al. | |
| 4,912,120 A | 3/1990 | Castelhano et al. | |
| 2001/0044382 A1 | 11/2001 | Ruegg | |
| 2004/0110749 A1 | 6/2004 | Nakatani et al. | |
| 2005/0215797 A1 | 9/2005 | Nakatani et al. | |
| 2005/0250822 A1 | 11/2005 | Mita et al. | |
| 2005/0256004 A1 | 11/2005 | Takahashi et al. | |
| 2007/0015661 A1 | 1/2007 | Rosinger et al. | |
| 2007/0015662 A1 | 1/2007 | Rosinger et al. | |
| 2007/0015805 A1 | 1/2007 | Schaper et al. | |

FOREIGN PATENT DOCUMENTS

| | | |
|---|---|---|
| EP | 1203768 A | 5/2002 |
| EP | 1405853 A | 4/2004 |
| EP | 1767528 A1 | 3/2007 |
| JP | 08225548 A | 9/1996 |
| JP | 19979328477 A | 12/1997 |
| JP | 19979328483 A | 12/1997 |
| JP | 2004002324 A | 1/2004 |
| JP | 2004224714 A | 8/2004 |
| JP | 2005035924 A | 2/2005 |
| JP | 2005145958 A | 6/2005 |
| JP | 2005213168 A | 8/2005 |
| WO | 9924409 | 5/1999 |
| WO | 03010165 | 2/2003 |
| WO | 2004/052849 A | 6/2004 |
| WO | 2005104848 A1 | 11/2005 |
| WO | 2005105755 | 11/2005 |
| WO | 2006024820 A1 | 3/2006 |
| WO | 2006038657 | 4/2006 |
| WO | 2006068092 | 6/2006 |
| WO | 2006097509 A2 | 9/2006 |
| WO | 2007003294 A1 | 1/2007 |
| WO | 2007023719 | 3/2007 |
| WO | 2007023764 | 3/2007 |

OTHER PUBLICATIONS

Sprague C L et al., Enhancing the margin of selectivity of RPA 201772 in Zea mays with antidotes, Weed Science 1999, 47(5), 492-497.

*Primary Examiner*—Kamal Saeed
*Assistant Examiner*—Samantha Shterengarts
(74) *Attorney, Agent, or Firm*—William A. Teoli, Jr.

(57) ABSTRACT

Compounds of formula: (I) wherein the substituents are as defined in claim 1, are suitable for use as herbicides. Also claimed are processes for the preparation of the claimed compounds, a herbicidal composition comprising the claimed compounds, and a method of controlling grasses and weeds using them.

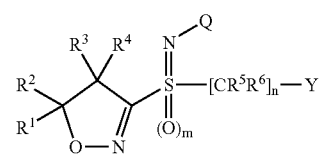

(I)

25 Claims, No Drawings

ISOXAZOLINE DERIVATIVES AND THEIR USE AS HERBICIDES

This application is a 371 of International Application No. PCT/GB2005/003568 filed Sep. 15, 2005, which claims priority to GB 0422112.3 filed Oct. 5, 2004, and GB 0502487.2 filed Feb. 7, 2005, the contents of which are incorporated herein by reference.

The present invention relates to novel, herbicidal isoxazoline compounds, to processes for their preparation, to compositions comprising those compounds, and to their use in controlling weeds, especially in crops of useful plants, or in inhibiting plant growth.

Isoxazoline compounds which display a herbicidal action are described, for example, in WO 01/012613, WO 02/062770, WO 03/000686, WO 04/014138 and JP 2005/035924. The preparation of these compounds is also described in WO 04/013106.

Novel sulfoximine compounds which display herbicidal and growth-inhibiting properties have now been found.

The present invention accordingly relates to compounds of formula I

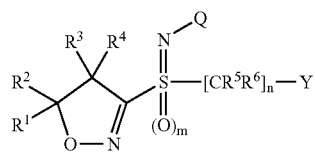

(I)

wherein $R^1$ and $R^2$ are each independently of the other hydrogen, $C_1$-$C_{10}$alkyl, $C_1$-$C_{10}$haloalkyl, $C_3$-$C_8$cycloalkyl or $C_3$-$C_8$cycloalkyl-$C_1$-$C_3$alkyl, or $R^1$ and $R^2$ together with the carbon atom to which they are bonded form a $C_3$-$C_7$ring, $R^3$ and $R^4$ are each independently of the other hydrogen, $C_1$-$C_{10}$alkyl, $C_1$-$C_{10}$haloalkyl, $C_3$-$C_8$cycloalkyl-$C_1$-$C_{10}$alkyl, $C_1$-$C_6$alkoxy-$C_1$-$C_{10}$alkyl or $C_3$-$C_8$cycloalkyl, or $R^3$ and $R^4$ together with the carbon atom to which they are bonded form a $C_3$-$C_7$ring, or $R^1$ with $R^3$ or $R^4$ and together with the carbon atoms to which they are bonded form a $C_5$-$C_8$ring, or $R^2$ with $R^3$ or $R^4$ and together with the carbon atoms to which they are bonded form a $C_5$-$C_8$ring;

$R^5$ and $R^6$ are each independently of the other hydrogen, $C_1$-$C_6$alkyl, $C_3$-$C_6$cycloalkyl, 4,5-dihydropyrazole-$CH_2$—, $C_1$-$C_6$alkylcarbonyloxy-$C_2$-$C_6$alkenyl-, $C_3$-$C_6$cycloalkylcarbonyl, $C_1$-$C_6$alkoxy-$C_1$-$C_6$alkylcarbonyl, $C_1$-$C_6$alkoxycarbonyl, cyano, $C_1$-$C_6$haloalkyl, $C_1$-$C_6$hydroxyalkyl, pyrrolyl-$CH_2$—, pyrazolyl-$CH_2$—, triazolyl-$CH_2$—, imidazolyl-$CH_2$—, tetrazolyl-$CH_2$—, indolyl-$CH_2$—, indazolyl-$CH_2$—, benzotriazolyl-$CH_2$—, $C_2$-$C_6$alkenyl, $C_2$-$C_6$alkynyl, $C_2$-$C_6$haloalkenyl, $C_2$-$C_6$alkenyloxy, $C_2$-$C_6$alkynyloxy, $C_1$-$C_6$alkylcarbonyl, $C_1$-$C_6$haloalkylcarbonyl, phenylcarbonyl or phenylcarbonyl substituted by one to three $R^9$, or $R^5$ and $R^6$ are each independently of the other phenoxycarbonyl or phenoxycarbonyl substituted by one to three $R^9$, or $R^5$ and $R^6$ are each independently of the other benzyloxycarbonyl or benzyloxycarbonyl substituted by one to three $R^9$, or $R^5$ and $R^6$ are each independently of the other nitro, formyl, carboxyl, halogen, azido, thiocyanato, tri($C_1$-$C_6$alkyl)silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)(O$C_1$-$C_6$alkyl)$_2$, $C_1$-$C_2$alkyl-NO$_2$, mercapto, phenylthio or phenylthio substituted by one to three $R^9$, or $R^5$ and $R^6$ are each independently of the other pyridylthio, $C_1$-$C_6$alkylthio, $C_1$-$C_6$haloalkylthio, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkyl-sulfonyl-$C_1$-$C_6$alkyl, $C_1$-$C_6$alkylsulphonyloxy-$C_1$-$C_6$alkyl, benzylsulfonyl or benzylsulfonyl substituted by one to three $R^9$, or $R^5$ and $R^6$ are each independently of the other phenylsulfinyl or phenylsulfinyl substituted by one to three $R^9$, or $R^5$ and $R^6$ are each independently of the other phenylsulfonyl or phenylsulfonyl substituted by one to three $R^9$, or $R^5$ and $R^6$ are each independently of the other hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, or $R^5$ and $R^6$ are each independently of the other benzyl or benzyl substituted by one to three $R^9$, or $R^5$ and $R^6$ are each independently of the other benzyloxy or benzyloxy substituted by one to three $R^9$, or $R^5$ and $R^6$ are each independently of the other —CONH—SO$_2$—$C_1$-$C_6$alkyl, —CONH—SO$_2$—$C_1$-$C_6$haloalkyl, —NHCHO, —NHCO—$C_1$-$C_6$alkyl, —NHCO—$C_1$-$C_6$haloalkyl, —NHCOO—$C_1$-$C_6$alkyl, —NHCONH—$C_1$-$C_6$alkyl, —NHCONH—$C_1$-$C_6$haloalkyl, —NHSO$_2$—$C_1$-$C_6$alkyl, —NHSO$_2$—$C_1$-$C_6$haloalkyl, —NHSO$_2$-phenyl or —NHSO$_2$-phenyl substituted by one to three $R^9$, or $R^5$ and $R^6$ are each independently of the other —OCO—$C_1$-$C_6$alkyl, —OCO—$C_1$-$C_6$haloalkyl, —OCO-phenyl or —OCO-phenyl substituted by one to three $R^9$, or $R^5$ and $R^6$ are each independently of the other —OCONH—$C_1$-$C_6$alkyl, —OCONH—$C_1$-$C_6$haloalkyl, —OCONH-phenyl or —OCONH-phenyl substituted by one to three $R^9$, or $R^5$ and $R^6$ are each independently of the other —CONR$^7$R$^8$ wherein $R^7$ and $R^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or $R^5$ and $R^6$ are each independently of the other phenyl or naphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, nitro, cyano, formyl, carboxyl, halogen, azido, thiocyanato, tri($C_1$-$C_6$alkyl)silyl, mercapto, phenylthio or phenylthio substituted by one to three $R^9$, phenylsulfinyl or phenylsulfinyl substituted by one to three $R^9$, —SF$_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH$_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$ haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or $R^5$ and $R^6$ are each independently of the other a 5- to 10-membered heterocycle containing one to three nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxy-carbonyl, benzyloxycarbonyl or benzyloxycarbonyl substituted by one to three $R^9$, phenylthio or phenylthio substituted by one to three $R^9$, phenylsulfinyl or phenylsulfinyl substituted by one to three $R^9$, nitro, cyano, formyl, carboxyl, halogen, azido, thio-cyanato, tri($C_1$-$C_6$alkyl)silyl, mercapto, —SF$_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, $R^5$ and $R^6$ together with the carbon atom to which they are bonded form a 3- to 10-membered ring which optionally contains one to three nitrogen, oxygen or sulfur atoms and which is optionally substituted by one to three substituents independently selected from $C_1$-$C_6$alkyl, $C_1$-$C_6$haloalkyl, $C_1$-$C_6$alkoxy, $C_1$-$C_6$alkoxycarbonyl, $C_1$-$C_6$alkylcarbonyl, $C_1$-$C_6$alkylsulfonyl, $C_1$-$C_6$haloalkylsulfonyl, $C_1$-$C_6$haloalkylcarbonyl, $C_1$-$C_6$alkenyl, halogen, cyano, nitro, phenyl or phenyl substituted by $C_1$-$C_6$haloalkyl, nitro, cyano or by halogen, phenylcarbonyl or phenylcarbonyl substituted by $C_1$-$C_6$haloalkyl, nitro, cyano or by halogen, or $R^5$ and $R^6$ together with the carbon atom to which they are bonded form a group of the formula C=CR$^{10}$R$^{11}$ wherein $R^{10}$ and $R^{11}$ are independently selected from hydrogen, $C_1$-$C_6$alkyl, $C_1$-$C_6$alkoxy, —NH($C_1$-$C_6$alkyl), —N($C_1$-$C_6$alkyl)$_2$, $C_1$-$C_6$alkoxy-$C_1$-$C_2$alkyl, $C_1$-$C_6$alkylcarbonyloxy, $C_1$-$C_6$alkylcarbonyloxy-$C_1$-$C_2$alkyl, $C_1$-$C_6$alkoxy-$C_1$-$C_2$alkylcarbonyloxy or $C_1$-$C_6$alkylcarbonyloxy-$C_1$-$C_2$alkylcarbonyloxy;

m is 0 or 1;

n is 0, 1 or 2;

Q is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by one to three $R^9$, or Q is benzylcarbonyl or benzylcarbonyl substituted by one to three $R^9$, or Q is pyridylcarbonyl or pyridylcarbonyl substituted by one to three $R^9$, or Q is phenoxycarbonyl or phenoxycarbonyl substituted by one to three $R^9$, or Q is benzyloxycarbonyl or benzyloxycarbonyl substituted by one to three $R^9$, or Q is nitro, formyl, tri($C_1$-$C_6$alkyl)silyl, $C_1$-$C_6$alkylcarbonyl-$C_1$-$C_2$alkyl, $C_1$-$C_6$alkoxy-carbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)(O$C_1$-$C_6$alkyl)$_2$, $C_1$-$C_2$alkyl-NO$_2$, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkyl-sulfonyl, $C_1$-$C_6$alkylsulfonyl-$C_1$-$C_6$alkyl, benzylsulfonyl or benzylsulfonyl substituted by one to three $R^9$, or Q is phenylsulfinyl or phenylsulfinyl substituted by one to three $R^9$, or Q is phenylsulfonyl or phenylsulfonyl substituted by one to three $R^9$, or Q is benzyl or benzyl substituted by one to three $R^9$, or Q is —CONH—SO$_2$—$C_1$-$C_6$alkyl or —CONH—SO$_2$—$C_1$-$C_6$haloalkyl, or Q is —CONR$^7$R$^8$ wherein $R^7$ and $R^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or Q is phenyl or naphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, nitro, cyano, formyl, carboxyl, halogen, azido, thiocyanato, tri($C_1$-$C_6$alkyl)silyl, mercapto, phenylthio or phenylthio substituted by one to three $R^9$, phenylsulfinyl or phenylsulfinyl substituted by one to three $R^9$, —SF$_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH$_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or Q is a 3- to 10-membered heterocycle containing one or more nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, phenylthio or phenylthio substituted by one to three $R^9$, phenylsulfinyl or phenylsulfinyl substituted by one to three $R^9$, nitro, cyano, formyl, carboxyl, halogen, azido, thiocyanato, tri($C_1$-$C_6$alkyl)silyl, mercapto, —SF$_5$, $C_1$-$C_6$alkylthio, $C_1$-$C_6$alkyl-sulfinyl, $C_1$-$C_6$alkylsulfonyl, $C_1$-$C_6$haloalkylthio, $C_1$-$C_6$haloalkylsulfinyl, $C_1$-$C_6$haloalkyl-sulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$-$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups; and Y is hydrogen, $C_1$-$C_6$alkyl, $C_3$-$C_6$cycloalkyl, $C_1$-$C_6$haloalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, nitro, cyano, formyl, hydroxyl, carboxyl, halogen, azido, thiocyanato, tri($C_1$-$C_6$alkyl)silyl, $C_1$-$C_6$alkylthio, $C_1$-$C_6$alkylsulfinyl, $C_1$-$C_6$alkylsulfonyl, benzylsulfonyl or benzylsulfonyl substituted by one to three $R^9$, or Y is phenylsulfonyl or phenylsulfonyl substituted by one to three $R^9$, or Y is $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, or Y is benzyloxy or benzyloxy substituted by one to three $R^9$, or Y is —CONH—$SO_2$—$C_1$-$C_6$alkyl or —CONH—$SO_2$—$C_1$-$C_6$haloalkyl, or Y is phenyl, naphthyl or tetrahydronaphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, benzyloxycarbonyl, nitro, cyano, formyl, carboxyl, halogen, azido, thiocyanato, tri($C_1$-$C_6$alkyl)silyl, mercapto, phenylthio, phenylsulfinyl, —SF$_5$, $C_1$-$C_6$alkylthio, $C_1$-$C_6$haloalkylthio, $C_1$-$C_6$haloalkyl-sulfinyl, $C_1$-$C_6$haloalkylsulfonyl, $C_1$-$C_6$alkylsulfinyl, $C_1$-$C_6$alkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$alkyloxy-$C_1$-$C_6$alkyl-, $C_3$-$C_6$cycloalkyloxy wherein one of the $CH_2$ groups is optionally replaced by an oxygen atom, $C_2$-$C_6$alkenyloxy, $C_2$-$C_6$-alkynyloxy, NHSO$_2$—$C_1$-$C_6$alkyl, NHSO$_2$—$C_1$-$C_6$haloalkyl, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ form a $C_3$-$C_8$alkylene group which optionally contains one oxygen or sulfur atom or one to two amino or $C_1$-$C_6$alkylamino groups, or Y is a 5- to 10-membered heterocycle containing one to three nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, nitro, cyano, formyl, carboxyl, halogen, azido, thiocyanato, tri($C_1$-$C_6$alkyl)silyl, mercapto, —SF$_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$alkyloxy-$C_1$-$C_6$alkyl-, $C_3$-$C_6$cycloalkyloxy wherein one of the $CH_2$ groups is optionally replaced by an oxygen atom, $C_2$-$C_6$alkenyloxy, $C_2$-$C_6$-alkynyloxy, NHSO$_2$—$C_1$-$C_6$alkyl, NHSO$_2$—$C_1$-$C_6$haloalkyl, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups;

$R^9$ are independently of each other $C_1$-$C_6$haloalkyl, $C_1$-$C_6$alkoxycarbonyl, nitro, cyano, formyl, carboxyl or halogen;

and to N-oxides, salts and optical isomers of compounds of formula I.

The compounds of the invention may contain one or more asymmetric carbon atoms, for example, in the —CR$^5$R$^6$— group and the —S(O)$_m$NQ group and may exist as enantiomers (or as pairs of diastereoisomers) or as mixtures of such. Further, when m is 0, the compounds of the invention are sulfilimines, which can exists in two enantiomeric forms, and the adjacent carbon can also exists in two enantiomeric forms. Compounds of general formula I can therefore exist as racemates, diastereoisomers, or single enantiomers, and the invention includes all possible isomers or isomer mixtures in all proportions. It is to be expected that for any given compound, one isomer may be more herbicidal than another.

The S=N bond shown in Formula I can also be represented as S$^+$—N$^-$ and there is still some debate in the literature whether the true character of this bond is a single or double bond. Whichever depiction is used, the actual compound remains the same.

Except where otherwise stated, alkyl groups and alkyl moieties of alkoxy, alkylthio, etc., suitably contain from 1 to 10, typically from 1 to 6, carbon atoms in the form of straight or branched chains. Examples are methyl, ethyl, n- and iso-propyl and n-, sec-, iso- and tert-butyl.

Except where otherwise stated, cycloalkyl groups and cycloalkyl moieties of cycloalkoxy, cycloalkyl-alkoxy, etc., suitably contain from 3 to 8, typically from 3 to 6, carbon atoms. Examples are cyclopropyl, cyclobutyl, cyclopentyl and cyclohexyl. The cycloalkyl radicals may be in bi- or tri-cyclic form.

Except where otherwise stated, haloalkyl groups and haloalkyl moieties of haloalkoxy, haloalkylthio, etc., also suitably contain from 1 to 6, typically from 1 to 4, carbon atoms in the form of straight or branched chains. Examples are difluoromethyl and 2,2,2-trifluoroethyl.

Except where otherwise stated, hydroxyalkyl groups also suitably contain from 1 to 6, typically from 1 to 4, carbon atoms in the form of straight or branched chains Examples are 1,2-dihydroxyethyl and 3-hydroxypropyl.

Except where otherwise stated, alkenyl and alkynyl moieties also suitably contain from 2 to 6, typically from 2 to 4, carbon atoms in the form of straight or branched chains. Examples are allyl, but-2-enyl, 3-methylbut-2-enyl, ethynyl, propargyl and but-2-ynyl.

Except where otherwise stated, haloalkenyl groups and haloalkynyl groups also, suitably contain from 2 to 6, typically from 2 to 4, carbon atoms in the form of straight or branched chains. Examples are trifluoroallyl and 1-chloro-prop-1-yn-3-yl.

Halo includes fluoro, chloro, bromo and iodo. Most commonly is fluoro, chloro or bromo and usually fluoro or chloro.

Except where otherwise stated, alkylene groups suitably contain from 1 to 10, typically from 1 to 6, carbon atoms in the form of straight or branched chains. Examples are methylene, ethylene, n- and iso-propylene and n-, sec-, iso- and tert-butylene.

Except where otherwise stated, heterocyclic groups suitably are 5- to 10-membered rings containing one to three nitrogen, oxygen or sulfur atoms, which may be optionally benzo-fused. Examples are furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzofuryl, isobenzofuryl, benzothiophenyl, isobenzothiophenyl, indolyl, isoindolyl, indazolyl, benzimidazolyl, benztriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl, isoquinolyl, cinnolinyl, phthalazinyl, quinazolinyl, quinoxalinyl, naphthyridinyl, benzotriazinyl, purinyl, pteridinyl, indolizinyl, benzo-1,3-dioxolyl, 4H-benzo-1,3-dioxinyl, and 4H-benzo-1,4-dioxinyl groups and, where appropriate, N-oxides and salts thereof.

The 3- to 10-membered rings which may be present as substituents in the compounds according to the invention include both carbocyclic and heterocyclic, aromatic and non-aromatic rings. Such rings may be in the form of single rings or in the form of polycyclic rings. They may carry further substituents and/or be benzo-fused. There may be mentioned by way of example phenyl, naphthyl, anthryl, indenyl and phenanthrenyl, the above-mentioned cycloalkyl radicals, and also rings containing oxygen, sulfur or nitrogen atoms, such as tetrahydrofuranyl, tetrahydropyranyl, 1,3-dioxolanyl, 1,3-dioxanyl, 1,4-dioxanyl, and morpholinyl, also furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzofuryl, isobenzofuryl, benzothiophenyl, isobenzothiophenyl, indolyl, isoindolyl, indazolyl, benzimidazolyl, benztriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl, isoquinolyl, cinnolinyl, phthalazinyl, quinazolinyl, quinoxalinyl, naphthyridinyl, benzotriazinyl, purinyl, pteridinyl, indolizinyl, benzo-1,3-dioxolyl, 4H-benzo-1,3-dioxinyl, and 4H-benzo-1,4-dioxinyl.

Where $R^5$ or $R^6$ is independently a heterocycle-methyl group, for example imidazolyl-CH$_2$—, the heterocycle is connected to the methyl group by a nitrogen.

The invention also includes N-oxides of the compounds of formula I.

The invention relates likewise to the salts which the compounds of formula I are able to form with amines, alkali metal and alkaline earth metal bases and quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylaamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as, for example, pyridine, quinoline, isoquinoline, morpholine, piperidine, pyrrolidine, indoline, quinuclidine and azepine; primary arylamines such as, for example, anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_a R_b R_c R_d)]OH$ wherein $R_a$, $R_b$, $R_c$ and $R_d$ are each independently of the others $C_1$-$C_4$alkyl. Other suitable tetraalkylammonium bases with other anions can be obtained, for example, by anion exchange reactions.

Furthermore, this invention relates to compounds of formula I wherein $R^1$ and $R^2$ are each independently hydrogen, $C_1$-$C_{10}$alkyl, $C_1$-$C_{10}$haloalkyl, $C_3$-$C_8$cyclo-alkyl or $C_3$-$C_8$cycloalkyl-$C_1$-$C_3$alkyl, or $R^1$ and $R^2$ together with the carbon atom to which they are bonded form a $C_3$-$C_7$ring, $R^3$ and $R^4$ are each independently hydrogen, $C_1$-$C_{10}$alkyl, $C_1$-$C_{10}$haloalkyl, $C_3$-$C_8$cyclo-alkyl-$C_1$-$C_{10}$alkyl, $C_1$-$C_6$alkoxy-$C_1$-$C_{10}$alkyl or $C_3$-$C_8$cycloalkyl, or $R^3$ and $R^4$ together with the carbon atom to which they are bonded form a $C_3$-$C_7$ring, or $R^1$ with $R^3$ or $R^4$ and together with the carbon atoms to which they are bonded form a $C_5$-$C_8$ring, or $R^2$ with $R^3$ or $R^4$ and together with the carbon atoms to which they are bonded form a $C_5$-$C_8$ring, $R^5$ and $R^6$ are each independently hydrogen, $C_1$-$C_6$alkyl, $C_3$-$C_6$cycloalkyl, $C_1$-$C_6$alkoxy-carbonyl, cyano, $C_1$-$C_6$haloalkyl, $C_1$-$C_6$hydroxyalkyl, pyrrolyl-$CH_2$—, pyrazolyl-$CH_2$—, triazolyl-$CH_2$—, imidazolyl-$CH_2$—, tetrazolyl-$CH_2$—, indolyl-$CH_2$—, indazolyl-$CH_2$—, benzo-triazolyl-$CH_2$—, $C_2$-$C_6$alkenyl, $C_2$-$C_6$alkynyl, $C_2$-$C_6$haloalkenyl, $C_2$-$C_6$alkenyloxy, $C_2$-$C_6$alkynyloxy, $C_1$-$C_6$alkylcarbonyl, $C_1$-$C_6$haloalkylcarbonyl, phenylcarbonyl or phenylcarbonyl substituted by $C_1$-$C_6$haloalkyl, $C_1$-$C_6$alkoxycarbonyl, nitro, cyano, formyl, carboxyl or by halogen, or $R_5$ and $R_6$ are each independently phenoxycarbonyl or phenoxycarbonyl substituted by $C_1$-$C_6$haloalkyl, $C_1$-$C_6$alkoxycarbonyl, nitro, cyano, formyl, carboxyl or by halogen, or $R^5$ and $R^6$ are each independently benzyloxycarbonyl or benzyloxycarbonyl substituted by $C_1$-$C_6$haloalkyl, $C_1$-$C_6$alkoxycarbonyl, nitro, cyano, formyl, carboxyl or by halogen, or $R^5$ and $R^6$ are each independently nitro, formyl, carboxyl, halogen, azido, thiocyanato, tri($C_1$-$C_6$alkyl)silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)(O$C_1$-$C_6$alkyl)$_2$, $C_1$-$C_2$alkyl-NO$_2$, mercapto, phenylthio or phenylthio substituted by $C_1$-$C_6$haloalkyl, $C_1$-$C_6$alkoxycarbonyl, nitro, cyano, formyl, carboxyl or by halogen, or $R^5$ and $R^6$ are each independently pyridylthio, $C_1$-$C_6$alkylthio, $C_1$-$C_6$haloalkylthio, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkylsulfonyl-$C_1$-$C_6$alkyl, benzylsulfonyl or benzylsulfonyl substituted by $C_1$-$C_6$haloalkyl, $C_1$-$C_6$alkoxycarbonyl, nitro, cyano, formyl, carboxyl or by halogen, or $R^5$ and $R^6$ are each independently phenylsulfinyl or phenylsulfinyl substituted by $C_1$-$C_6$haloalkyl, $C_1$-$C_6$alkoxycarbonyl, nitro, cyano, formyl, carboxyl or by halogen, or $R^5$ and $R^6$ are each independently phenylsulfonyl or phenylsulfonyl substituted by $C_1$-$C_6$haloalkyl, $C_1$-$C_6$alkoxycarbonyl, nitro, cyano, formyl, carboxyl or by halogen, or $R^5$ and $R^6$ are each independently hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, or $R^5$ and $R^6$ are each independently benzyl or benzyl substituted by $C_1$-$C_6$haloalkyl, $C_1$-$C_6$alkoxycarbonyl, nitro, cyano, formyl, carboxyl or by halogen, or $R^5$ and $R^6$ are each independently benzyloxy or benzyloxy substituted by $C_1$-$C_6$haloalkyl, $C_1$-$C_6$alkoxycarbonyl, nitro, cyano, formyl, carboxyl or by halogen, or $R^5$ and $R^6$ are each independently —CONH—SO$_2$—$C_1$-$C_6$alkyl, —CONH—SO$_2$—$C_1$-$C_6$haloalkyl, —NHCHO, —NHCO—$C_1$-$C_6$alkyl, —NHCO—$C_1$-$C_6$haloalkyl, —NHCOO—$C_1$-$C_6$alkyl, —NHCONH—$C_1$-$C_6$alkyl, —NHCONH—$C_1$-$C_6$haloalkyl, —NHSO$_2$—$C_1$-$C_6$alkyl, —NHSO$_2$—$C_1$-$C_6$haloalkyl, —NHSO$_2$-phenyl or —NHSO$_2$-phenyl substituted by $C_1$-$C_6$haloalkyl, $C_1$-$C_6$alkoxycarbonyl, nitro, cyano, formyl, carboxyl or by halogen, or $R^5$ and $R^6$ are each independently —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, or $R^5$ and $R^6$ are each independently —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or $R^5$ and $R^6$ are each independently —CONR$^7$R$^8$ wherein $R^7$ and $R^8$ are each independently hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which may contain one or more oxygen or sulfur atoms or one or more amino or alkylamino groups, or $R^5$ and $R^6$ are each independently phenyl or naphthyl, which rings may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by $C_1$-$C_6$haloalkyl, $C_1$-$C_6$alkoxycarbonyl, nitro, cyano, formyl, carboxyl or by halogen, nitro, cyano, formyl, carboxyl, halogen, azido, thiocyanato, tri($C_1$-$C_6$alkyl)silyl, mercapto, phenylthio or phenylthio substituted by $C_1$-$C_6$haloalkyl, $C_1$-$C_6$alkoxycarbonyl, nitro, cyano, formyl, carboxyl or by halogen, phenylsulfinyl or phenylsulfinyl substituted by $C_1$-$C_6$haloalkyl, $C_1$-$C_6$alkoxycarbonyl, nitro, cyano, formyl, carboxyl or by halogen, —$SF_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH$_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —CONR$^7$R$^8$ wherein $R^7$ and $R^8$ are each independently hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which may contain one or more oxygen or sulfur atoms or one or more amino or alkylamino groups, or $R^5$ and $R^6$ are each independently a 5- to 10-membered heterocycle containing one or more nitrogen, oxygen or sulfur atoms, which heterocycle may be benzo-fused, and which heterocycle may be substituted by $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl, benzyloxycarbonyl substituted by $C_1$-$C_6$haloalkyl, $C_1$-$C_6$alkoxycarbonyl, nitro, cyano, formyl, carboxyl or by halogen, phenylthio, phenylthio substituted by $C_1$-$C_6$haloalkyl, $C_1$-$C_6$alkoxycarbonyl, nitro, cyano, formyl, carboxyl or by halogen, phenylsulfinyl, phenylsulfinyl substituted by $C_1$-$C_6$haloalkyl, $C_1$-$C_6$alkoxycarbonyl, nitro, cyano, formyl, carboxyl or by halogen, nitro, cyano, formyl, carboxyl, halogen, azido, thiocyanato, tri($C_1$-$C_6$alkyl)silyl, mercapto, —$SF_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkyl-sulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —CONR$^7$R$^9$ wherein $R^7$ and $R^8$ are each independently hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which may contain one or more oxygen or sulfur atoms or one or more amino or alkylamino groups, $R^5$ and $R^6$ together with the carbon atom to which they are bonded form a 3- to 10-membered ring which may contain one or more nitrogen, oxygen or sulfur atoms and which may be substituted by $C_1$-$C_6$alkyl, $C_1$-$C_6$haloalkyl, $C_1$-$C_6$alkoxy, $C_1$-$C_6$alkoxycarbonyl, $C_1$-$C_6$alkylcarbonyl, $C_1$-$C_6$alkylsulfonyl, $C_1$-$C_6$haloalkylsulfonyl, $C_1$-$C_6$haloalkylcarbonyl, $C_1$-$C_6$alkenyl, halogen, cyano, nitro, phenyl or phenyl substituted by $C_1$-$C_6$haloalkyl, nitro, cyano or by halogen, phenylcarbonyl or phenylcarbonyl substituted by $C_1$-$C_6$haloalkyl, nitro, cyano or by halogen, or $R^5$ and $R^6$ together with the carbon atom to which they are bonded form a group of the formula C=CH$_2$, C=CH—$C_1$-$C_6$alkyl, C=C(halogen)$_2$, C=CH—N($C_1$-$C_6$alkyl)$_2$, C=CH—NH($C_1$-$C_6$alkyl) or C=CH—$C_1$-$C_6$alkoxy;

m is 0 or 1;

n is 0, 1 or 2;

Q is hydrogen, $C_1$-$C_6$alkyl, $C_3$-$C_6$cycloalkyl, $C_1$-$C_6$alkoxycarbonyl, tri($C_1$-$C_6$alkyl)silylethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by $C_1$-$C_6$haloalkyl, $C_1$-$C_6$alkoxycarbonyl, nitro, cyano, formyl, carboxyl or by halogen, or, Q is benzylcarbonyl or benzylcarbonyl substituted by $C_1$-$C_6$haloalkyl, $C_1$-$C_6$alkoxycarbonyl, nitro, cyano, formyl, carboxyl or by halogen, or Q is pyridylcarbonyl or pyridylcarbonyl substituted by $C_1$-$C_6$haloalkyl, $C_1$-$C_6$alkoxycarbonyl, nitro, cyano, formyl, carboxyl or by halogen or Q is phenoxycarbonyl or phenoxycarbonyl substituted by $C_1$-$C_6$haloalkyl, $C_1$-$C_6$alkoxycarbonyl, nitro, cyano, formyl, carboxyl or by halogen, or Q is benzyloxycarbonyl or benzyloxycarbonyl substituted by $C_1$-$C_6$haloalkyl, $C_1$-$C_6$alkoxycarbonyl, nitro, cyano, formyl, carboxyl or by halogen, or Q is nitro, formyl, tri($C_1$-$C_6$alkyl)silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)(OC$_1$-$C_6$alkyl)$_2$, $C_1$-$C_2$alkyl- NO₂, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkylsulfonyl-$C_1$-$C_6$alkyl, benzylsulfonyl or benzylsulfonyl substituted by $C_1$-$C_6$haloalkyl, $C_1$-$C_6$alkoxycarbonyl, nitro, cyano, formyl, carboxyl or by halogen, or Q is phenylsulfinyl or phenylsulfinyl substituted by $C_1$-$C_6$haloalkyl, $C_1$-$C_6$alkoxycarbonyl, nitro, cyano, formyl, carboxyl or by halogen, or Q is phenylsulfonyl or phenylsulfonyl substituted by $C_1$-$C_6$haloalkyl, $C_1$-$C_6$alkoxycarbonyl, nitro, cyano, formyl, carboxyl or by halogen, or Q is benzyl or benzyl substituted by $C_1$-$C_6$haloalkyl, $C_1$-$C_6$alkoxycarbonyl, nitro, cyano, formyl, carboxyl or by halogen, or Q is —CONE-SO₂—$C_1$-$C_6$alkyl or —CONH—SO₂—$C_1$-$C_6$haloalkyl, or Q is —CONR⁷R⁸ wherein R⁷ and R⁸ are each independently hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or R⁷ and R⁸ together form a $C_3$-$C_8$alkylene group which may contain one or more oxygen or sulfur atoms or one or more amino or alkylamino groups, or Q is phenyl or naphthyl, which rings may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by $C_1$-$C_6$haloalkyl, $C_1$-$C_6$alkoxycarbonyl, nitro, cyano, formyl, carboxyl or by halogen, nitro, cyano, formyl, carboxyl, halogen, azido, thiocyanato, tri($C_1$-$C_6$alkyl)silyl, mercapto, phenylthio or phenylthio substituted by $C_1$-$C_6$haloalkyl, $C_1$-$C_6$alkoxycarbonyl, nitro, cyano, formyl, carboxyl or by halogen, phenylsulfinyl or phenylsulfinyl substituted by $C_1$-$C_6$haloalkyl, $C_1$-$C_6$alkoxycarbonyl, nitro, cyano, formyl, carboxyl or by halogen, —SF₅, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH₃), $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—SO₂—$C_1$-$C_6$alkyl, —CONH—SO₂—$C_1$-$C_6$haloalkyl, —NHCO—$C_1$-$C_6$alkyl, —NHCO—$C_1$-$C_6$haloalkyl, —NHCO₂—$C_1$-$C_6$alkyl, —NHCO₂—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —CONR⁷R⁸ wherein R⁷ and R⁸ are each independently hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or R⁷ and R⁸ together form a $C_3$-$C_8$alkylene group which may contain one or more oxygen or sulfur atoms or one or more amino or alkylamino groups, or Q is a 3- to 10-membered heterocycle containing one or more nitrogen, oxygen or sulfur atoms, which heterocycle may be benzo-fused, and which heterocycle may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl, benzyloxycarbonyl substituted by $C_1$-$C_6$haloalkyl, $C_1$-$C_6$alkoxycarbonyl, nitro, cyano, formyl, carboxyl or by halogen, phenylthio, phenylthio substituted by $C_1$-$C_6$haloalkyl, $C_1$-$C_6$alkoxycarbonyl, nitro, cyano, formyl, carboxyl or by halogen, phenylsulfinyl, phenylsulfinyl substituted by $C_1$-$C_6$haloalkyl, $C_1$-$C_6$alkoxycarbonyl, nitro, cyano, formyl, carboxyl or by halogen, nitro, cyano, formyl, carboxyl, halogen, azido, thiocyanato, tri($C_1$-$C_6$alkyl)silyl, mercapto, —SF₅, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—SO₂—$C_1$-$C_6$alkyl, —CONH—SO₂—$C_1$-$C_6$haloalkyl, —NHCO—$C_1$-$C_6$alkyl, —NHCO—$C_1$-$C_6$haloalkyl, —NHCO₂—$C_1$-$C_6$alkyl, —NHCO₂—$C_1$-$C_6$haloalkyl, —OCO—$C_1$-$C_6$alkyl, —OCO—$C_1$-$C_6$haloalkyl, —OCO-phenyl or, —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —CONR⁷R⁸ wherein R⁷ and R⁸ are each independently hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or R⁷ and R⁸ together form a $C_3$-$C_8$alkylene group which may contain one or more oxygen or sulfur atoms or one or more amino or alkylamino groups; and Y is hydrogen, $C_1$-$C_6$alkyl, $C_3$-$C_6$cycloalkyl, $C_1$-$C_6$haloalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, nitro, cyano, formyl, hydroxyl, carboxyl, halogen, azido, thiocyanato, tri($C_1$-$C_6$alkyl)silyl, $C_1$-$C_6$alkylthio, $C_1$-$C_6$alkylsulfinyl, $C_1$-$C_6$alkylsulfonyl, benzylsulfonyl or benzylsulfonyl substituted by $C_1$-$C_6$haloalkyl, $C_1$-$C_6$alkoxycarbonyl, carboxyl, nitro, cyano or by halogen, or Y is phenylsulfonyl or phenylsulfonyl substituted by $C_1$-$C_6$haloalkyl, $C_1$-$C_6$alkoxycarbonyl, carboxyl, nitro, cyano or by halogen, or Y is $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, carboxyl, nitro, cyano or by halogen, or Y is benzyloxy or benzyloxy substituted by $C_1$-$C_6$haloalkyl, $C_1$-$C_6$alkoxycarbonyl, carboxyl, nitro, cyano or by halogen, or Y is —CONH—$SO_2$—$C_1$-$C_6$alkyl or —CONH—$SO_2$—$C_1$-$C_6$haloalkyl, or Y is phenyl, naphthyl or tetrahydronaphthyl, which rings may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, benzyloxycarbonyl, nitro, cyano, formyl, carboxyl, halogen, azido, thiocyanato, tri($C_1$-$C_6$alkyl)silyl, mercapto, phenylthio, phenylsulfinyl, —$SF_5$, $C_1$-$C_6$alkylthio, $C_1$-$C_6$haloalkylthio, $C_1$-$C_6$haloalkylsulfinyl, $C_1$-$C_6$haloalkylsulfonyl, $C_1$-$C_6$alkylsulfinyl, $C_1$-$C_6$alkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —$CONR^7R^8$ wherein $R^7$ and $R^8$ are each independently hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ form a $C_3$-$C_8$alkylene group which may contain one or more oxygen or sulfur atoms or one or more amino or alkylamino groups, or Y is a 5- to 10-membered heterocycle containing one or more nitrogen, oxygen or sulfur atoms, which heterocycle may be benzo-fused, and which heterocycle may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, nitro, cyano, formyl, carboxyl, halogen, azido, thiocyanato, tri($C_1$-$C_6$alkyl)silyl, mercapto, —$SF_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —$CONR^7R^8$ wherein $R^7$ and $R^8$ are each independently hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which may contain one or more oxygen or sulfur atoms or one or more amino or alkylamino groups, and to N-oxides, salts and optical isomers of compounds of formula I.

Alkyl and alkoxy radicals appearing in the substituent definitions are, for example, methyl, methoxy, ethyl, ethoxy, propyl, propoxy, butyl, butoxy, hexyl, hexyloxy, nonyl, nonyloxy and decyl and decyloxy and also branched isomers thereof. Suitable alkenyl and alkynyl radicals are derived from the mentioned alkyl radicals. Cycloalkyl radicals are generally cyclopropyl, cyclobutyl, cyclopentyl, cyclohexyl, cycloheptyl and cyclooctyl. The cycloalkyl radicals may be in bi- or tri-cyclic form. Phenyl radicals may be in substituted form. For example, Y may be a phenyl radical which can be substituted, for example, by alkoxy or by alkoxy substituted by halogen etc. The 3- to 10-membered rings which may be present as substituents in the compounds according to the invention include both carbocyclic and heterocyclic, aromatic and non-aromatic rings. Such rings may be in the form of single rings or in the form of polycyclic rings. They may carry further substituents and/or be benzo-fused. There may be mentioned by way of example phenyl, naphthyl, anthryl, indenyl and phenanthrenyl, the above-mentioned cycloalkyl radicals, and also rings containing oxygen, sulfur or nitrogen atoms, such as 1,3-dioxalanyl, dihydro-1,3-dioxolyl, tetrahydrofuranyl and morpholinyl, also furyl, thienyl, pyrrolyl, pyrazolyl, imidazolyl, 1,2,3-triazolyl, 1,2,4-triazolyl, oxazolyl, isoxazolyl, isothiazolyl, 1,2,3-oxadiazolyl, 1,2,4-oxadiazolyl, 1,3,4-oxadiazolyl, 1,2,5-oxadiazolyl, dihydroisoxazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl and indolizinyl.

The invention also includes N-oxides of the compounds of formula I.

The invention also includes the optical isomers of the compounds of formula I, especially those which have a chiral carbon atom in the —$CR^5R^6$— group and the —$S(O)_mNQ$ group.

TABLE 1

Compounds of formula I.1

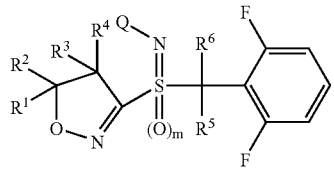

| $R^1$ | $R^2$ | $R^3$ | $R^4$ | $R^5$ | $R^6$ | m | Q |
|---|---|---|---|---|---|---|---|
| Me | Me | H | H | Br | $CF_3$ | 1 | H |
| Me | Me | H | H | $CO_2Me$ | F | 0 | H |
| Me | Me | H | H | CN | I | 1 | H |
| Me | Me | H | H | Br | I | 0 | H |
| $CH_2Cl$ | Me | H | H | Me | I | 1 | H |
| $CH_2Cl$ | Me | H | H | CN | $CO_2Me$ | 1 | H |
| $CH_2Cl$ | Me | H | H | H | I | 0 | H |
| Me | Me | H | H | Br | Cl | 1 | H |
| Me | Me | H | H | CN | Br | 1 | H |
| $CH_2Cl$ | Me | H | H | $CO_2Me$ | Br | 0 | H |
| $CH_2Cl$ | Me | H | H | CN | F | 1 | H |
| Me | Me | H | H | $CO_2Me$ | I | 0 | H |
| $CH_2Cl$ | Me | H | H | Me | F | 0 | H |
| $CH_2Cl$ | Me | H | H | Br | Br | 0 | H |
| $CH_2Cl$ | Me | H | H | H | $CO_2Me$ | 0 | H |
| $CH_2Cl$ | Me | H | H | H | Br | 1 | H |
| Me | Me | H | H | H | Br | 1 | H |
| Me | Me | H | H | Br | Br | 1 | H |
| Me | Me | H | H | H | $CF_3$ | 1 | H |
| $CH_2Cl$ | Me | H | H | H | H | 1 | H |
| $CH_2Cl$ | Me | H | H | $CO_2Me$ | I | 0 | H |
| Me | Me | H | H | Me | I | 1 | H |
| $CH_2Cl$ | Me | H | H | F | $CF_3$ | 1 | H |
| $CH_2Cl$ | Me | H | H | $CO_2Me$ | F | 1 | H |
| Me | Me | H | H | I | I | 0 | H |
| Me | Me | H | H | Me | Br | 1 | H |
| Me | Me | H | H | I | $CF_3$ | 0 | H |
| Me | Me | H | H | H | Br | 0 | H |
| $CH_2Cl$ | Me | H | H | H | Br | 0 | H |
| $CH_2Cl$ | Me | H | H | Me | $CF_3$ | 1 | H |
| Me | Me | H | H | Br | F | 0 | H |
| Me | Me | H | H | F | I | 1 | H |
| Me | Me | H | H | Br | F | 1 | H |
| Me | Me | H | H | H | H | 1 | H |
| $CH_2Cl$ | Me | H | H | CN | $CF_3$ | 1 | H |
| $CH_2Cl$ | Me | H | H | $CO_2Me$ | Cl | 1 | H |
| Me | Me | H | H | $CO_2Me$ | I | 1 | H |
| Me | Me | H | H | H | H | 0 | H |
| $CH_2Cl$ | Me | H | H | Me | F | 1 | H |
| $CH_2Cl$ | Me | H | H | I | I | 1 | H |
| Me | Me | H | H | Me | $CF_3$ | 0 | H |
| Me | Me | H | H | F | F | 1 | H |
| Me | Me | H | H | Br | $CF_3$ | 0 | H |
| $CH_2Cl$ | Me | H | H | Me | CN | 0 | H |
| Me | Me | H | H | Me | I | 0 | H |
| Me | Me | H | H | $CO_2Me$ | F | 1 | H |
| $CH_2Cl$ | Me | H | H | Me | Cl | 0 | H |
| $CH_2Cl$ | Me | H | H | CN | CN | 1 | H |
| Me | Me | H | H | Me | $CF_3$ | 1 | H |
| $CH_2Cl$ | Me | H | H | Br | Cl | 1 | H |
| Me | Me | H | H | H | Me | 1 | H |
| Me | Me | H | H | CN | $CO_2Me$ | 1 | H |
| Me | Me | H | H | CN | CN | 0 | H |
| Me | Me | H | H | F | F | 0 | H |
| Me | Me | H | H | $CO_2Me$ | Cl | 1 | H |
| $CH_2Cl$ | Me | H | H | Br | I | 1 | H |
| Me | Me | H | H | Me | $CO_2Me$ | 0 | H |
| Me | Me | H | H | H | Cl | 1 | H |
| $CH_2Cl$ | Me | H | H | Cl | F | 0 | H |
| $CH_2Cl$ | Me | H | H | CN | $CF_3$ | 0 | H |
| $CH_2Cl$ | Me | H | H | Cl | I | 0 | H |
| $CH_2Cl$ | Me | H | H | F | I | 0 | H |
| $CH_2Cl$ | Me | H | H | H | CN | 0 | H |
| $CH_2Cl$ | Me | H | H | Me | Br | 0 | H |
| Me | Me | H | H | Cl | F | 1 | H |
| $CH_2Cl$ | Me | H | H | Me | $CO_2Me$ | 1 | H |
| $CH_2Cl$ | Me | H | H | Me | Cl | 1 | H |
| $CH_2Cl$ | Me | H | H | $CO_2Me$ | $CF_3$ | 1 | H |
| $CH_2Cl$ | Me | H | H | Me | $CF_3$ | 0 | H |
| $CH_2Cl$ | Me | H | H | CN | Cl | 0 | H |
| $CH_2Cl$ | Me | H | H | I | $CF_3$ | 1 | H |
| Me | Me | H | H | H | $CO_2Me$ | 1 | H |
| $CH_2Cl$ | Me | H | H | Cl | Cl | 0 | H |
| $CH_2Cl$ | Me | H | H | $CO_2Me$ | Cl | 0 | H |
| Me | Me | H | H | H | F | 1 | H |
| $CH_2Cl$ | Me | H | H | F | F | 1 | H |
| $CH_2Cl$ | Me | H | H | Br | F | 1 | H |
| $CH_2Cl$ | Me | H | H | Br | $CF_3$ | 1 | H |
| $CH_2Cl$ | Me | H | H | $CF_3$ | $CF_3$ | 0 | H |
| $CH_2Cl$ | Me | H | H | CN | Br | 0 | H |
| Me | Me | H | H | H | I | 1 | H |
| $CH_2Cl$ | Me | H | H | CN | I | 0 | H |
| Me | Me | H | H | Me | F | 1 | H |
| $CH_2Cl$ | Me | H | H | Cl | $CF_3$ | 0 | H |
| Me | Me | H | H | Br | I | 1 | H |
| $CH_2Cl$ | Me | H | H | Br | Cl | 0 | H |
| $CH_2Cl$ | Me | H | H | CN | CN | 0 | H |
| Me | Me | H | H | Cl | $CF_3$ | 1 | H |
| $CH_2Cl$ | Me | H | H | Cl | I | 1 | H |
| $CH_2Cl$ | Me | H | H | CN | I | 1 | H |
| $CH_2Cl$ | Me | H | H | I | I | 0 | H |
| Me | Me | H | H | Me | Me | 1 | H |
| $CH_2Cl$ | Me | H | H | Me | Me | 0 | H |
| $CH_2Cl$ | Me | H | H | H | Me | 1 | H |
| $CH_2Cl$ | Me | H | H | H | $CO_2Me$ | 1 | H |
| $CH_2Cl$ | Me | H | H | Br | F | 0 | H |
| $CH_2Cl$ | Me | H | H | CN | Br | 1 | H |
| Me | Me | H | H | Me | F | 0 | H |
| Me | Me | H | H | CN | Br | 0 | H |
| $CH_2Cl$ | Me | H | H | $CO_2Me$ | $CF_3$ | 0 | H |
| $CH_2Cl$ | Me | H | H | Me | I | 0 | H |
| $CH_2Cl$ | Me | H | H | CN | Cl | 1 | H |
| Me | Me | H | H | F | I | 0 | H |
| Me | Me | H | H | CN | Cl | 1 | H |
| Me | Me | H | H | H | F | 0 | H |
| $CH_2Cl$ | Me | H | H | $CO_2Me$ | Br | 1 | H |
| Me | Me | H | H | I | $CF_3$ | 1 | H |
| Me | Me | H | H | Me | Me | 0 | H |
| Me | Me | H | H | Me | $CO_2Me$ | 1 | H |
| Me | Me | H | H | CN | $CF_3$ | 1 | H |
| Me | Me | H | H | $CO_2Me$ | $CF_3$ | 0 | H |
| Me | Me | H | H | CN | Cl | 0 | H |
| $CH_2Cl$ | Me | H | H | $CO_2Me$ | I | 1 | H |
| $CH_2Cl$ | Me | H | H | CN | F | 0 | H |
| $CH_2Cl$ | Me | H | H | F | F | 0 | H |
| $CH_2Cl$ | Me | H | H | H | I | 1 | H |
| Me | Me | H | H | Me | CN | 1 | H |
| $CH_2Cl$ | Me | H | H | Cl | Cl | 1 | H |
| $CH_2Cl$ | Me | H | H | Cl | F | 1 | H |
| $CH_2Cl$ | Me | H | H | H | F | 1 | H |
| Me | Me | H | H | CN | $CO_2Me$ | 0 | H |
| Me | Me | H | H | Me | Cl | 1 | H |
| Me | Me | H | H | $CO_2Me$ | Br | 0 | H |
| $CH_2Cl$ | Me | H | H | H | $CF_3$ | 0 | H |
| $CH_2Cl$ | Me | H | H | Me | CN | 1 | H |
| Me | Me | H | H | I | I | 1 | H |
| Me | Me | H | H | CN | $CF_3$ | 0 | H |
| $CH_2Cl$ | Me | H | H | Br | Br | 1 | H |
| $CH_2Cl$ | Me | H | H | Cl | $CF_3$ | 1 | H |
| $CH_2Cl$ | Me | H | H | F | I | 1 | H |

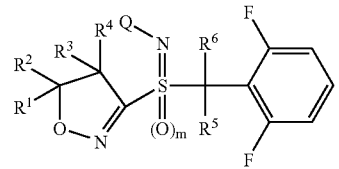

TABLE 1-continued

Compounds of formula I.1

I.1

| $R^1$ | $R^2$ | $R^3$ | $R^4$ | $R^5$ | $R^6$ | m | Q |
|---|---|---|---|---|---|---|---|
| $CH_2Cl$ | Me | H | H | H | CN | 1 | H |
| $CH_2Cl$ | Me | H | H | H | $CF_3$ | 1 | H |
| Me | Me | H | H | H | I | 0 | H |
| Me | Me | H | H | $CO_2Me$ | $CF_3$ | 1 | H |
| $CH_2Cl$ | Me | H | H | $CO_2Me$ | F | 0 | H |
| Me | Me | H | H | CN | I | 0 | H |
| Me | Me | H | H | $CO_2Me$ | Cl | 0 | H |
| $CH_2Cl$ | Me | H | H | H | F | 0 | H |
| Me | Me | H | H | Cl | Cl | 1 | H |
| $CH_2Cl$ | Me | H | H | I | $CF_3$ | 0 | H |
| Me | Me | H | H | Cl | I | 0 | H |
| $CH_2Cl$ | Me | H | H | F | $CF_3$ | 0 | H |
| Me | Me | H | H | $CF_3$ | $CF_3$ | 0 | H |
| Me | Me | H | H | CN | CN | 1 | H |
| Me | Me | H | H | Br | Cl | 0 | H |
| Me | Me | H | H | CN | F | 0 | H |
| Me | Me | H | H | Br | $CF_3$ | 0 | H |
| Me | Me | H | H | CN | F | 1 | H |
| Me | Me | H | H | H | Cl | 0 | H |
| $CH_2Cl$ | Me | H | H | H | Cl | 1 | H |
| Me | Me | H | H | H | Me | 0 | H |
| $CH_2Cl$ | Me | H | H | Me | Me | 1 | H |
| Me | Me | H | H | Cl | Cl | 0 | H |
| Me | Me | H | H | F | $CF_3$ | 1 | H |
| Me | Me | H | H | Br | Br | 0 | H |
| Me | Me | H | H | H | CN | 1 | H |
| $CH_2Cl$ | Me | H | H | H | H | 0 | H |
| Me | Me | H | H | Me | Br | 0 | H |
| $CH_2Cl$ | Me | H | H | $CF_3$ | $CF_3$ | 1 | H |
| Me | Me | H | H | Me | Cl | 1 | H |
| $CH_2Cl$ | Me | H | H | Br | I | 0 | H |
| Me | Me | H | H | Cl | I | 1 | H |
| $CH_2Cl$ | Me | H | H | Me | $CO_2Me$ | 0 | H |
| Me | Me | H | H | H | $CF_3$ | 0 | H |
| Me | Me | H | H | Me | CN | 0 | H |
| Me | Me | H | H | $CO_2Me$ | Br | 1 | H |
| Me | Me | H | H | $CF_3$ | $CF_3$ | 1 | H |
| $CH_2Cl$ | Me | H | H | H | Cl | 0 | H |
| Me | Me | H | H | Cl | $CF_3$ | 0 | H |
| $CH_2Cl$ | Me | H | H | H | Me | 0 | H |
| Me | Me | H | H | Cl | F | 0 | H |
| $CH_2Cl$ | Me | H | H | CN | $CO_2Me$ | 0 | H |
| Me | Me | H | H | F | $CF_3$ | 0 | H |
| Me | Me | H | H | H | CN | 0 | H |
| Me | Me | H | H | H | $CO_2Me$ | 0 | H |
| $CH_2Cl$ | Me | H | H | Me | Br | 1 | H |

Table 2:

Table 2 consists of 176 compounds of general formula I.1, where Q is —$COCH_3$, and $R^1$, $R^2$, $R^3$, $R^4$, $R^5$, $R^6$ and m have the values listed in Table 1. Thus compound 1 of Table 2 is the same as compound 1 of Table 1 except that in compound 1 of Table 2 Q is —$COCH_3$ instead of hydrogen. Similarly, compounds 2 to 176 of Table 2 are the same as compounds 2 to 176 of Table 1, respectively, except that in the compounds of Table 2 Q is —$COCH_3$ instead of hydrogen.

Table 3:

Table 3 consists of 176 compounds of general formula I.1, where Q is —CHO, and $R^1$, $R^2$, $R^3$, $R^4$, $R^5$, $R^6$ and m have the values listed in Table 1. Thus compound 1 of Table 3 is the same as compound 1 of Table 1 except that in compound 1 of Table 3 Q is —CHO instead of hydrogen. Similarly, compounds 2 to 176 of Table 3 are the same as compounds 2 to 176 of Table 1, respectively, except that in the compounds of Table 3 Q is —CHO instead of hydrogen.

Table 4:

Table 4 consists of 176 compounds of general formula I.1, where Q is —$CO_2CH_3$, and $R^1$, $R^2$, $R^3$, $R^4$, $R^5$, $R^6$ and m have the values listed in Table 1. Thus compound 1 of Table 4 is the same as compound 1 of Table 1 except that in compound 1 of Table 4 Q is —$CO_2CH_3$ instead of hydrogen. Similarly, compounds 2 to 176 of Table 4 are the same as compounds 2 to 176 of Table 1, respectively, except that in the compounds of Table 4 Q is —$CO_2CH_3$ instead of hydrogen.

Table 5:

Table 5 consists of 176 compounds of general formula I.1, where Q is —$CH_3$, and $R^1$, $R^2$, $R^3$, $R^4$, $R^5$, $R^6$ and m have the values listed in Table 1. Thus compound 1 of Table 5 is the same as compound 1 of Table 1 except that in compound 1 of Table 5 Q is —$CH_3$ instead of hydrogen. Similarly, compounds 2 to 176 of Table 5 are the same as compounds 2 to 176 of Table 1, respectively, except that in the compounds of Table 5 Q is —$CH_3$ instead of hydrogen.

Table 6:

Table 6 consists of 176 compounds of general formula I.1, where Q is —CN, and $R^1$, $R^2$, $R^3$, $R^4$, $R^5$, $R^6$ and m have the values listed in Table 1. Thus compound 1 of Table 6 is the same as compound 1 of Table 1 except that in compound 1 of Table 6 Q is —CN instead of hydrogen. Similarly, compounds 2 to 176 of Table 6 are the same as compounds 2 to 176 of Table 1, respectively, except that in the compounds of Table 6 Q is —CN instead of hydrogen.

Table 7:

Table 7 consists of 176 compounds of general formula I.1, where Q is —$NO_2$, and $R^1$, $R^2$, $R^3$, $R^4$, $R^5$, $R^6$ and m have the values listed in Table 1. Thus compound 1 of Table 7 is the same as compound 1 of Table 1 except that in compound 1 of Table 7 Q is —$NO_2$ instead of hydrogen. Similarly, compounds 2 to 176 of Table 7 are the same as compounds 2 to 176 of Table 1, respectively, except that in the compounds of Table 7 Q is —$NO_2$ instead of hydrogen.

Table 8:

Table 8 consists of 176 compounds of general formula I.1, where Q is —$CO_2{}^tBu$, and $R^1$, $R^2$, $R^3$, $R^4$, $R^5$, $R^6$ and m have the values listed in Table 1. Thus compound 1 of Table 8 is the same as compound 1 of Table 1 except that in compound 1 of Table 8 Q is —$CO_2{}^tBu$ instead of hydrogen. Similarly, compounds 2 to 176 of Table 8 are the same as compounds 2 to 176 of Table 1, respectively, except that in the compounds of Table 8 Q is —$CO_2{}^tBu$ instead of hydrogen.

Table 9:

Table 9 consists of 176 compounds of general formula I.2, where $R^1$, $R^2$, $R^3$, $R^4$, $R^5$, $R^6$, m and Q have the values listed in Table 1.

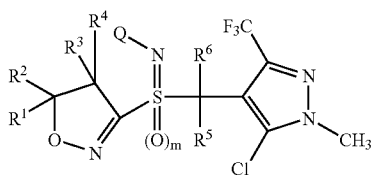

I.2

Thus compound 1 of Table 9 is the same as compound 1 of Table 1 except that in compound 1 of Table 9 Y is 5-chloro-1-methyl-3-trifluoromethyl-1H-pyrazol-4-yl instead of 2,6-difluorophenyl. Similarly, compounds 2 to 176 of Table 9 are the same as compounds 2 to 176 of Table 1, respectively, except that in the compounds of Table 9 Y is 5-chloro-1-methyl-3-trifluoromethyl-1H-pyrazol-4-yl instead of 2,6-difluorophenyl.

Table 10:

Table 10 consists of 176 compounds of general formula I.3, where $R^1$, $R^2$, $R^3$, $R^4$, $R^5$, $R^6$, m and Q have the values listed in Table 1.

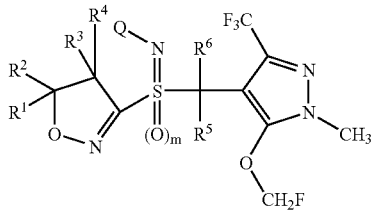

I.3

Thus compound 1 of Table 10 is the same as compound 1 of Table 1 except that in compound 1 of Table 10 Y is 5-fluoromethoxy-1-methyl-3-trifluoromethyl-1H-pyrazol-4-yl instead of 2,6-difluorophenyl. Similarly, compounds 2 to 176 of Table 10 are the same as compounds 2 to 176 of Table 1, respectively, except that in the compounds of Table 10 Y is 5-fluoromethoxy-1-methyl-3-trifluoromethyl-1H-pyrazol-4-yl instead of 2,6-difluorophenyl.

Table 11:

Table 11 consists of 176 compounds of general formula I.4, where $R^1$, $R^2$, $R^3$ $R^4$, $R^5$, $R^6$, m and Q have the values listed in Table 1.

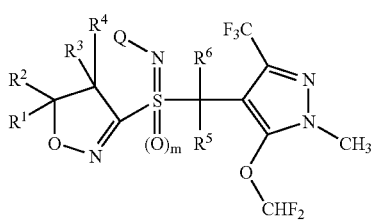

I.4

Thus compound 1 of Table 11 is the same as compound 1 of Table 1 except that in compound 1 of Table 11 Y is 5-difluoromethoxy-1-methyl-3-trifluoromethyl-1H-pyrazol-4-yl instead of 2,6-difluorophenyl. Similarly, compounds 2 to 176 of Table 11 are the same as compounds 2 to 176 of Table 1, respectively, except that in the compounds of Table 11 Y is 5-difluoromethoxy-1-methyl-3-trifluoromethyl-1H-pyrazol-4-yl instead of 2,6-difluorophenyl.

Table 12:

Table 12 consists of 176 compounds of general formula I.5, where $R^1$, $R^2$, $R^3$, $R^4$, $R^5$, $R^6$, m and Q have the values listed in Table 1.

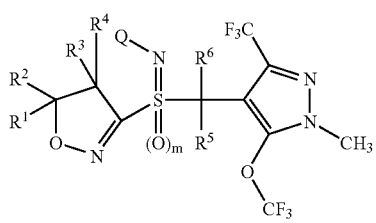

I.5

Thus compound 1 of Table 12 is the same as compound 1 of Table 1 except that in compound 1 of Table 12 Y is 1-methyl-5-trifluormethoxy-3-trifluoromethyl-1H-pyrazol-4-yl instead of 2,6-difluorophenyl. Similarly, compounds 2 to 176 of Table 12 are the same as compounds 2 to 176 of Table 1, respectively, except that in the compounds of Table 12 Y is 1-methyl-5-trifluoromethoxy-3-trifluoromethyl-1H-pyrazol-4-yl instead of 2,6-difluorophenyl.

Table 13:

Table 13 consists of 176 compounds of general formula I.6, where $R^1$, $R^2$, $R^3 R^4$, $R^5$, $R^6$ m and Q have the values listed in Table 1.

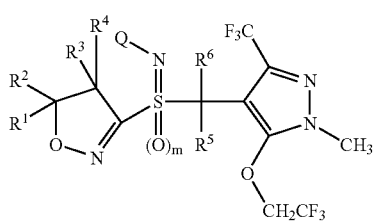

I.6

Thus compound 1 of Table 13 is the same as compound 1 of Table 1 except that in compound 1 of Table 13 Y is 1-methyl-5-(2,2,2-trifluoroethoxy)-3-trifluoromethyl-1H-pyrazol-4-yl instead of 2,6-difluorophenyl. Similarly, compounds 2 to 176 of Table 13 are the same as compounds 2 to 176 of Table 1, respectively, except that in the compounds of Table 13 Y is 1-methyl-5-(2,2,2-trifluoroethoxy)-3-trifluoromethyl-1H-pyrazol-4-yl instead of 2,6-difluorophenyl.

Table 14:

Table 14 consists of 176 compounds of general formula I.7, where $R^1$, $R^2$, $R^3$, $R^4$, $R^5$, $R^6$, m and Q have the values listed in Table 1.

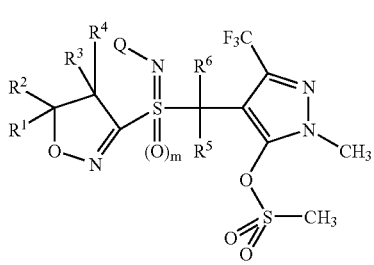

I.7

Thus compound 1 of Table 14 is the same as compound 1 of Table 1 except that in compound 1 of Table 14 Y is 1-methyl-5-methylsulfonyloxy-3-trifluoromethyl-1H-pyrazol-4-yl instead of 2,6-difluorophenyl. Similarly, compounds 2 to 176 of Table 14 are the same as compounds 2 to 176 of Table 1, respectively, except that in the compounds of Table 14 Y is 1-methyl-5-methylsulfonyloxy-3-trifluoromethyl-1H-pyrazol-4-yl instead of 2,6-difluorophenyl.

Table 15:

Table 15 consists of 176 compounds of general formula I.8, where $R^1$, $R^2R^3$, $R^4$, $R^5$, $R^6$ m and Q have the values listed in Table 1.

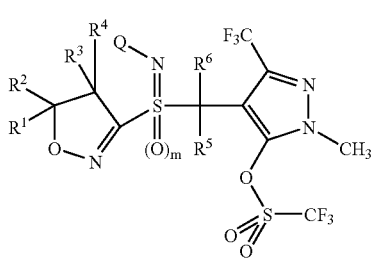

I.8

Thus compound 1 of Table 15 is the same as compound 1 of Table 1 except that in compound 1 of Table 15 Y is 1-methyl-3-trifluoromethyl-5-trifluoromethylsulfonyloxy-1H-pyrazol-4-yl instead of 2,6-difluorophenyl. Similarly, compounds 2 to 176 of Table 15 are the same as compounds 2 to 176 of Table 1, respectively, except that in the compounds of Table 15 Y is 1-methyl-3-trifluoromethyl-5-trifluoromethylsulfonyloxy-1H-pyrazol-4-yl instead of 2,6-difluorophenyl.

Table 16:

Table 16 consists of 176 compounds of general formula 1.2, where Q is —$COCH_3$, and $R^1$, $R^2$, $R^3$, $R^4$, $R^5$, $R^6$ and m have the values listed in Table 1. Thus compound 1 of Table 16 is the same as compound 1 of Table 9 except that in compound 1 of Table 16 Q is —$COCH_3$ instead of hydrogen. Similarly, compounds 2 to 176 of Table 16 are the same as compounds 2 to 176 of Table 9, respectively, except that in the compounds of Table 16 Q is —$COCH_3$ instead of hydrogen.

Table 17:

Table 17 consists of 176 compounds of general formula 1.3, where Q is —$COCH_3$, and $R^1$, $R^2$, $R^3$, $R^4$, $R^5$, $R^6$ and m have the values listed in Table 1. Thus compound 1 of Table 17 is the same as compound 1 of Table 10 except that in compound 1 of Table 17 Q is —$COCH_3$ instead of hydrogen. Similarly, compounds 2 to 176 of Table 17 are the same as compounds 2 to 176 of Table 10, respectively, except that in the compounds of Table 17 Q is —$COCH_3$ instead of hydrogen.

Table 18:

Table 18 consists of 176 compounds of general formula 1.4, where Q is —$COCH_3$, and $R^1$, $R^2$, $R^3$, $R^4R^5$, $R^6$ and m have the values listed in Table 1. Thus compound 1 of Table 18 is the same as compound 1 of Table 11 except that in compound 1 of Table 18 Q is —$COCH_3$ instead of hydrogen. Similarly, compounds 2 to 176 of Table 18 are the same as compounds 2 to 176 of Table 1, respectively, except that in the compounds of Table 18 Q is —$COCH_3$ instead of hydrogen.

Table 19:

Table 19 consists of 176 compounds of general formula I.5, where Q is —$COCH_3$, and $R^1$, $R^2$, $R^3$, $R^4$, $R^5$, $R^6$ and m have the values listed in Table 1. Thus compound 1 of Table 19 is the same as compound 1 of Table 12 except that in compound 1 of Table 19 Q is —$COCH_3$ instead of hydrogen. Similarly, compounds 2 to 176 of Table 19 are the same as compounds 2 to 176 of Table 12, respectively, except that in the compounds of Table 19 Q is —$COCH_3$ instead of hydrogen.

Table 20:

Table 20 consists of 176 compounds of general formula I.6, where Q is —$COCH_3$, and $R^1$, $R^2$, $R^3$, $R^4$, $R^5$, $R^6$ and m have the values listed in Table 1. Thus compound 1 of Table 20 is the same as compound 1 of Table 13 except that in compound 1 of Table 20 Q is —$COCH_3$ instead of hydrogen. Similarly, compounds 2 to 176 of Table 20 are the same as compounds 2 to 176 of Table 13, respectively, except that in the compounds of Table 20 Q is —$COCH_3$ instead of hydrogen.

Table 21:

Table 21 consists of 176 compounds of general formula I.7, where Q is —$COCH_3$, and $R^1$, $R^2$, $R^3$, $R^4$, $R^5$, $R^6$ and m have the values listed in Table 1. Thus compound 1 of Table 21 is the same as compound 1 of Table 14 except that in compound 1 of Table 21 Q is —$COCH_3$ instead of hydrogen. Similarly, compounds 2 to 176 of Table 21 are the same as compounds 2 to 176 of Table 14, respectively, except that in the compounds of Table 21 Q is —$COCH_3$ instead of hydrogen.

Table 22:

Table 22 consists of 176 compounds of general formula I.8, where Q is —$COCH_3$, and $R^1$, $R^2$, $R^3$, $R^4$, $R^5$, $R^6$ and m have the values listed in Table 1. Thus compound 1 of Table 22 is the same as compound 1 of Table 15 except that in compound 1 of Table 22 Q is —$COCH_3$ instead of hydrogen. Similarly, compounds 2 to 176 of Table 22 are the same as compounds 2 to 176 of Table 15, respectively, except that in the compounds of Table 22 Q is —$COCH_3$ instead of hydrogen.

Table 23:

Table 23 consists of 176 compounds of general formula I.2, where Q is —CHO, and $R^1$, $R^2$, $R^3$, $R^4$, $R^5$, $R^6$ and m have the values listed in Table 1. Thus compound 1 of Table 23 is the same as compound 1 of Table 9 except that in compound 1 of Table 23 Q is —CHO instead of hydrogen. Similarly, compounds 2 to 176 of Table 23 are the same as compounds 2 to 176 of Table 9, respectively, except that in the compounds of Table 23 Q is —CHO instead of hydrogen.

Table 24:

Table 24 consists of 176 compounds of general formula I.3, where Q is —CHO, and $R^1$, $R^2$, $R^3$, $R^4$, $R^5$, $R^6$ and m have the values listed in Table 1. Thus compound 1 of Table 24 is the same as compound 1 of Table 10 except that in compound 1 of Table 24 Q is —CHO instead of hydrogen. Similarly, compounds 2 to 176 of Table 24 are the same as compounds 2 to 176 of Table 10, respectively, except that in the compounds of Table 24 Q is —CHO instead of hydrogen.

Table 25:

Table 25 consists of 176 compounds of general formula I.4, where Q is —CHO, and $R^1$, $R^2$, $R^3$, $R^4$, $R^5$, $R^6$ and m have the values listed in Table 1. Thus compound 1 of Table 25 is the same as compound 1 of Table 11 except that in compound 1 of Table 25 Q is —CHO instead of hydrogen. Similarly, compounds 2 to 176 of Table 25 are the same as compounds 2 to 176 of Table 11, respectively, except that in the compounds of Table 25 Q is —CHO instead of hydrogen.

Table 26:

Table 26 consists of 176 compounds of general formula I.5, where Q is —CHO, and $R^1$, $R^2$, $R^3$, $R^4$, $R^5$, $R^6$ and m have the values listed in Table 1. Thus compound 1 of Table 26 is the same as compound 1 of Table 12 except that in compound 1 of Table 26 Q is —CHO instead of hydrogen. Similarly, compounds 2 to 176 of Table 26 are the same as compounds 2 to 176 of Table 12, respectively, except that in the compounds of Table 26 Q is —CHO instead of hydrogen.

Table 27:

Table 27 consists of 176 compounds of general formula I.6, where Q is —CHO, and $R^1$, $R^2$, $R^3$, $R^4$, $R^5$, $R^6$ and m have the values listed in Table 1. Thus compound 1 of Table 27 is the same as compound 1 of Table 13 except that in compound 1 of Table 27 Q is —CHO instead of hydrogen. Similarly, compounds 2 to 176 of Table 27 are the same as compounds 2 to 176 of Table 13, respectively, except that in the compounds of Table 27 Q is —CHO instead of hydrogen.

Table 28:

Table 28 consists of 176 compounds of general formula I.7, where Q is —CHO, and $R^1$, $R^2$, $R^3$, $R^4$, $R^5$, $R^6$ and m have the values listed in Table 1. Thus compound 1 of Table 28 is the same as compound 1 of Table 14 except that in compound 1 of Table 28 Q is —CHO instead of hydrogen. Similarly, compounds 2 to 176 of Table 28 are the same as compounds 2 to 176 of Table 14, respectively, except that in the compounds of Table 28 Q is —CHO instead of hydrogen.

Table 29:

Table 29 consists of 176 compounds of general formula I.8, where Q is —CHO, and $R^1$, $R^2$, $R^3$, $R^4$, $R^5$, $R^6$ and m have the values listed in Table 1. Thus compound 1 of Table 29 is the same as compound 1 of Table 15 except that in compound 1 of Table 29 Q is —CHO instead of hydrogen. Similarly, compounds 2 to 176 of Table 29 are the same as compounds 2 to 176 of Table 15, respectively, except that in the compounds of Table 29 Q is —CHO instead of hydrogen.

Table 30:

Table 30 consists of 176 compounds of general formula I.2, where Q is —$CO_2CH_3$, and $R^1$, $R^2$, $R^3$, $R^4$, $R^5$, $R^6$ and m have the values listed in Table 1. Thus compound 1 of Table 30 is the same as compound 1 of Table 9 except that in compound 1 of Table 30 Q is —$CO_2CH_3$ instead of hydrogen. Similarly, compounds 2 to 176 of Table 30 are the same as compounds 2 to 176 of Table 9, respectively, except that in the compounds of Table 30 Q is —$CO_2CH_3$ instead of hydrogen.

Table 31:

Table 31 consists of 176 compounds of general formula I.3, where Q is —$CO_2CH_3$, and $R^1$, $R^2$, $R^3$, $R^4$, $R^5$, $R^6$ and m have the values listed in Table 1. Thus compound 1 of Table 31 is the same as compound 1 of Table 10 except that in compound 1 of Table 31 Q is —$CO_2CH_3$ instead of hydrogen. Similarly, compounds 2 to 176 of Table 31 are the same as compounds 2 to 176 of Table 10, respectively, except that in the compounds of Table 31 Q is —$CO_2CH_3$ instead of hydrogen.

Table 32:

Table 32 consists of 176 compounds of general formula I.4, where Q is —$CO_2CH_3$, and $R^1$, $R^2$, $R^3$, $R^4$, $R^5$, $R^6$ and m have the values listed in Table 1. Thus compound 1 of Table 32 is the same as compound 1 of Table 11 except that in compound 1 of Table 32 Q is —$CO_2CH_3$ instead of hydrogen. Similarly, compounds 2 to 176 of Table 32 are the same as compounds 2 to 176 of Table 11, respectively, except that in the compounds of Table 32 Q is —$CO_2CH_3$ instead of hydrogen.

Table 33:

Table 33 consists of 176 compounds of general formula I.5, where Q is —$CO_2CH_3$, and $R^1$, $R^2$, $R^3$, $R^4$, $R^5$, $R^6$ and m have the values listed in Table 1. Thus compound 1 of Table 33 is the same as compound 1 of Table 12 except that in compound 1 of Table 33 Q is —$CO_2CH_3$ instead of hydrogen. Similarly, compounds 2 to 176 of Table 33 are the same as compounds 2 to 176 of Table 12, respectively, except that in the compounds of Table 33 Q is —$CO_2CH_3$ instead of hydrogen.

Table 34:

Table 34 consists of 176 compounds of general formula I.6, where Q is —$CO_2CH_3$, and $R^1$, $R^2$, $R^3$, $R^4$, $R^5$, $R^6$ and m have the values listed in Table 1. Thus compound 1 of Table 34 is the same as compound 1 of Table 13 except that in compound 1 of Table 34 Q is —$CO_2CH_3$ instead of hydrogen. Similarly, compounds 2 to 176 of Table 34 are the same as compounds 2 to 176 of Table 13, respectively, except that in the compounds of Table 34 Q is —$CO_2CH_3$ instead of hydrogen.

Table 35:

Table 35 consists of 176 compounds of general formula I.7, where Q is —$CO_2CH_3$, and $R^1$, $R^2$, $R^3$, $R^4$, $R^5$, $R^6$ and m have the values listed in Table 1. Thus compound 1 of Table 35 is the same as compound 1 of Table 14 except that in compound 1 of Table 35 Q is —$CO_2CH_3$ instead of hydrogen. Similarly, compounds 2 to 176 of Table 35 are the same as compounds 2 to 176 of Table 14, respectively, except that in the compounds of Table 35 Q is —$CO_2CH_3$ instead of hydrogen.

Table 36:

Table 36 consists of 176 compounds of general formula I.8, where Q is —$CO_2CH_3$, and $R^1$, $R^2$, $R^3$, $R^4$, $R^5$, $R^6$ and m have the values listed in Table 1. Thus compound 1 of Table 36 is the same as compound 1 of Table 15 except that in compound 1 of Table 36 Q is —$CO_2CH_3$ instead of hydrogen. Similarly, compounds 2 to 176 of Table 36 are the same as compounds 2 to 176 of Table 15, respectively, except that in the compounds of Table 36 Q is —$CO_2CH_3$ instead of hydrogen.

Table 37:

Table 37 consists of 176 compounds of general formula I.2, where Q is —$CH_3$, and $R^1$, $R^2$, $R^3$, $R^4$, $R^5$, $R^6$ and m have the values listed in Table 1. Thus compound 1 of Table 37 is the same as compound 1 of Table 9 except that in compound 1 of Table 37 Q is —$CH_3$ instead of hydrogen. Similarly, compounds 2 to 176 of Table 37 are the same as compounds 2 to 176 of Table 9, respectively, except that in the compounds of Table 37 Q is —$CH_3$ instead of hydrogen.

Table 38:

Table 38 consists of 176 compounds of general formula I.3, where Q is —$CH_3$, and $R^1$, $R^2$, $R^3$, $R^4$, $R^5$, $R^6$ and m have the values listed in Table 1. Thus compound 1 of Table 38 is the same as compound 1 of Table 10 except that in compound 1 of Table 38 Q is —CH$_3$ instead of hydrogen. Similarly, compounds 2 to 176 of Table 38 are the same as compounds 2 to 176 of Table 10, respectively, except that in the compounds of Table 38 Q is —CH$_3$ instead of hydrogen.

Table 39:

Table 39 consists of 176 compounds of general formula I.4, where Q is —CH$_3$, and R$^1$, R$^2$, R$^3$, R$^4$, R$^5$, R$^6$ and m have the values listed in Table 1. Thus compound 1 of Table 39 is the same as compound 1 of Table 11 except that in compound 1 of Table 39 Q is —CH$_3$ instead of hydrogen. Similarly, compounds 2 to 176 of Table 39 are the same as compounds 2 to 176 of Table 11, respectively, except that in the compounds of Table 39 Q is —CH$_3$ instead of hydrogen.

Table 40:

Table 40 consists of 176 compounds of general formula I.5, where Q is —CH$_3$, and R$^1$, R$^2$, R$^3$, R$^4$, R$^5$, R$^6$ and m have the values listed in Table 1. Thus compound 1 of Table 40 is the same as compound 1 of Table 12 except that in compound 1 of Table 40 Q is —CH$_3$ instead of hydrogen. Similarly, compounds 2 to 176 of Table 40 are the same as compounds 2 to 176 of Table 12, respectively, except that in the compounds of Table 40 Q is —CH$_3$ instead of hydrogen.

Table 41:

Table 41 consists of 176 compounds of general formula I.6, where Q is —CH$_3$, and R$^1$, R$^2$, R$^3$, R$^4$, R$^5$, R$^6$ and m have the values listed in Table 1. Thus compound 1 of Table 41 is the same as compound 1 of Table 13 except that in compound 1 of Table 41 Q is —CH$_3$ instead of hydrogen. Similarly, compounds 2 to 176 of Table 41 are the same as compounds 2 to 176 of Table 13, respectively, except that in the compounds of Table 41 Q is —CH$_3$ instead of hydrogen.

Table 42:

Table 42 consists of 176 compounds of general formula I.7, where Q is —CH$_3$, and R$^1$, R$^2$, R$^3$, R$^4$, R$^5$, R$^6$ and m have the values listed in Table 1. Thus compound 1 of Table 42 is the same as compound 1 of Table 14 except that in compound 1 of Table 42 Q is —CH$_3$ instead of hydrogen. Similarly, compounds 2 to 176 of Table 42 are the same as compounds 2 to 176 of Table 14, respectively, except that in the compounds of Table 42 Q is —CH$_3$ instead of hydrogen.

Table 43:

Table 43 consists of 176 compounds of general formula I.8, where Q is —CH$_3$, and R$^1$, R$^2$, R$^3$, R$^4$, R$^5$, R$^6$ and m have the values listed in Table 1. Thus compound 1 of Table 43 is the same as compound 1 of Table 15 except that in compound 1 of Table 43 Q is —CH$_3$ instead of hydrogen. Similarly, compounds 2 to 176 of Table 43 are the same as compounds 2 to 176 of Table 15, respectively, except that in the compounds of Table 43 Q is —CH$_3$ instead of hydrogen.

Table 44:

Table 44 consists of 176 compounds of general formula I.2, where Q is —CN, and R$^1$, R$^2$, R$^3$, R$^4$, R$^5$, R$^6$ and m have the values listed in Table 1. Thus compound 1 of Table 44 is the same as compound 1 of Table 9 except that in compound 1 of Table 44 Q is —CN instead of hydrogen. Similarly, compounds 2 to 176 of Table 44 are the same as compounds 2 to 176 of Table 9, respectively, except that in the compounds of Table 44 Q is —CN instead of hydrogen.

Table 45:

Table 45 consists of 176 compounds of general formula I.3, where Q is —CN, and R$^1$, R$^2$, R$^3$, R$^4$, R$^5$, R$^6$ and m have the values listed in Table 1. Thus compound 1 of Table 45 is the same as compound 1 of Table 10 except that in compound 1 of Table 45 Q is —CN instead of hydrogen. Similarly, compounds 2 to 176 of Table 45 are the same as compounds 2 to 176 of Table 10, respectively, except that in the compounds of Table 45 Q is —CN instead of hydrogen.

Table 46:

Table 46 consists of 176 compounds of general formula I.4, where Q is —CN, and R$^1$, R$^2$, R$^3$, R$^4$, R$^5$, R$^6$ and m have the values listed in Table 1. Thus compound 1 of Table 46 is the same as compound 1 of Table 11 except that in compound 1 of Table 46 Q is —CN instead of hydrogen. Similarly, compounds 2 to 176 of Table 46 are the same as compounds 2 to 176 of Table 11, respectively, except that in the compounds of Table 46 Q is —CN instead of hydrogen.

Table 47:

Table 47 consists of 176 compounds of general formula I.5, where Q is —CN, and R$^1$, R$^2$, R$^3$, R$^4$, R$^5$, R$^6$ and m have the values listed in Table 1. Thus compound 1 of Table 47 is the same as compound 1 of Table 12 except that in compound 1 of Table 47 Q is —CN instead of hydrogen. Similarly, compounds 2 to 176 of Table 47 are the same as compounds 2 to 176 of Table 12, respectively, except that in the compounds of Table 47 Q is —CN instead of hydrogen.

Table 48:

Table 48 consists of 176 compounds of general formula I.6, where Q is —CN, and R$^1$, R$^2$, R$^3$, R$^4$, R$^5$, R$^6$ and m have the values listed in Table 1. Thus compound 1 of Table 48 is the same as compound 1 of Table 13 except that in compound 1 of Table 48 Q is —CN instead of hydrogen. Similarly, compounds 2 to 176 of Table 48 are the same as compounds 2 to 176 of Table 13, respectively, except that in the compounds of Table 48 Q is —CN instead of hydrogen.

Table 49:

Table 49 consists of 176 compounds of general formula I.7, where Q is —CN, and R$^1$, R$^2$, R$^3$, R$^4$, R$^5$, R$^6$ and m have the values listed in Table 1. Thus compound 1 of Table 49 is the same as compound 1 of Table 14 except that in compound 1 of Table 49 Q is —CN instead of hydrogen. Similarly, compounds 2 to 176 of Table 49 are the same as compounds 2 to 176 of Table 14, respectively, except that in the compounds of Table 49 Q is —CN instead of hydrogen.

Table 50:

Table 50 consists of 176 compounds of general formula I.8, where Q is —CN, and R$^1$, R$^2$, R$^3$, R$^4$, R$^5$, R$^6$ and m have the values listed in Table 1. Thus compound 1 of Table 50 is the same as compound 1 of Table 15 except that in compound 1 of Table 50 Q is —CN instead of hydrogen. Similarly, compounds 2 to 176 of Table 50 are the same as compounds 2 to 176 of Table 15, respectively, except that in the compounds of Table 50 Q is —CN instead of hydrogen.

Table 51:

Table 51 consists of 176 compounds of general formula I.2, where Q is —NO$_2$, and R$^1$, R$^2$, R$^3$, R$^4$, R$^5$, R$^6$ and m have the values listed in Table 1. Thus compound 1 of Table 51 is the same as compound 1 of Table 9 except that in compound 1 of Table 51 Q is —NO$_2$ instead of hydrogen. Similarly, compounds 2 to 176 of Table 51 are the same as compounds 2 to 176 of Table 9, respectively, except that in the compounds of Table 51 Q is —NO$_2$ instead of hydrogen.

Table 52:

Table 52 consists of 176 compounds of general formula I.3, where Q is —NO$_2$, and R$^1$, R$^2$, R$^3$, R$^4$, R$^5$, R$^6$ and m have the values listed in Table 1. Thus compound 1 of Table 52 is the same as compound 1 of Table 10 except that in compound 1 of Table 52 Q is —NO$_2$ instead of hydrogen. Similarly, compounds 2 to 176 of Table 52 are the same as compounds 2 to 176 of Table 10, respectively, except that in the compounds of Table 52 Q is —NO$_2$ instead of hydrogen.

Table 53:

Table 53 consists of 176 compounds of general formula I.4, where Q is —NO$_2$, and R$^1$, R$^2$, R$^3$, R$^4$, R$^5$, R$^6$ and m have the values listed in Table 1. Thus compound 1 of Table 53 is the same as compound 1 of Table 11 except that in compound 1 of Table 53 Q is —NO$_2$ instead of hydrogen. Similarly, compounds 2 to 176 of Table 53 are the same as compounds 2 to 176 of Table 11, respectively, except that in the compounds of Table 53 Q is —NO$_2$ instead of hydrogen.

Table 54:

Table 54 consists of 176 compounds of general formula I.5, where Q is —NO$_2$, and R$^1$, R$^2$, R$^3$, R$^4$, R$^5$, R$^6$ and m have the values listed in Table 1. Thus compound 1 of Table 54 is the same as compound 1 of Table 12 except that in compound 1 of Table 54 Q is —NO$_2$ instead of hydrogen. Similarly, compounds 2 to 176 of Table 54 are the same as compounds 2 to 176 of Table 12, respectively, except that in the compounds of Table 54 Q is —NO$_2$ instead of hydrogen.

Table 55:

Table 55 consists of 176 compounds of general formula I.6, where Q is —NO$_2$, and R$^1$, R$^2$, R$^3$, R$^4$, R$^5$, R$^6$ and m have the values listed in Table 1. Thus compound 1 of Table 55 is the same as compound 1 of Table 13 except that in compound 1 of Table 55 Q is —NO$_2$ instead of hydrogen. Similarly, compounds 2 to 176 of Table 55 are the same as compounds 2 to 176 of Table 13, respectively, except that in the compounds of Table 55 Q is —NO$_2$ instead of hydrogen.

Table 56:

Table 56 consists of 176 compounds of general formula I.7, where Q is —NO$_2$, and R$^1$, R$^2$, R$^3$, R$^4$, R$^5$, R$^6$ and m have the values listed in Table 1. Thus compound 1 of Table 56 is the same as compound 1 of Table 14 except that in compound 1 of Table 56 Q is —NO$_2$ instead of hydrogen. Similarly, compounds 2 to 176 of Table 56 are the same as compounds 2 to 176 of Table 14, respectively, except that in the compounds of Table 56 Q is —NO$_2$ instead of hydrogen.

Table 57:

Table 57 consists of 176 compounds of general formula I.8, where Q is —NO$_2$, and R$^1$, R$^2$, R$^3$, R$^4$, R$^5$, R$^6$ and m have the values listed in Table 1. Thus compound 1 of Table 57 is the same as compound 1 of Table 15 except that in compound 1 of Table 57 Q is —NO$_2$ instead of hydrogen. Similarly, compounds 2 to 176 of Table 57 are the same as compounds 2 to 176 of Table 15, respectively, except that in the compounds of Table 57 Q is —NO$_2$ instead of hydrogen.

Table 58:

Table 58 consists of 176 compounds of general formula I.2, where Q is —CO$_2$$^t$Bu, and R$^1$, R$^2$, R$^3$, R$^4$, R$^5$, R$^6$ and m have the values listed in Table 1. Thus compound 1 of Table 58 is the same as compound 1 of Table 9 except that in compound 1 of Table 58 Q is —CO$_2$$^t$Bu instead of hydrogen. Similarly, compounds 2 to 176 of Table 58 are the same as compounds 2 to 176 of Table 9, respectively, except that in the compounds of Table 58 Q is —CO$_2$$^t$Bu instead of hydrogen.

Table 59:

Table 59 consists of 176 compounds of general formula I.3, where Q is —CO$_2$$^t$Bu, and R$^1$, R$^2$, R$^3$, R$^4$, R$^5$, R$^6$ and m have the values listed in Table 1. Thus compound 1 of Table 59 is the same as compound 1 of Table 10 except that in compound 1 of Table 59 Q is —CO$_2$$^t$Bu instead of hydrogen. Similarly, compounds 2 to 176 of Table 59 are the same as compounds 2 to 176 of Table 10, respectively, except that in the compounds of Table 59 Q is —CO$_2$$^t$Bu instead of hydrogen.

Table 60:

Table 60 consists of 176 compounds of general formula I.4, where Q is —CO$_2$$^t$Bu, and R$^1$, R$^2$, R$^3$, R$^4$, R$^5$, R$^6$ and m have the values listed in Table 1. Thus compound 1 of Table 60 is the same as compound 1 of Table 11 except that in compound 1 of Table 60 Q is —CO$_2$$^t$Bu instead of hydrogen. Similarly, compounds 2 to 176 of Table 60 are the same as compounds 2 to 176 of Table 11, respectively, except that in the compounds of Table 60 Q is —CO$_2$$^t$Bu instead of hydrogen.

Table 61:

Table 61 consists of 176 compounds of general formula I.5, where Q is —CO$_2$$^t$Bu, and R$^1$, R$^2$, R$^3$, R$^4$, R$^5$, R$^6$ and m have the values listed in Table 1. Thus compound 1 of Table 61 is the same as compound 1 of Table 12 except that in compound 1 of Table 61 Q is —CO$_2$$^t$Bu instead of hydrogen. Similarly, compounds 2 to 176 of Table 61 are the same as compounds 2 to 176 of Table 12, respectively, except that in the compounds of Table 61 Q is —CO$_2$$^t$Bu instead of hydrogen.

Table 62:

Table 62 consists of 176 compounds of general formula I.6, where Q is —CO$_2$$^t$Bu, and R$^1$, R$^2$, R$^3$, R$^4$, R$^5$, R$^6$ and m have the values listed in Table 1. Thus compound 1 of Table 62 is the same as compound 1 of Table 13 except that in compound 1 of Table 62 Q is —CO$_2$$^t$Bu instead of hydrogen. Similarly, compounds 2 to 176 of Table 62 are the same as compounds 2 to 176 of Table 13, respectively, except that in the compounds of Table 62 Q is —CO$_2$$^t$Bu instead of hydrogen.

Table 63:

Table 63 consists of 176 compounds of general formula I.7, where Q is —CO$_2$$^t$Bu, and R$^1$, R$^2$, R$^3$, R$^4$, R$^5$, R$^6$ and m have the values listed in Table 1. Thus compound 1 of Table 63 is the same as compound 1 of Table 14 except that in compound 1 of Table 63 Q is —CO$_2$$^t$Bu instead of hydrogen. Similarly, compounds 2 to 176 of Table 63 are the same as compounds 2 to 176 of Table 14, respectively, except that in the compounds of Table 63 Q is —CO$_2$$^t$Bu instead of hydrogen.

Table 64:

Table 64 consists of 176 compounds of general formula I.8, where Q is —CO$_2$$^t$Bu, and R$^1$, R$^2$, R$^3$, R$^4$, R$^5$, R$^6$ and m have the values listed in Table 1. Thus compound 1 of Table 64 is the same as compound 1 of Table 15 except that in compound 1 of Table 64 Q is —CO$_2$$^t$Bu instead of hydrogen. Similarly, compounds 2 to 176 of Table 64 are the same as compounds 2 to 176 of Table 15, respectively, except that in the compounds of Table 64 Q is —CO$_2$$^t$Bu instead of hydrogen.

A group of preferred compounds of formula I comprises those wherein

R$^1$ and R$^2$ are both C$_1$-C$_{10}$alkyl;

R$^3$ and R$^4$ are both hydrogen;

R$^5$ and R$^6$ are each independently of the other hydrogen, C$_1$-C$_6$alkyl, C$_1$-C$_6$alkoxycarbonyl or halogen;

m is 0 or 1;

n is 1;

Q is hydrogen, C$_1$-C$_6$alkyl, C$_1$-C$_6$alkoxycarbonyl, C$_1$-C$_6$haloalkoxycarbonyl, C$_1$-C$_6$alkylcarbonyl, C$_1$-C$_6$haloalkylcarbonyl, phenylcarbonyl or phenylcarbonyl substituted by one to three R$^9$, or Q is pyridylcarbonyl or pyridylcarbonyl substituted by one to three R$^9$, or Q is nitro, formyl, $C_1$-$C_6$alkylsulfonyl, or $C_1$-$C_6$haloalkylsulfonyl, or Q is phenylsulfonyl or phenylsulfonyl substituted by one to three $R^9$, or Q is a 3- to 10-membered heterocycle containing one to three nitrogen, oxygen or sulfur atoms, which heterocycle may be benzo-fused, and which heterocycle may be substituted by $C_1$-$C_6$alkyl, $C_1$-$C_6$haloalkyl, or cyano; and Y is phenyl, which is optionally substituted by one to three substituents independently selected from $C_1$-$C_6$alkyl, $C_1$-$C_6$haloalkyl, $C_1$-$C_6$alkoxycarbonyl, cyano, halogen, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkoxy, $C_1$-$C_6$haloalkoxy, or phenyl, or Y is a 5- to 10-membered heterocycle containing one to three nitrogen, oxygen or sulfur atoms, which is optionally substituted by one to three substituents independently selected from $C_1$-$C_6$alkyl, $C_1$-$C_6$haloalkyl, or halogen;

$R^9$ are independently of each other nitro or halogen;

and to N-oxides, salts and optical isomers of compounds of formula I.

A group of preferred compounds of formula I comprises those wherein $R^1$ and $R^2$ are each independently hydrogen, methyl, ethyl, cyclopropyl, cyclobutyl, fluoromethyl, chloromethyl, difluoromethyl or trifluoromethyl, or $R^1$ and $R^2$ together with the carbon atom to which they are bonded form a $C_3$- or $C_4$-ring, $R^3$ and $R^4$ are each independently hydrogen, methyl, ethyl, cyclopropyl, cyclobutyl, fluoromethyl, chloromethyl, difluoromethyl or trifluoromethyl, or $R^3$ and $R^4$ together with the carbon atom to which they are bonded form a $C_3$- or $C_4$-ring, or $R^1$ with $R^3$ or $R^4$ and together with the carbon atoms to which they are bonded form a $C_5$- or $C_6$-ring, or $R^2$ with $R^3$ or $R^4$ and together with the carbon atoms to which they are bonded form a $C_5$- or $C_6$-ring.

A group of especially preferred compounds of formula I comprises those wherein $R^1$, $R^2$, $R^3$, $R^4$ are each independently hydrogen, methyl, fluoromethyl, chloromethyl, difluoromethyl or trifluoromethyl.

A group of preferred compounds of formula I comprises those wherein $R^1$ and $R^2$ are both $C_1$-$C_{10}$alkyl.

A further group of especially preferred compound of formula I comprises those wherein $R^1$ and $R^2$ are both methyl.

Another group of especially preferred compounds of formula I comprises those wherein $R^3$ and $R^4$ are both hydrogen.

A group of preferred compounds of formula I comprises those wherein Q is hydrogen, $C_1$-$C_6$alkyl, $C_1$-$C_6$alkoxycarbonyl, $C_1$-$C_6$haloalkoxycarbonyl, $C_1$-$C_6$alkylcarbonyl, $C_1$-$C_6$haloalkylcarbonyl, phenylcarbonyl or phenylcarbonyl substituted by one to three $R^9$, or Q is pyridylcarbonyl or pyridylcarbonyl substituted by one to three $R^9$, or Q is nitro, formyl, $C_1$-$C_6$alkylsulfonyl, or $C_1$-$C_6$haloalkylsulfonyl, or Q is phenylsulfonyl or phenylsulfonyl substituted by one to three $R^9$, or Q is a 3- to 10-membered heterocycle containing one to three nitrogen, oxygen or sulfur atoms, which heterocycle may be benzo-fused, and which heterocycle may be substituted by $C_1$-$C_6$alkyl, $C_1$-$C_6$haloalkyl, or cyano; and $R^9$ are independently of each other nitro or halogen.

A group of especially preferred compounds of formula I comprises those wherein Q is hydrogen, acetyl, tert-butoxycarbonyl, 1-chloroethoxycarbonyl, 4-chlorophenylcarbonyl, 2-chloropyridylcarbonyl, 5-cyanopyrimidin-4-yl, ethoxycarbonylmethyl, formyl, methyl, methylsulfonyl, nitro, 4-nitrophenylcarbonyl, 4-nitrophenylsulfonyl, phenylcarbonyl, trimethylsilyl, trifluoroacetyl, 4-trifluoromethylpyrimidin-2-yl, trifluoromethylsulfonyl.

A further group of especially preferred compounds of formula I comprises those wherein Q is hydrogen, methyl, ethyl, isopropyl, cyano, methoxycarbonyl, ethoxycarbonyl, tert-butoxycarbonyl, benzyloxycarbonyl, cyclopropyl, difluoromethyl, trifluoroethyl, vinyl, difluorovinyl, dichlorovinyl, propargyl, acetyl, cyclopropylcarbonyl, benzoyl, benzylcarbonyl, pyridylcarbonyl, trifluoroacetyl, methoxycarbonylethyl, nitro, formyl, trimethylsilyl, methoxycarbonylmethyl, ethoxycarbonylmethyl, cyanomethyl, methylsulfonyl, cyclopropylsulfonyl, benzylsulfonyl, phenylsulfinyl, phenylsulfonyl, trifluoromethylsulfinyl, trifluoromethylsulfonyl, —CONH—SO$_2$—CH$_3$, —CONH—SO$_2$—CF$_3$, —CONH$_2$, —CONHCH$_3$ or —CON(CH$_3$)$_2$.

A further group of very especially preferred compounds of formula I comprises those wherein Q is hydrogen, cyano, nitro, formyl, methyl, acetyl, benzylcarbonyl and pyridylcarbonyl, methoxycarbonyl, ethoxycarbonyl, tert-butoxycarbonyl, phenylcarbonyl.

A further group of especially preferred compounds of formula I comprises those wherein Q is phenyl or which rings may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl.

A further group of especially preferred compounds of formula I comprises those wherein Q is 1,3-dioxalanyl, tetrahydrofuranyl, morpholinyl, furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthhydrinyl, benzotriazinyl, purinyl, pteridinyl and indolizinyl, which heterocycles may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl.

A further group of especially preferred compounds of formula I comprises those wherein $R^1$, $R^2$, $R^3$, $R^4$, $R^5$, $R^6$, m, n and Y are as defined above and Q is hydrogen, formyl or acetyl, most preferably hydrogen.

A further group of especially preferred compounds of formula I comprises those wherein $R^1$, $R^2$, $R^3$, $R^4$, m, n and Y are as defined above, $R^5$ and $R^6$ are independently hydrogen, alkoxycarbonyl, alkyl, cyano, halogen or haloalkyl and Q is hydrogen.

A further group of especially preferred compounds of formula I comprises those wherein m is 0 or 1.

A further group of very especially preferred compounds of formula I comprises those wherein m is 1.

A group of preferred compound of formula I comprises those wherein $R^5$ and $R^6$ are each independently of the other hydrogen, $C_1$-$C_6$alkyl, or halogen.

A group of preferred compound of formula I comprises those wherein $R^5$ and $R^6$ are each independently of the other hydrogen, fluoro, chloro, methyl, acetyl or methoxycarbonyl, preferably hydrogen, fluoro, chloro, or methyl.

A group of especially preferred compounds of formula I comprises those wherein $R^5$ and $R^6$ are each independently hydrogen, cyano, methyl, ethyl, isopropyl, methoxycarbonyl, ethoxycarbonyl, benzyloxycarbonyl, cyclopropyl, difluoromethyl, trifluoromethyl, trifluoroethyl, hydroxymethyl, methoxymethyl, methylthiomethyl, methylsulfinylmethyl, methylsulfonylmethyl, vinyl, difluorovinyl, dichlorovinyl, ethynyl, propargyl, acetyl, trifluoroacetyl, methoxycarbonylethyl, nitro, formyl, bromine, chlorine, fluorine, iodine, azido, trimethylsilyl, methoxycarbonylmethyl, ethoxycarbonylmethyl, cyanomethyl, cyanoethyl, mercapto, phenylthio, methylthio, methylsulfinyl, methylsulfonyl, benzylsulfonyl, phenylsulfinyl, phenylsulfonyl, trifluoromethylthio, trifluoromethylsulfinyl, trifluoromethylsulfonyl, hydroxyl, methoxy, ethoxy, trifluoromethoxy, trifluoroethoxy, methanesulfonyloxy, trifluoro-methanesulfonyloxy, phenoxy, benzyloxy, —CONH—SO$_2$—CH$_3$, —CONH—SO$_2$—CF$_3$, —NHCO—CH$_3$, —NHCO—CF$_3$, —OCO—CH$_3$, —OCO—CF$_3$, —OCO-phenyl, —OCONH—CH$_3$, —OCONH—CH$_2$CF$_3$, —OCONH-phenyl, —CONH$_2$, —CONHCH$_3$ or —CON(CH$_3$)$_2$.

A further group of very especially preferred compounds of formula I comprises those wherein $R^5$ and $R^6$ are each independently hydrogen, cyano, methyl, ethyl, methoxycarbonyl, ethoxycarbonyl, benzyloxycarbonyl, cyclopropyl, difluoromethyl, trifluoromethyl, trifluoroethyl, vinyl, difluorovinyl, dichlorovinyl, ethynyl, propargyl, acetyl, trifluoroacetyl, nitro, formyl, bromine, chlorine, fluorine, iodine, azido, trimethylsilyl, methoxycarbonylmethyl, ethoxycarbonylmethyl, cyanomethyl, mercapto, phenylthio, methylthio, methylsulfinyl, methylsulfonyl, benzylsulfonyl, phenylsulfinyl, phenylsulfonyl, trifluoromethylthio, trifluoromethylsulfinyl, trifluoromethylsulfonyl, hydroxyl, methoxy, ethoxy, trifluoromethoxy, trifluoroethoxy, methylthiomethyl, methylsulfinylmethyl, methylsulfonylmethyl, methylsulfonyloxy, trifluoromethyl-sulfonyloxy, phenoxy, benzyloxy, —CONH—SO$_2$—CH$_3$, —CONH—SO$_2$—CF$_3$, —NHCO—CH$_3$, —NHCO—CF$_3$, —OCO—CH$_3$, —OCO—CF$_3$, —OCO-phenyl, —OCONH—CH$_3$, —OCONH—CH$_2$CF$_3$ or —OCONH-phenyl.

A further group of especially preferred compounds of formula I comprises those wherein $R^5$ and $R^6$ are each independently phenyl or naphthyl, which rings may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl, and $R^6$ may additionally be hydrogen, cyano, methyl, ethyl, isopropyl, methoxycarbonyl, ethoxycarbonyl or benzyloxycarbonyl or halogen or trifluoromethyl.

A further group of very especially preferred compounds of formula I comprises those wherein $R^5$ and $R^6$ are each independently phenyl or naphthyl, which rings may be substituted by fluorine, chlorine, trifluoromethyl, methylsulfonyl, methoxy, trifluoromethoxy, cyano, nitro or by methoxycarbonyl and $R^6$ may additionally be hydrogen, cyano, methyl, ethyl, methoxycarbonyl or ethoxycarbonyl or halogen or trifluoromethyl.

A further group of especially preferred compounds of formula I comprises those wherein $R^5$ and $R^6$ are each independently 1,3-dioxalanyl, tetrahydrofuranyl, morpholinyl, furyl, thienyl, pyrrolyl, pyrazolyl, imidazolyl, 1,2,3-triazolyl, 1,2, 4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl, indolizinyl, dihydroisoxazolyl or a radical of formula

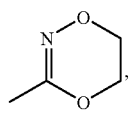

which heterocycles may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl, and $R_6$ may additionally be hydrogen, cyano, methyl, ethyl, isopropyl, methoxycarbonyl, ethoxycarbonyl or benzyloxycarbonyl or halogen or trifluoromethyl.

A further group of very especially preferred compounds of formula I comprises those wherein $R^5$ and $R^6$ are each independently isothiazolyl, isoxazolyl, pyrazolyl, thiadiazolyl, oxadiazolyl, dihydroisoxazolyl or a radical of formula

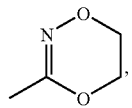

which rings may be substituted by methyl or methoxy and $R^6$ may additionally be hydrogen, cyano, methyl, ethyl, methoxycarbonyl or ethoxycarbonyl or halogen or trifluoromethyl.

A further group of especially preferred compounds of formula I comprises those wherein $R^5$ and $R^6$ together with the carbon atom to which they are bonded form a cyclopropyl ring which may be substituted by methyl, trifluoromethyl, methoxycarbonyl, ethoxycarbonyl, nitro, vinyl, 2-propenyl, acetyl, benzoyl, phenyl, trifluoroacetyl, methylsulfonyl, cyano, chlorine, fluorine, bromine or by methoxy.

A further group of very especially preferred compounds of formula I comprises those wherein $R^5$ and $R^6$ together with the carbon atom to which they are bonded form a cyclopropyl ring which may be substituted by methoxycarbonyl, ethoxycarbonyl, cyano, trifluoromethyl, methoxy, nitro, vinyl, bromine, fluorine or by chlorine.

A further group of especially preferred compounds of formula I comprises those wherein $R^5$ and $R^6$ together with the carbon atom to which they are bonded form a 3- to 6-membered heterocycle containing a nitrogen, oxygen or sulfur atom, which heterocycle may be substituted by methyl, trifluoromethyl, methoxycarbonyl, ethoxycarbonyl, trifluoroacetyl, trifluoromethylsulfonyl, methylsulfonyl, acetyl, phenyl, cyano, chlorine, fluorine, bromine or by methoxy.

A further group of especially preferred compounds of formula I comprises those wherein $R^5$ and $R^6$ together with the carbon atom to which they are bonded form a radical of formula C=CH$_2$, C=CH—CH$_3$, C=CF$_2$, C=CCl$_2$, C=CH—N(CH$_3$)$_2$, C=CH—NH(CH$_3$), C=CH—OCH$_3$ or C=CH—OC$_2$H$_5$.

A further group of especially preferred compounds of formula I comprises those wherein $R^1$, $R^2$, $R^3$, $R^4$, Q, m, n and Y are as defined above and $R^5$ and $R^6$ together with the carbon atom to which they are bonded form a 3- to 10-membered ring which may contain one or more nitrogen, oxygen or sulfur atoms, especially a 3- to 6-membered carbocyclic ring, more especially cyclopropyl, and which may be substituted by alkyl, haloalkyl, alkoxy, alkoxycarbonyl, halogen, nitro or by cyano.

A further group of especially preferred compounds of formula I comprises those wherein $R^1$, $R^2$, $R^3$, $R^4$, $R^6$, Q, m, n and Y are as defined above and $R^5$ is hydrogen.

A further group of especially preferred compounds of formula I comprises those wherein $R^1$, $R^2$, $R^3$, $R^4$, Q, m, n and Y are as defined above and $R^5$ and $R^6$ are both hydrogen.

A further group of especially preferred compounds of formula I comprises those wherein $R^1$, $R^2$, $R^3$, $R^4$, $R^6$, Q, m, n and Y are as defined above and $R^5$ is methoxycarbonyl.

A further group of especially preferred compounds of formula I comprises those wherein $R^1$, $R^2$, $R^3$, $R^4$, $R^6$, Q, m, n and Y are as defined above and $R^5$ is cyano.

A further group of especially preferred compounds of formula I comprises those wherein $R^1$, $R^2$, $R^3$, $R^4$, $R^6$, Q, m, n and Y are as defined above and $R^5$ is methyl.

A further group of especially preferred compounds of formula I comprises those wherein $R^1$, $R^2$, $R^3$, $R^4$, $R^6$, Q, m, n and Y are as defined above and $R^5$ is halogen.

A further group of especially preferred compounds of formula I comprises those wherein $R^1$, $R^2$, $R^3$, $R^4$, Q, m, n and Y are as defined above and $R^5$ and $R^6$ are both halogen, preferably independently selected from chlorine and fluorine.

A further group of especially preferred compounds of formula I comprises those wherein $R^1$, $R^2$, $R^3$, $R^4$, $R^6$, Q, m, n and Y are as defined above and $R^5$ is fluorine.

A further group of especially preferred compounds of formula I comprises those wherein $R^1$, $R^2$, $R^3$, $R^4$, Q, m, n and Y are as defined above and $R^5$ and $R^6$ are both fluorine.

A further group of especially preferred compounds of formula I comprises those wherein $R^1$, $R^2$, $R^3$, $R^4$, $R^6$, Q, m, n and Y are as defined above and $R^5$ is chlorine.

A further group of especially preferred compounds of formula I comprises those wherein $R^1$, $R^2$, $R^3$, $R^4$, Q, m, n and Y are as defined above and $R^5$ and $R^6$ are both chlorine.

A further group of especially preferred compounds of formula I comprises those wherein $R^1$, $R^2$, $R^3$, $R^4$, Q, m, n and Y are as defined above and $R^5$ is fluorine and $R^6$ is chlorine.

A further group of especially preferred compounds of formula I comprises those wherein $R^1$, $R^2$, $R^3$, $R^4$, $R^6$, Q, m, n and Y are as defined above and $R^5$ is $C_1$-$C_6$haloalkyl, especially trifluoromethyl.

A further group of especially preferred compounds of formula I comprises those wherein n is 1 or 2.

A further group of very especially preferred compounds of formula I comprises those wherein n is 1.

A group of preferred compounds of formula I comprises those wherein Y is phenyl, which is optionally substituted by one to three substituents independently selected from $C_1$-$C_6$alkyl, $C_1$-$C_6$haloalkyl, $C_1$-$C_6$alkoxycarbonyl, cyano, halogen, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkoxy, $C_1$-$C_6$haloalkoxy, or phenyl, or Y is a 5- to 10-membered heterocycle containing one to three nitrogen, oxygen or sulfur atoms, which is optionally substituted by one to three substituents independently selected from $C_1$-$C_6$alkyl, $C_1$-$C_6$haloalkyl, or halogen.

A group of preferred compounds of formula I comprises those wherein Y is phenyl, which is optionally substituted by one to three substituents independently selected from $C_1$-$C_6$alkyl, $C_1$-$C_6$haloalkyl, $C_1$-$C_6$alkoxycarbonyl, cyano, halogen, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkoxy, $C_1$-$C_6$haloalkoxy, or phenyl.

A group of preferred compounds of formula I comprises those wherein Y is phenyl optionally substituted by one to three substituents independently selected from cyano, difluoromethoxy, ethoxycarbonyl, fluoro, methoxycarbonyl, methyl, methyl-sulfonyl, phenyl, trifluoromethoxy, trifluoromethyl, or trifluoromethylthio.

A group of preferred compounds of formula I comprises those wherein Y is 2-biphenyl.

A group of preferred compounds of formula I comprises those wherein Y is 2-chloro-3-ethoxycarbonyl-6-methylsulfonylphenyl.

A group of preferred compounds of formula I comprises those wherein Y is 2-cyanophenyl.

A group of preferred compounds of formula I comprises those wherein Y is 2-difluoromethoxyphenyl.

A group of preferred compounds of formula I comprises those wherein Y is 2,3-difluorophenyl.

A group of preferred compounds of formula I comprises those wherein Y is 2,4-difluorophenyl.

A group of preferred compounds of formula I comprises those wherein Y is 2,5-difluorophenyl.

A group of preferred compounds of formula I comprises those wherein Y is 2,6-difluorophenyl.

A group of preferred compounds of formula I comprises those wherein Y is 3,5-difluorophenyl.

A group of preferred compounds of formula I comprises those wherein Y is 2,6-difluoro-3-tolyl.

A group of preferred compounds of formula I comprises those wherein Y is 4-ethoxycarbonyl-2-fluorophenyl.

A group of preferred compounds of formula I comprises those wherein Y is 6-fluoro-4H-benzo[1,3]dioxin-8-yl.

A group of preferred compounds of formula I comprises those wherein Y is 2-fluoro-4-methoxycarbonylphenyl.

A group of preferred compounds of formula I comprises those wherein Y is 2-fluorophenyl.

A group of preferred compounds of formula I comprises those wherein Y is 2-fluoro-6-trifluoromethylphenyl.

A group of preferred compounds of formula I comprises those wherein Y is phenyl.

A group of preferred compounds of formula I comprises those wherein Y is 2-tolyl.

A group of preferred compounds of formula I comprises those wherein Y is 2-trifluoromethoxyphenyl.

A group of preferred compounds of formula I comprises those wherein Y is 2-trifluoromethylphenyl.

A group of preferred compounds of formula I comprises those wherein Y is 2-trifluoromethylthio.

A group of preferred compounds of formula I comprises those wherein Y is a 5- to 10-membered heterocycle containing one to three nitrogen, oxygen or sulfur atoms, which is optionally substituted by one to three substituents independently selected from $C_1$-$C_6$alkyl, $C_1$-$C_6$haloalkyl, or halogen.

A group of preferred compounds of formula I comprises those wherein Y is pyrazolyl optionally substituted by one to three substituents independently selected from difluoromethoxy, difluoromethyl, methoxy, methyl, or trifluoromethyl.

A group of especially preferred compounds of formula I comprises those wherein Y is pyrazol-4-yl.

A group of preferred compounds of formula I comprises those wherein Y is 5-chloro-1-methyl-3-trifluoromethyl-1H-pyrazol-4-yl.

A group of preferred compounds of formula I comprises those wherein Y is 3-difluoromethoxy-1-methyl-5-trifluoromethyl-1H-pyrazol-4-yl.

A group of preferred compounds of formula I comprises those wherein Y is 1-methyl-3-difluoromethyl-1H-pyrazol-4-yl.

A group of preferred compounds of formula I comprises those wherein Y is 1-methyl-3-trifluoromethyl-1H-pyrazol-4-yl.

A further group of especially preferred compounds of formula I comprises those wherein Y is phenyl, naphthyl, tetrahydronaphthyl, 1,3-dioxalanyl, tetrahydrofuranyl, morpholinyl, furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthhydrinyl, benzotriazinyl, purinyl, pteridinyl or indolizinyl, which rings may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoroethoxy, trifluoromethoxy, fluoromethoxy, difluoromethoxy, methylsulfonyloxy, trifluoromethylsulfonyloxy, cyano, nitro, methoxycarbonyl, —$CONH_2$ or by carboxyl.

A further group of very especially preferred compounds of formula I comprises those wherein Y is phenyl, pyrimidin-5-yl, pyridin-3-yl, isothiazol-4-yl, isoxazol-4-yl, pyrazol-4-yl or thiophen-3-yl, each of these groups optionally substituted by halogen, alkyl, haloalkyl, alkoxy, haloalkoxy, alkylsulfonyloxy, haloalkylsulfonyloxy.

1.1) The compounds of formula I, wherein $R^1$, $R^2$, $R^3$, $R^4$, $R^5$, $R^6$, Q, n and Y are as defined above and m is 0 or 1, can be prepared by processes known per se, e.g. by reacting a compound of formula Ia

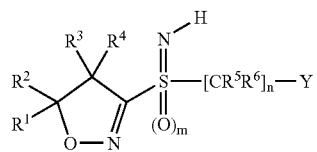

(Ia)

wherein $R^1$, $R^2$, $R^3$, $R^4$, $R^5$, $R^6$, n and Y are as defined above and m is 0 or 1

1.1A) with compounds of the formula

Q-$X^A$ 

wherein Q is as defined above and $X^A$ is a suitable leaving group such as e.g. a halogen, such as bromide, a carboxylate, such as acetate, an alkyl- or aryl-sulfonate, such as p-toluenesulfonate, an imide, such as succinimide, a sulfonimide, such as bis(phenyl-sulfonyl)imide, or a haloalkylsulfonate, such as trifluoromethylsulfonate, in the presence of a base, e.g. a trialkylamine, such as triethylamine, pyridine, an alkali metal carbonate, such as potassium carbonate or caesium carbonate, an alkyl-lithium compound, such as methyl-lithium, n-butyl-lithium and tert-butyl-lithium, a lithium dialkylamide, such as lithium diisopropylamide, a metal hydride, preferably an alkali metal hydride, such as sodium hydride, or an alkali metal amide, such as sodium amide, a metal bis(tri ($C_1$-$C_6$alkyl)silyl)amide, such as lithium bis(trimethylsilyl) amide, a metal alkoxide, such as potassium tert-butoxide, an alkali metal hydroxide or alkaline earth metal hydroxide, such as sodium hydroxide, or a phosphazene base, such as N'-tert-butyl-N,N,N', N',N'',N''-hexamethylphosphorimidic triamide ($P_1$-$^t$Bu), 1-ethyl-2,2,4,4,4-pentakis(dimethylamino)-2-lambda$^5$-5,4-lambda$^5$-5-catenadi(phosphazene) ($P_2$-Et), 1-tert-butyl-2,2,4,4,4-pentakis(dimethylamino)-2-lambda$^5$-5,4-lambda$^5$-5-catenadi-(phosphazene) ($P_2$-$^t$Bu), 2-tert-butylimino-2-diethylamino-1,3-dimethyl-perhydro-1,3,2-diazaphosphorine (BEMP) or 2,8,9-triisobutyl-2,5,8,9-tetraaza-1-phosphabicyclo[3.3.3]-undecane (Verkade's base), optionally in the presence of a diluent, e.g. dimethylsulfoxide, N,N-dimethylformamide, an ether, such as tetrahydrofuran (THF) or 1,2-dimethoxyethane, or a halogenated hydrocarbon, such as dichloromethane, or mixtures thereof and optionally in the presence of a catalyst, e.g. a phase transfer catalyst, such as tetrabutylammonium bromide or triethylbenzylammonium chloride, or a transition metal catalyst, such as palladium(II) acetate [Pd(OAc)$_2$] or tris (dibenzylideneacetone)di-palladium(0) [Pd$_2$(dba)$_3$], usually in the presence of a phosphine ligand, such as 2,2'-bis(diphenylphosphino)-1,1'-binaphthyl (BINAP) or triphenyl phosphine, or CuI or CuBr in a temperature range of from −120° C. to 160° C., preferably from −80° C. to 120° C. Such processes are known in the literature and are described, for example, in J. Org. Chem., 1993 (58) 1922-1923; Tetrahedron Lett., 1996 (37) 3985-3988; J. Org. Chem., 1973 (38) 20-26; Synthesis, 2002 (7) 879-887; Chem. Eur. J. 2001 (7) 1118-1128, Org. Lett., 2004 (6) 3293-3296;

1.1B) with compounds of the general formula

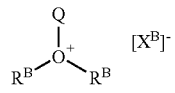

wherein Q and $R^B$ are $C_1$-$C_6$alkyl, such as methyl or ethyl, and $X^B$ is a suitable counter ion, such as tetrafluoroborate, in the presence of a base, e.g. an alkali metal carbonate, such as potassium carbonate or sodium carbonate, and in the presence of a solvent, e.g. a halogenated hydrocarbon, such as dichloromethane, usually in a temperature range from −50° C. to 30° C. Such processes are known in the literature and are described, for example, in J. Org. Chem., 1978 (43) 4136-4140 and 4140-4143; J. Am. Chem. Soc., 1970, 92, 6594;

1.1C) with a formylating agent, e.g. trimethyl orthoformate, optionally in the presence of an acid, such as p-toluenesulfonic acid, optionally in the presence of an inert solvent, such as toluene or xylene, usually in a temperature range from 0° C. to 200° C., preferably from 50° C. to 120° C. Such processes are known in the literature and are described, for example in Tetrahedron Letters, 1987 (36) 4149.

1.1D) with a nitration reagent, e.g. nitric acid, optionally in the presence of an acid, such as sulfuric acid, optionally in the presence of an acid anhydride, such as acetic anhydride, optionally in the presence of an inert solvent, e.g. a halogenated hydrocarbon, such as dichloromethane, in a temperature range from −50° C. to 80° C., preferably −20° C. to 50° C. Such processes are known in the literature and are described, for example in Synthesis, 1986 (5) 426-427, Synthesis, 2003 (4) 565-569.

1.2) The compounds of formula Ia, wherein $R^1$, $R^2$, $R^3$, $R^4$, $R^5$, $R^6$, n and Y are as defined above and m is 0 or 1, can be prepared by processes known per se, e.g. by 1.2A) deprotection of a compound of formula Ib

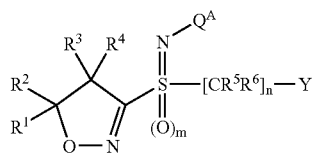
(Ib)

wherein $R^1$, $R^2$, $R^3$, $R^4$, $R^5$, $R^6$, n and Y are as defined above, m is 0 or 1 and $Q^A$ is an electron withdrawing group, e.g. alkylsulfonyl, such as methylsulfonyl, arylsulfonyl, such as p-toluenesulfonyl or nitrophenylsulfonyl, or a haloalkylcarbonyl, such as trifluoromethylcarbonyl, or an alkoxycarbonyl, such as tert-butoxycarbonyl, or a substituted benzoyl, such as 4-nitrobenzoyl or 4-chlorobenzoyl, under acidic conditions, e.g. in the presence of a mineral acid, such as sulfuric acid or hydrochloric acid or an organic acid, such as trifluoroacetic acid (J. Am. Chem. Soc., 1973 (95) 7418-7423; Chem. Eur. J. 2001 (7) 1118-1128, J. Med. Chem., 2003 (46) 4405-4418, J. Org. Chem., 1976 (41) 1728) or under basic conditions, e.g. in the presence of an alkali metal carbonate, such as potassium carbonate, or an alkali metal hydroxide, such as sodium hydroxide (Org. Lett., 2004 (8) 1305-1307), or in the presence of a nucleophile, e.g. a mercaptan, such as phenylthiol (Tetrahedron Lett., 2002 (43) 2749-2751), in the presence of a diluent, e.g. an ether, such as tetrahydrofuran (THF) or 1,4-dioxane, water, a halogenated hydrocarbon, such as dichloromethane, an alcohol, such as methanol or ethanol, or mixtures thereof, usually in a temperature range of −20° C. to 150° C., preferably −20° C. to 50° C.;

1.2B) reacting compounds of formula II

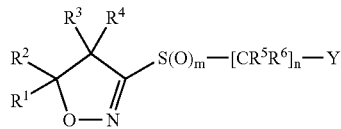
(II)

wherein $R^1$, $R^2$, $R^3$, $R^4$, $R^5$, $R^6$, n and Y are as defined above and m is 0 or 1, with an alkali metal azide, such as sodium azide, under acidic conditions, usually in the presence of sulfuric acid, optionally in the presence of a solvent, e.g. a halogenated hydrocarbon, such as chloroform or dichloromethane, in a temperature range of −20° C. to 50° C., preferably −20° C. to 25° C. (Synthesis, 2003 (4) 565-569; J. Am. Chem. Soc., 1973 (95) 7418), or by reacting with O-mesitylenesulfonylhydroxylamine in the presence of a solvent, e.g. a halogenated hydrocarbon, such as chloroform or dichloromethane, in a temperature range from −20° C. to 50° C., preferably −20° C. to 25° C. (J. Org. Chem., 1974 (39) 24598-2459; J. Org. Chem., 1973 (38) 1239).

1.3) Compounds of formula Ib, wherein $R^1$, $R^2$, $R^3$, $R^4$, $R^5$, $R^6$, n and Y are as defined above, m is 0 or 1 and $Q^A$ is an electron withdrawing group, e.g. alkylsulfonyl, such as methylsulfonyl, arylsulfonyl, such as p-toluenesulfonyl or nitrophenylsulfonyl, or a haloalkylcarbonyl, such as trifluoromethylcarbonyl, or an alkoxycarbonyl, such as tert-butoxycarbonyl, can be prepared by processes known per se, by reacting e.g. the compound of formula II (see above) wherein $R^1$, $R^2$, $R^3$, $R^4$, $R^5$, $R^6$, n and Y are as defined above and m is 0 or 1, 1.3A) with an imination reagent of the formula $$ArI=NQ^A$$

wherein Ar is a phenyl group, optionally substituted, e.g. with halogens, $Q^A$ is an electron withdrawing group, e.g. alkylsulfonyl, such as methylsulfonyl, arylsulfonyl, such as p-toluenesulfonyl or nitrophenylsulfonyl, or a haloalkylcarbonyl, such as trifluoromethylcarbonyl, or an alkoxycarbonyl, such as tert-butoxycarbonyl, optionally in the presence of a transition metal catalyst, e.g. $Rh_2(OAc)_4$, $Cu(I)PF_6$, $Cu(OTf)_2$ or CuOTf or $AgNO_3$, optionally in the presence of a ligand, e.g. 4,4',4''-tri-tert-butyl-2,2':6',2''-terpyridine, and in the presence of an inert solvent, such as toluene, dichloromethane or acetonitrile. The imination reagent $ArI=NQ^A$ can be preformed or generated in situ by reacting a compound of the formula $$H_2N-Q^A$$

with a periodine compound, such as $PhI(OAc)_2$ or $PhI(O-COCF_3)_2$, optionally in the presence of a weak base, such as MgO. Such processes are known in the literature and are described, for example, in Org. Lett., 2004 (8) 1305-1307, Tetrahedron Lett., 1998 (39) 4805, Synthesis, 1999 (7) 12512-1260;

1.3B) with an organic azide, such as tert-butoxycarbonyl azide or p-toluene-sulfonyl azide, optionally in the presence of a transition metal catalyst, such as $FeCl_2$, in the presence of a solvent, e.g. a halogenated hydrocarbon, such as chloroform or dichloromethane, in a temperature range from −20° C. to 50° C., preferably −20° C. to 25° C. (Synthesis, 1999 1251-1260, Tetrahedron Lett., 1998 (39) 5015).

1.4) The compounds of formula II wherein $R^1$, $R^2$, $R^3$, $R^4$, $R^5$, $R^6$, n and Y are as defined above and m is 1 can be prepared by processes known per se by reacting compounds of formula II wherein $R^1$, $R^2$, $R^3$, $R^4$, $R^5$, $R^6$, n and Y are as defined above and m is 0 with a suitable organic or inorganic oxidising agent, e.g. a peroxy acid, such as 3-chloroperoxybenzoic acid, peracetic acid or hydrogen peroxide, an alkoxyperoxide or a periodate, such as sodium periodiate, optionally in the presence of a diluent, such as a halogenated hydrocarbon, e.g. dichloromethane or 1,2-dichloroethane, an alcohol, e.g. methanol, N,N-dimethylformamide, water or acetic acid or a mixture thereof. The reactions are usually carried out in a temperature range of from −80° C. to 120° C., preferably from −20° C. to 50° C. Such processes are known in the literature and are described e.g. in J. Org. Chem., 2003 (68) 3849-3859; J. Med. Chem., 2003 (46) 3021-3032; J. Org. Chem., 2003 (68) 500-511; Bioorg. Med. Chem., 1999 (9) 1837-1844.

1.5) The compounds of formula II wherein $R^1$, $R^2$, $R^3$, $R^4$, $R^5$, $R^6$ and Y are as defined above, m is 0, and n is 1, can be prepared, for example, by starting from compounds of formula II wherein $R^1$, $R^2$, $R^3$, $R^4$ and Y are as defined above, $R^5$ and $R^6$ are hydrogen, m is 0, and n is 1, or compounds of formula II wherein $R^1$, $R^2$, $R^3$, $R^4$, $R^5$ and Y are as defined above, $R^6$ is hydrogen, m is 0, and n is 1,

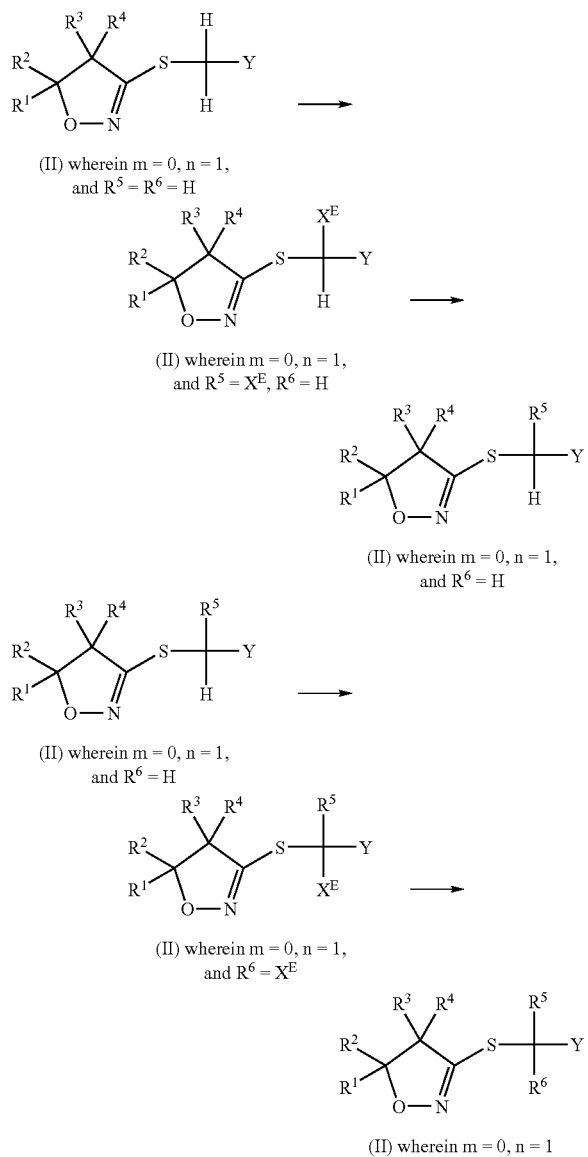

by reacting those compounds with a halogenating agent, e.g. bromine or an N-halosuccinimide, such as N-chlorosuccinimide or N-bromosuccinimide, to form compounds of formula II wherein $R^1$, $R^2$, $R^3$, $R^4$ and Y are as defined above, $R^5$ is $X^E$, and $X^E$ in turn is halogen, $R^6$ is hydrogen, m is 0, and n is 1, or compounds of formula II wherein $R^1$, $R^2$, $R^3$, $R^4$, $R^5$ and Y are as defined above, $R^6$ is $X^E$, and $X^E$ in turn is halogen, m is 0, and n is 1, respectively, optionally in the presence of a diluent, e.g. acetic acid or a halogenated hydrocarbon, such as $CCl_4$ or dichloromethane, in a temperature range of from $-80°$ C. to $120°$ C., preferably from $-20°$ C. to $60°$ C.

The compounds of formula II wherein $R^1$, $R^2$, $R^3$, $R^4$ and Y are as defined above, $R^5$ is $X^E$, and $X^E$ in turn is halogen, $R^6$ is hydrogen, m is 0, and n is 1, or compounds of formula II wherein $R^1$, $R^2$, $R^3$, $R^4$, $R^5$ and Y are as defined above, $R^6$ is $X^E$, and $X^E$ in turn is halogen, m is 0, and n is 1, can then be oxidised directly as described above, or alternatively (in a second step) reacted with compounds of formula M-$R^5$ or M-$R^6$ respectively, wherein $R^5$ and $R^6$ are as defined above and M-$R^5$ or M-$R^6$ is a suitable salt or an organometal compound in which M is e.g. Li, MgBr, Na, K or tetraalkylammonium, optionally in the presence of a Lewis acid, e.g. $SnCl_4$, optionally in the presence of a complexing agent, e.g. hexamethylphosphoramide (HMPA) or 1,3-dimethyl-3,4,5,6-tetrahydro-2(1H)-pyrimidinone (DMPU), and optionally in the presence of a diluent, e.g. acetonitrile, dichloromethane, diethyl ether or tetrahydrofuran (THF), in a temperature range of from $-120°$ C. to $100°$ C., preferably from $-80°$ C. to $80°$ C. Such processes are known in the literature and are described, for example, in J. Org. Chem., 1998 (63) 3706-3716; J. Chem. Soc. Perkin Trans., 1995 (22) 2845-2848; Synthesis 1982 (2), 131-132; Liebigs Annalen, 1993, 49-54 and Synth. Commun., 1990 (20) 1943-1948.

Compounds of formula II wherein $R^1$, $R^2$, $R^3$, $R^4$, n and Y are as defined above, $R^5$ and $R^6$ are hydrogen, m is 0, have previously been described in WO 01/012613, WO 03/000686 and WO 04/014138

2) The compounds of formula I, wherein $R^1$, $R^2$, $R^3$, $R^4$, $R^5$, $R^6$, Q, n and Y are as defined above and m is 1, can also be prepared by processes known per se, by reacting e.g. a compound of formula I, wherein $R^1$, $R^2$, $R^3$, $R^4$, $R^5$, $R^6$, Q, n and Y are as defined above and m is 0, with a suitable organic or inorganic oxidising agent, e.g. a peroxy acid, such as 3-chloroperoxybenzoic acid, peracetic acid or hydrogen peroxide, or a permanganate, such as potassium permanganate, an alkoxyperoxide or a periodate, such as sodium periodate, or a dioxirane, such as dimethyldioxirane, or a hydroperoxide or hypochlorite, such as sodium hypochlorite, optionally in the presence of a base, e.g. an alkali metal carbonate, such as potassium carbonate, optionally in the presence of a phase transfer catalyst, such as tetrabutylammonium bromide or triethylbenzyl ammonium chloride, and in the presence of a solvent, e.g. an alcohol, such as methanol or ethanol, acetone, water, a halogenated hydrocarbon, such as dichloromethane or chloroform, or mixtures thereof, in a temperature range from $-20°$ C. to $100°$ C., preferably from $-20°$ C. to $50°$ C. Such processes are known in the literature and described, for example in Synthesis, 1982, 77-78; Tetrahedron Lett., 1997 (31) 5559-5562; J. Org. Chem., 1979 (44) 2510.

3.1) The compounds of formula I, wherein $R^1$, $R^2$, $R^3$, $R^4$, $R^5$, $R^6$, Q and Y are as defined above, m is 1 and n is 1 can also be prepared by processes known per se, e.g. by reacting a compound of formula Ic

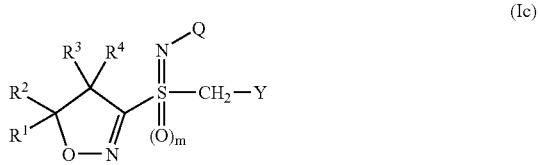
(Ic)

wherein $R^1$, $R^2$, $R^3$, $R^4$, Q and Y are as defined above and m is 1, in a single step or stepwise in succession with compounds of the formula $R^5$—$X^A$ and/or $R^6$—$X^A$, wherein $R^5$ and $R^6$ are as defined above and $X^A$ is a suitable leaving group such as e.g. halogen, such as bromide, a carboxylate, such as acetate, an alkyl- or aryl-sulfonate, such as p-toluene-sulfonate, an imide, such as succinimide, a sulfonimide, such as bis(phenylsulfonyl)-imide, or a haloalkylsulfonate, such as trifluoromethylsulfonate, in the presence of a base, e.g. an alkyl-lithium compound, such as methyl-lithium, n-butyl-lithium and tert-butyl-lithium, a lithium dialkylamide, such as lithium diisopropylamide, a metal hydride, preferably an alkali metal hydride, such as sodium hydride, or an alkali metal amide, such as sodium amide, a metal bis(tri($C_1$-$C_6$alkyl)silyl)amide, such as lithium bis(tri-methylsilyl) amide, a metal alkoxide, such as potassium tert-butoxide, or a phosphazene base, such as N'-tert-butyl-N,N,N',N',N'',N''-hexamethylphosphorimidic triamide ($P_1$-$^t$Bu), 1-ethyl-2,2,4,4-pentakis(dimethylamino)-2-lambda$^5$-5,4-lambda$^5$-5-catena-di(phosphazene) ($P_2$-Et), 1-tert-butyl-2,2,4,4,4-pentakis(dimethylamino)-2-lambda$^5$-5,4-lambda$^5$-5-catenadi(phosphazene) ($P_2$-$^t$Bu), 2-tert-butylimino-2-diethylamino-1,3-di-methyl-perhydro-1,3,2-diazaphosphorine (BEMP) or 2,8,9-triisobutyl-2,5,8,9-tetraaza-1-phosphabicyclo[3.3.3]undecane (Verkade's base), optionally in the presence of a diluent, e.g. N,N-dimethylformamide, an ether, such as tetrahydrofuran (THF) or 1,2-dimethoxy-ethane, or a halogenated hydrocarbon, such as dichloromethane, or mixtures thereof and optionally in the presence of a catalyst, e.g. a phase transfer catalyst, such as tetrabutyl-ammonium bromide or triethylbenzylammonium chloride, or a transition metal catalyst, such as palladium(II) acetate [Pd(OAc)$_2$] or tris(dibenzylideneacetone)dipalladium(0) [Pd$_2$(dba)$_3$], usually in the presence of a phosphine ligand, such as 2,2'-bis(diphenyl-phosphino)-1,1'-binaphthyl (BINAP) or triphenyl phosphine, in a temperature range of from −120° C. to 160° C., preferably from −80° C. to 120° C. Such processes are known in the literature and are described, for example, in Eur. J. Org. Chem. 2003 (8) 1500-1526, J. Org. Chem., 2002 (67) 2859-2863; Tetrahedron Lett. 2000 (41) 2851-2854.

In particular, process 3.1) is useful for the preparation of a compound of formula I wherein $R^1$, $R^2$, $R^3$, $R^4$, Q and Y are as defined above, $R^5$ is halogen, $R^6$ is hydrogen or halogen, m is 1 and n is 1, by halogenation of a compound of formula Ic (see above), wherein $R^1$, $R^2$, $R^3$, $R^4$, Q and Y are defined as above and m is 1, in a single step or stepwise in succession with compounds of formula $R^5$—$X^4$ and/or $R^6$—$X^4$, wherein $R^5$ and/or $R^6$ are halogen, e.g. fluorine, chlorine, bromine and iodine, and $X^4$ is a suitable leaving group as described above. Preferred reagents are N-fluorobenzenesulfonimide (NFSI) or 1-(chloromethyl)-4-fluoro-1,4-diazoniabicyclo[2.2.2]octane bis(tetrafluoro-borate) (SELECTFLUOR) for the fluorination, N-chlorosuccinimide (NCS) or hexa-chloroethane for the chlorination, N-bromosuccinimide (NBS) or phenyl trimethylamino tribromide (PTT) for the bromination, and N-iodosuccinimide (NIS) for the iodination. The halogenations are conveniently carried out in an inert solvent, preferably an ether, e.g. THF, and in the presence of a base, preferably phosphazene bases, e.g. 2-tert-butylimino-2-diethylamino-1,3-dimethyl-perhydro-1,3,2-diazaphosphorine (BEMP), N'-tert-butyl-N,N,N',N',N'',N''-hexamethylphosphorimidic triamide ($P_1$-$^t$Bu), 1-tert-butyl-2,2,4,4,4-pentakis(dimethylamino)-2-lambda$^5$-5,4-lambda$^5$-5-catenadi(phosphazene) ($P_2$-$^t$Bu) or 1-ethyl-2,2,4,4,4-pentakis(dimethylamino)-2-lambda$^5$-5,4 lambda$^5$-5-catena-di(phosphazene) ($P_2$-Et), or 2,8,9-triisobutyl-2,5,8,9-tetraaza-1-phosphabicyclo[3.3.3]un-decane (Verkade's base), in a temperature range from 0° C. to 50° C., preferably from 0° C. to 30° C. Alternatively, the halogenations are carried out in the presence of alkoxide bases, e.g. potassium tert-butoxide, in the presence of a diluent, preferably an ether, e.g. THF, in a temperature range from −100° C. to 50° C., preferably from −80° C. to 0° C. Alternatively, the halogenations are carried out in the presence of an alkyl-lithium compound, e.g. n-butyl lithium, in the presence of a complexing agent, e.g. 1,3-dimethyl-3,4,5,6-tetrahydro-2(1H)-pyrimidinone (DMPU), in the presence of a diluent, preferably an ether, e.g. THF, in a temperature range from −100° C. to 50° C., preferably from −80° C. to 0° C. Alternatively, the halogenations are carried out in the presence of a metal bis(tri($C_1$-$C_6$alkyl)silyl)amide, e.g. sodium bis(trimethylsilyl)amide, in the presence of a diluent, preferably an ether, e.g. THF, in a temperature range from −100° C. to 50° C., preferably from −80° C. to 0° C.

3.2) The compounds of formula I, wherein $R^1$, $R^2$, $R^3$, $R^4$, $R^5$, Q and Y are as defined above, $R^6$ is $C_1$-$C_{10}$alkyl or halogen, m is 1 and n is 1 can also be prepared by processes known per se, e.g. by reacting a compound of formula Id

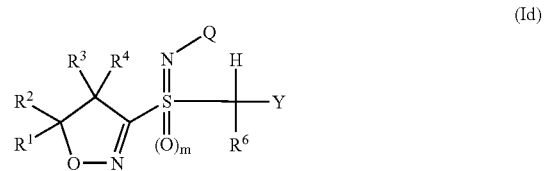

wherein $R^1$, $R^2$, $R^3$, $R^4$, Q and Y are defined as above, $R^6$ is $C_1$-$C_{10}$alkyl, e.g. methyl, or halogen, e.g. chlorine or fluorine, and m is 1 with a compound of formula $R^5$—$X^4$, wherein $R^5$ is as defined above, and $X^4$ is suitable leaving group as described above, in the presence of a base, optionally in the presence of a diluent, preferably an inert solvent, and optionally in the presence of a complexing agent in a temperature range of from −120° C. to 100° C., preferably from −80° C. to 50° C.

In particular, process 3.2) is useful for the preparation of a compound of formula I wherein $R^1$, $R^2$, $R^3$, $R^4$, Q and Y are as defined above, $R^5$ is halogen, $R^6$ is $C_1$-$C_{10}$alkyl or halogen, m is 1 and n is 1, by halogenation of a compound of formula Id (see above) wherein $R^1$, $R^2$, $R^3$, $R^4$, Q and Y are defined as above, $R^6$ is $C_1$-$C_{10}$alkyl, e.g. methyl, or halogen, e.g. chlorine or fluorine, and m is 1 with a compound of formula $R^5$—$X^4$, wherein $R^5$ is halogen, e.g. fluorine, chlorine, bromine and iodine, and $X^4$ is a suitable leaving group as described above. Preferred reagents are N-fluorobenzenesulfonimide (NFSI) or 1-(chloromethyl)-4-fluoro-1,4-diazoniabicyclo[2.2.2]octane bis(tetrafluoroborate) (SELECTFLUOR) for the fluorination, N-chlorosuccinimide (NCS) or hexachloroethane for the chlorination, N-bromosuccinimide (NBS) or phenyl trimethylamino tribromide (PTT) for the bromination and N-iodosuccinimide (NIS) for the iodination. The halogenations are conveniently carried out in an inert solvent, preferably an ether, e.g. THF, and in the presence of a base, preferably phosphazene bases, e.g. 2-tert-butylimino-2-diethylamino-1,3-dimethyl-perhydro-1,3,2-diazaphosphorine (BEMP), N'-tert-butyl-N,N,N',N',N'',N''-hexamethylphosphorimidic triamide ($P_1$-$^t$Bu), 1-tert-butyl-2,2,4,4,4-pentakis(dimethylamino)-2-lambda$^5$-5,4-lambda$^5$-5-catenadi(phosphazene) ($P_2$-$^t$Bu) or 1-ethyl-2,2,4,4,4-pentakis(dimethylamino)-2-lambda$^5$-5,4-lambda$^5$-5-catenadi(phosphazene) ($P_2$-Et), or 2,8,9-triisobutyl-2,5,8,9-tetraaza-1-phosphabicyclo[3.3.3]undecane (Verkade's base), in a temperature range from 0° C. to 50° C., preferably from 0° C. to 30° C. Alternatively, the halogenations are carried out in the presence of alkoxide bases, e.g. potassium tert-butoxide, in the presence of a diluent, preferably an ether, e.g. THF, in a temperature range from −100° C. to 50° C., preferably from −80° C. to 0° C. Alternatively, the halogenations are carried out in the presence of an alkyl-lithium compound, e.g. n-butyl lithium, in the presence of a complexing agent, e.g. 1,3-dimethyl-3,4,5,6-tetrahydro-2(1H)-pyrimidinone (DMPU), in the presence of a diluent, preferably an ether, e.g. THF, in a temperature range from −100° C. to 50° C., preferably from −80° C. to 0° C. Alternatively, the halogenations are carried out in the presence of a metal bis(tri($C_1$-$C_6$alkyl)silyl)amide, e.g. sodium bis(trimethylsilyl)amide, in the presence of a diluent, preferably an ether, e.g. THF, in a temperature range from −100° C. to 50° C., preferably from −80° C. to 0° C.

Alternatively, compounds of formula II wherein $R^1$, $R^2$, $R^3$, $R^4$, $R^5$, $R^6$ and Y are as defined above, m is 0, and n is 1, can be prepared by reacting a compound of formula VIII wherein $R^5$, $R^6$ and Y are defined as above, and $X^F$ is a leaving group such as halogen e.g. bromide or chloride, or alkylsulfonate, e.g. methylsulfonate, or arylsulfonate, e.g. tosylate, with thiourea, optionally in the presence of a diluent e.g. an alcohol, e.g. ethanol, optionally in the presence of an alkali iodide, e.g. sodium iodide, potassium iodide, in a temperature range of from −30° C. to 100° C., preferably from 0° C. to 80° C., to give an isothiourea intermediate of formula XI, which is reacted with a compound of formula IV defined as above, with thiourea in the presence of an acid, for example a mineral acid such as hydrochloric acid or hydrobromic acid, or sulfuric acid, or an organic acid such as trifluoroacetic acid, and optionally in the presence of a diluent, such as an ether, e.g. 1,4-dioxane, THF, a polar solvent, e.g. water, DMF, or a mixture of solvents, e.g. a mixture of 1,4-dioxane and water, in a temperature range of from 20° C. to 270° C., preferably from 20° C. to 150° C., optionally under microwave irradiation. Such processes are known in the literature and are described, for example, in Buchwald and Neilsen, JACS, 110(10), 3171-3175 (1988); Frank and Smith, JACS, 68, 2103-2104 (1946); Vetter, Syn. Comm., 28, 3219-3233 (1998).

A further method of preparing compounds of formula II wherein $R^1$, $R^2$, $R^3$, $R^4$, $R^5$, $R^6$ and Y are as defined above, m is 0, and n is 1, is to react compound of the formula XII wherein $R^5$, $R^6$ and Y are as defined above,

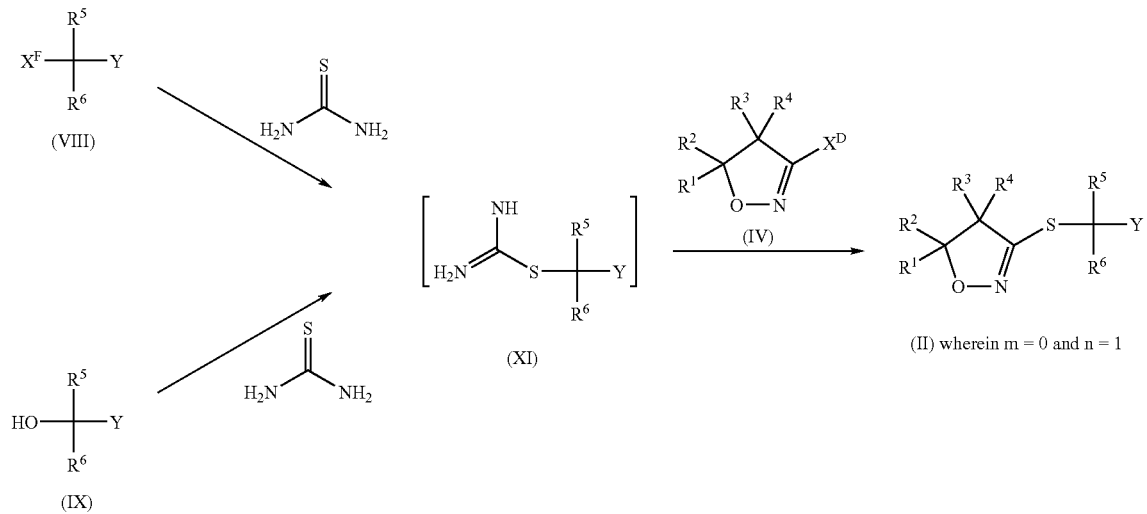

wherein $R^1$, $R^2$ $R^3$ and $R^4$ are defined as above, and $X^D$ is a suitable leaving group such as halogen, e.g. chloride, an alkyl- or aryl-sulfonyl group, e.g. methylsulfonyl or phenylsulfonyl, a haloalkylsulfonyl group, e.g. trifluoromethylsulfonyl, or nitro, in the presence of a base, such as a carbonate, e.g. potassium carbonate, sodium carbonate or potassium bicarbonate, or a hydroxide, e.g. potassium hydroxide, or an alkoxide, e.g. sodium alkoxide, optionally in the presence of a diluent, such as an alcohol, e.g. ethanol, an ether, e.g. 1,4-dioxane, THF, a polar solvent, e.g. water, DMF, or a mixture of solvents, e.g. a mixture of 1,4-dioxane and water, in a temperature range of from 20° C. to 200° C., preferably from 50° C. to 150° C., optionally in the presence of an inert gas e.g. nitrogen, and optionally under microwave irradiation. Such processes are known in the literature and are described, for example, in WO 04/0131106.

A further method of preparing intermediates of formula XI, wherein $R^5$, $R^6$ and Y are as defined above, is to react a compound of the formula IX, wherein $R^5$, $R^6$ and Y are

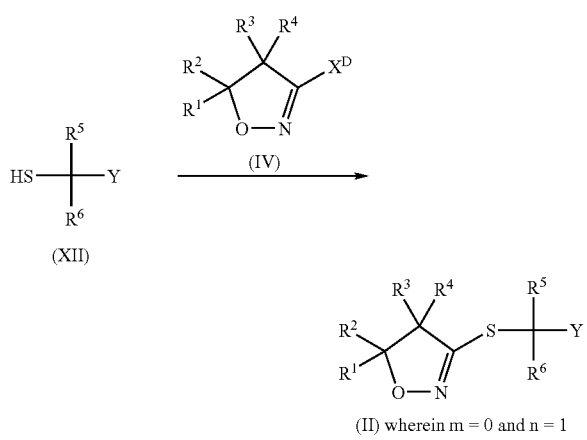

with a compound of formula IV wherein $R^1$, $R^2$, $R^3$ and $R^4$ are defined as above, and $X^D$ is a suitable leaving group such as halogen, e.g. chloride, an alkyl- or aryl-sulfonyl group, e.g. methylsulfonyl or phenylsulfonyl, a haloalkylsulfonyl group, e.g. trifluoromethyl-sulfonyl, or nitro, in the presence of a base, e.g. potassium carbonate, optionally in the presence of a diluent e.g. DMF in a temperature range of from 0° C. to 100° C., preferably from 20° C. to 50° C. and optionally under an inert atmosphere, e.g. nitrogen. Such processes are known in the literature and are described, for example in WO 01/012613, WO 02/062770 and WO 04/010165.

The compounds of formula Ic and Id, wherein $R^1$, $R^2$, $R^3$, $R^4$, $R^6$, Q and Y are as defined above and m is 1 can be prepared as described above.

The compounds of formula I according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxy-propanol, methyl isoamyl ketone; methyl isobutyl ketone, methyl laurate, methyl octanoate, methyl oleate, methylene chloride, m-xylene, n-hexane, n-octylamine, octa-decanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77® and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in US-A-4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula I and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula I may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula I according to the invention are generally applied at a rate of from 10 to 2000 g/ha, especially from 50 to 1000 g/ha.

Preferred formulations have especially the following compositions (%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |

| Dusts: | |
|---|---|
| active ingredient: | 0.1 to 10%, preferably 0.1 to 5% |
| solid carrier: | 99.9 to 90%, preferably 99.9 to 99% |

| Suspension concentrates: | |
|---|---|
| active ingredient: | 5 to 75%, preferably 10 to 50% |
| water: | 94 to 24%, preferably 88 to 30% |
| surface-active agent: | 1 to 40%, preferably 2 to 30% |

| Wettable powders: | |
|---|---|
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

| Granules: | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

Formulation Examples for Herbicides of Formula I (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention relates also to a method for the selective control of grasses and weeds in crops of useful plants, wherein the useful plants or the area of cultivation or locus thereof is treated with the compounds of formula I.

Useful plant crops in which the composition according to the invention can be used include especially maize, soybeans, cotton, cereals, e.g. wheat and barley, rice, sugar cane, sugar beet, sunflowers and rape. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names Roundup Ready® and LibertyLink®. The weeds to be controlled may be both monocotyledonous and dicotyledonous weeds, for example *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate. Crops are also to be understood as being those which are obtained by conventional methods of breeding or genetic engineering and contain so-called output traits (e.g. improved storage stability, higher nutritional value and improved flavour).

Areas under cultivation include land on which the crop plants are already growing and land intended for cultivation with those crop plants.

The compounds of formula I according to the invention can also be used in combination with one or more other herbicides. In particular, the following mixtures of the compound of formula I are important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate; compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosulfaron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula I may also be in the form of esters or salts, as mentioned e.g. in The Pesticide Manual, 12th Edition (BCPC), 2000.

The mixing ratio of the compound of formula I to the mixing partner is preferably from 1:100 to 1000:1.

The mixtures can advantageously be used in the above-mentioned formulations (in which case "active ingredient" relates to the respective mixture of compound of formula I with the mixing partner).

Preferred mixtures of a compound of formula I with one or more further herbicides include:

Mixtures of a compound of the formula I with a triazine (e.g. compound of formula I+ametryn, compound of formula I+atrazine, compound of formula I+cyanazine, compound of formula I+dimethametryn, compound of formula I+metribuzin, compound of formula I+prometon, compound of formula I+prometryn, compound of formula I+propazine, compound of formula I+simazine, compound of formula I+simetryn, compound of formula I+terbumeton, compound of formula I+terbuthylazine, compound of formula I+terbutryn, compound of formula I+trietazine). Particularly preferred are mixtures of a compound of formula I with atrazine, metribuzin, prometryn or with terbuthylazine (i.e. compound of formula I+atrazine, compound of formula I+metribuzin, compound of formula I+prometryn, and compound of formula I+terbuthylazine).

Mixtures of a compound of formula I with isoxaflutole.

Mixtures of a compound of formula I with isoxaflutole and a triazine.

Mixtures of a compound of formula I with isoxaflutole and glyphosate.

Mixtures of a compound of formula I with isoxaflutole and glufosinate.

Mixtures of a compound of formula I with mesotrione.

Mixtures of a compound of formula I with mesotrione and a triazine.

Mixtures of a compound of formula I with mesotrione and glyphosate.

Mixtures of a compound of formula I with mesotrione and glufosinate.

Mixtures of a compound of formula I with sulcotrione.

Mixtures of a compound of formula I with sulcotrione and a triazine.

Mixtures of a compound of formula I with sulcotrione and glyphosate.

Mixtures of a compound of formula I with sulcotrione and glufosinate.

Mixtures of a compound of formula I with a triazolinone (e.g. compound of formula I+amicarbazone).

Mixtures of a compound of formula I with an ALS inhibitor (e.g. compound of formula I+chlorsulfuron, compound of formula I+cinosulfuron, compound of formula I+cloransulam, compound of formula I+ethametsulfuron, compound of formula I+flazasulfuron, compound of formula I+foramsulfuron, compound of formula I+flumetsulam, compound of formula I+imazamethabenz, compound of formula I+imazamox, compound of formula I+imazapic, compound of formula I+imazapyr, compound of formula I+imazethapyr, compound of formula I+iodosulfuron, compound of formula I+metsulfuron, compound of formula I+nicosulfuron, compound of formula I+oxasulfuron, compound of formula I+primisulfuron, compound of formula I+prosulfuron, compound of formula I+pyrithiobac, compound of formula I+rimsulfuron, compound of formula I+sulfosulfuron, compound of formula I+thifensulfuron, compound of formula I+triasulfuron, compound of formula I+tribenuron, compound of formula I+trifloxysulfuron, compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636)). Particularly preferred are mixtures of a compound of formula I with flazasulfuron, foramsulfuron, flumetsulam, imazapyr, imazethapyr, iodosulfuron, nicosulfuron, rimsulfuron, trifloxysulfuron or with 4-[(4,5-dihydro-3-methoxy-4-methyl-5-oxo)-1H-1,2,4-triazol-1-ylcarbonylsulfamoyl]-5-methylthiophene-3-carboxylic acid (BAY636) (i.e. compound of formula I+flazasulfuron, compound of formula I+foramsulfuron, compound of formula I+flumetsulam, compound of formula I+imazapyr, compound of formula I+imazethapyr, compound of formula I+iodosulfuron, compound of formula I+nicosulfuron, compound of formula I+rimsulfuron, compound of formula I+trifloxysulfuron, and compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636)).

Mixtures of a compound of formula I with a PPO inhibitor (e.g. compound of formula I+fomesafen, compound of formula I+flumioxazin, compound of formula I+sulfentrazone, compound of formula I+[3-[2-chloro-4-fluoro-5-(1-methyl-6-trifluoro-methyl-2,4-dioxo-1,2,3,4-tetrahydropyrimidin- 3-yl)phenoxy]-2-pyridyloxy]acetic acid ethyl ester). Particularly preferred are mixtures of a compound of formula I with flumioxazin, sulfentrazone or [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (i.e. compound of formula I+flumioxazin, compound of formula I+sulfentrazone, and compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy] acetic acid ethyl ester).

Mixtures of a compound of formula I with glyphosate.
Mixtures of a compound of formula I with glufosinate.
Mixtures of a compound of formula I with paraquat.
Mixtures of a compound of formula I with pendimethalin or a compound of formula I with trifluralin. Particularly preferred are mixtures of a compound of formula I with pendimethalin.
Mixtures of a compound of formula I with metamitron.
Mixtures of a compound of formula I with clomazone.
Mixtures of a compound of formula I with metazachlor.
Mixtures of a compound of formula I with clodinafop or a compound of formula I with pinoxaden.

The compounds of formula I according to the invention can also be used in combination with safeners. Likewise, mixtures of a compound of formula I according to the invention with one or more further herbicides can also be used in combination with one or more safeners. The safeners can be cloquintocet-mexyl (CAS RN 99607-70-2) or a lithium, sodium, potassium, calcium, magnesium, aluminium, iron, ammonium, quaternary ammonium, sulfonium or phosphonium salt thereof such as those disclosed in WO 02/34048, fenchlorazol-ethyl (CAS RN 103112-35-2) and the corresponding acid (CAS RN 103112-36-3), mefenpyr-diethyl (CAS RN 135590-91-9) and the corresponding di-acid (CAS RN 135591-00-3), isoxadifen-ethyl (CAS RN 163520-33-0) and the corresponding acid (CAS RN 209866-92-2), furilazole (CAS RN 121776-33-8) and the corresponding R isomer (CAS RN 121776-57-6), benoxacor (CAS RN 98730-04-2), dichlormid (CAS RN 37764-25-3), MON4660 (CAS RN 71526-07-3), oxabetrinil (CAS RN 74782-23-3), cyometrinil (CAS RN 78370-21-5) and the corresponding (Z) isomer (CAS RN 63278-33-1), fenclorim (CAS RN 3740-92-9), N-cyclopropyl-4-(2-methoxy-benzoylsulfamoyl)-benzamide (CAS RN 221667-31-8), N-isopropyl-4-(2-methoxybenzoylsulfamoyl)-benzamide (CAS RN 221668-34-4), naphthalic anhydride (CAS RN 81-84-5) and flurazole (CAS RN 72850-64-7).

Preferably the mixing ratio of compound of formula I to safener is from 100:1 to 1:10, especially from 20:1 to 1:1.

The mixtures can advantageously be used in the above-mentioned formulations (in which case "active ingredient" relates to the respective mixture of compound of formula I with the safener).

Preferred mixtures of a compound of formula I with further herbicides and safeners include:

Mixtures of a compound of formula I with a triazine and a safener.
Mixtures of a compound of formula I with glyphosate and a safener.
Mixtures of a compound of formula I with glufosinate and a safener.
Mixtures of a compound of formula I with isoxaflutole and a safener.
Mixtures of a compound of formula I with isoxaflutole and a triazine and a safener.
Mixtures of a compound of formula I with isoxaflutole and glyphosate and a safener.
Mixtures of a compound of formula I with isoxaflutole and glufosinate and a safener.
Mixtures of a compound of formula I with mesotrione and a safener.
Mixtures of a compound of formula I with mesotrione and a triazine and a safener.
Mixtures of a compound of formula I with mesotrione and glyphosate and a safener.
Mixtures of a compound of formula I with mesotrione and glufosinate and a safener.
Mixtures of a compound of formula I with sulcotrione and a safener.
Mixtures of a compound of formula I with sulcotrione and a triazine and a safener.
Mixtures of a compound of formula I with sulcotrione and glyphosate and a safener.
Mixtures of a compound of formula I with sulcotrione and glufosinate and a safener.

The following Examples further illustrate, but do not limit, the invention.

PREPARATION EXAMPLES

Example P1

Preparation of 3-{2,6-difluoro-phenylmethane(N-trifluoromethyl-carbonyl)sulfoximinyl)-5,5-dimethyl-4,5-dihydroisoxazole

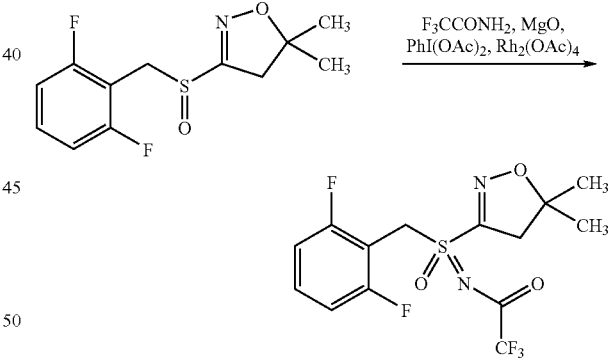

Trifluoroacetamide (356 mg, 3.15 mmol), magnesium oxide (254 mg, 6.3 mmol), rhodium(II) acetate dimer (17.4 mg, 0.04 mmol) and iodobenzene diacetate (761 mg, 2.36 mmol) was added to a solution of 3-(2,6-difluoro-phenylmethanesulfinyl)-5,5-dimethyl-4,5-dihydroisoxazole (430 mg, 1.58 mmol) in dichloromethane (16 ml) under nitrogen and the dark green solution was stirred for 12 hours at room temperature. The mixture was filtered through celite, the celite was washed with dichloromethane and the filtrate was concentrated. The crude product was purified by chromatography on silica gel (eluent: hexane/ethyl acetate) to give the product (Compound No. 1.04 of Table 65) as yellow solid (282 mg, 47% yield).

The following compounds were synthesised as described in Example P1:

Compound No. 1.11 of Table 65 using 4-nitrophenylsulfonamide as reagent,

Compound No. 1.12 of Table 65 using methylsulfonamide as reagent,

Compound No. 1.06 of Table 65 using carbamic acid tert.-butylester as reagent

Compound No. 2.02 of Table 66 using 3-(5-chloro-1-methyl-3-trifluoromethyl-1H-pyrazol-4-ylmethanesulfinyl)-5,5-dimethyl-4,5-dihydroisoxazole as starting material, Compound No. 2.05 of Table 66 using 3-(1-methyl-3-trifluoromethyl-1H-pyrazol-4-ylmethanesulfinyl)-5,5-dimethyl-4,5-dihydroisoxazole, and Compound No. 2.08 of Table 66 using 3-(3-difluoromethyl-1-methyl-1H-pyrazol-4-yl-methanesulfinyl)-5,5-dimethyl-4,5-dihydroisoxazole.

Example P2

Preparation of 3-{2,6-difluoro-phenylmethane-sulfoximinyl-5,5-dimethyl-4,5-dihydroisoxazole

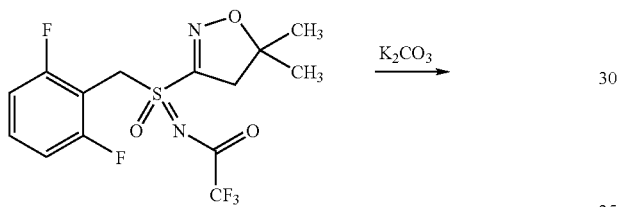

Potassium carbonate (77 mg, 0.56 mmol) was added to 3-{2,6-difluoro-phenyl-methane(N-trifluoromethylcarbonyl)-sulfoximinyl)-5,5-dimethyl-4,5-dihydroisoxazole (Compound No. 1.04 of Table 65) (194 mg, 0.51 mmol) in methanol (0.2 ml). After 15 minutes the mixture was concentrated and partitioned between dichloromethane and water. The organic phase was washed with brine, dried over magnesium sulfate and concentrated to give a pale yellow gum that solidified upon standing to give the product (Compound 1.01 of Table 65) as cream solid (133 mg, 98% yield).

The following compounds were synthesised as described in Example P2:

Compound No. 1.02 of Table 65 from Compound No. 1.05 of Table 65,

Compound No. 1.22 of Table 65 from Compound No. 1.38 of Table 65,

Compound No. 1.52 of Table 65 from Compound No. 1.50 of Table 65,

Compound No. 1.53 of Table 65 from Compound No. 1.51 of Table 65,

Compound No. 2.01 of Table 66 from Compound No. 2.02 of Table 66,

Compound No. 2.06 of Table 66 from Compound No. 2.05 of Table 66, and

Compound No. 2.07 of Table 66 from Compound No. 2.08 of Table 66.

The following compound was synthesised as described in Example P11 followed by the procedure described in Example P2:

Compound No. 1.56 of Table 65 from 3-{3-trifluoromethoxyphenylmethane(N-[4-nitrobenzoyl])-sulfoximinyl)-5,5-dimethyl-4,5-dihydroisoxazole.

The following compound was synthesised as described in Example P12 followed by the procedure described in Example P2:

Compound No. 1.57 of Table 65 from 3-{3-trifluoromethoxyphenylmethane(N-[4-nitrobenzoyl])-sulfoximinyl)-5,5-dimethyl-4,5-dihydroisoxazole.

Compound No. 2.03 of Table 66 from 3-{5-methoxy-1-methyl-3-trifluoromethyl-1H-pyrazol-4-ylmethane(N-[4-nitrobenzoyl])-sulfoximinyl)-5,5-dimethyl-4,5-dihydroisoxazole.

The following compound was synthesised as described in Example P1 followed by the procedure described in Example P2: Compound No. 2.04 of Table 66 from 3-(3-difluoromethoxy-1-methyl-5-trifluoromethyl-1H-pyrazol-4-yl-methanesulfinyl)-5,5-dimethyl-4,5-dihydro-isoxazole.

Example P3

Preparation of 3-{2,6-difluoro-phenylmethane(N-methyl)sulfoximinyl)-5,5-dimethyl-4,5-dihydroisoxazole

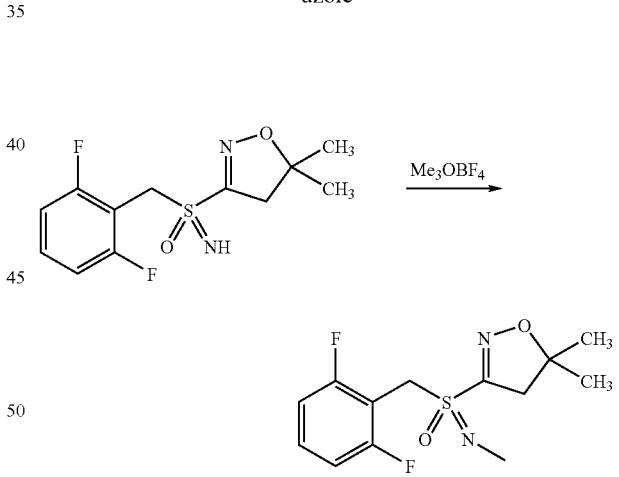

A solution of 3-{2,6-difluoro-phenylmethanesulfoximinyl)-5,5-dimethyl-4,5-dihydroisoxazole (Compound No. 1.01 of Table 65) (50 mg, 0.17 mmol) in dichloro-methane (0.2 ml) was added dropwise to a suspension of trimethyloxonium tetrafluoro-borate (26 mg, 0.17 mmol) in dichloromethane (0.5 ml) under nitrogen. After 12 hours at room temperature, the mixture was washed with sodium bicarbonate, the aqueous phase was extracted several times with dichloromethane. The combined organic phases were dried over magnesium sulfate and concentrated. The crude product was purified by chromatography on silica gel (eluent: hexane/ethyl acetate) to give the product (Compound 1.08 of Table 65) as a white solid (15 mg, 29% yield).

Example P4

Preparation of 3-{2,6-difluoro-phenylmethane(N-[4-chlorobenzoyl]-sulfoximinyl)-5,5-dimethyl-4,5-dihydroisoxazole

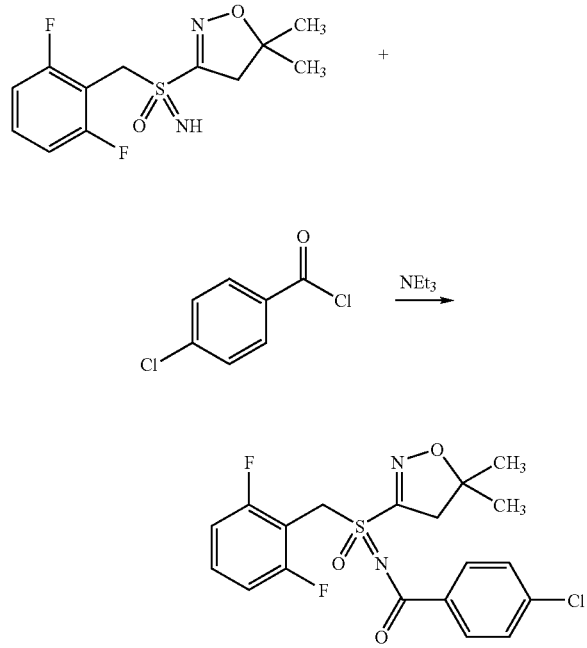

Triethylamine (0.76 ml, 5.5 mmol) and 4-chlorobenzoyl chloride (0.53 ml, 5.2 mmol) were added dropwise to 3-{2,6-difluoro-phenylmethanesulfoximinyl)-5,5-dimethyl-4,5-dihydroisoxazole (Compound No. 1.01 of Table 65) (1.2 g, 4.2 mmol) in dichloromethane (10 ml) at 0° C. under nitrogen. The mixture was stirred for 1 hour at 0° C. and for 10 hours at room temperature, poured into water and extracted several times with dichloromethane. The combined organic phases were dried over magnesium sulfate, concentrated and purified by chromatography on silica gel (eluent: hexane/ethyl acetate) to give the product (Compound No. 1.03 of Table 65) as a white solid (540 mg, 53% yield).

The following compounds were synthesised as described in Example P4:
- Compound No. 1.07 of Table 65 using acetyl chloride as reagent,
- Compound No. 1.17 of Table 65 using 1-chloroethyl chloroformate as reagent,
- Compound No. 1.21 of Table 65 using 2-chloronicotinoyl chloride as reagent,
- Compound No. 1.36 of Table 65 using benzoyl chloride as reagent, and
- Compound No. 1.45 of Table 65 using 4-nitrobenzoyl chloride as reagent.

Example P5

Preparation of 3-{2,6-difluoro-phenylmethane(N-[trimethylsilyl]-sulfoximinyl)-5,5-dimethyl-4,5-dihydroisoxazole

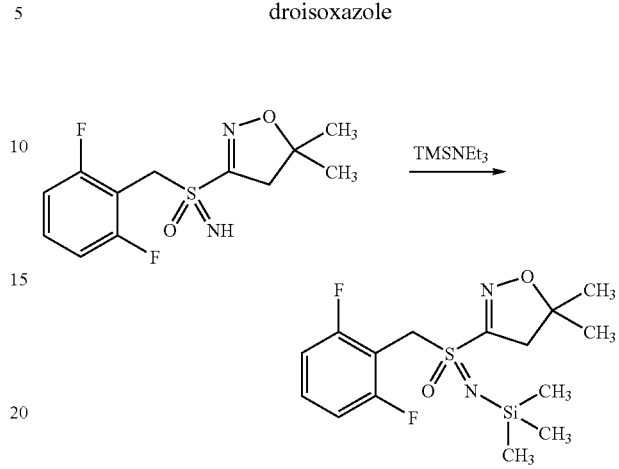

N,N-Diethyltrimethylsilylamine (0.07 ml, 0.39 mmol) was added dropwise to a solution of 3-{2,6-difluoro-phenylmethanesulfoximinyl)-5,5-dimethyl-4,5-dihydro-isoxazole (Compound No. 1.01 of Table 65) (100 mg, 0.35 mmol) in acetonitrile (2 ml) at 65° C. under nitrogen. After stirring for 1.5 hours at 65° C. and for 10 hours at room temperature the mixture was concentrated to give the product (Compound No. 1.10 of Table 65) as a pale orange gum (117 mg, purity 80%).

Example P6

Preparation of 3-{2,6-difluoro-phenyl-chloromethane(N-[trifluoroacetyl]-sulfoximinyl)-5,5-dimethyl-4,5-dihydroisoxazole

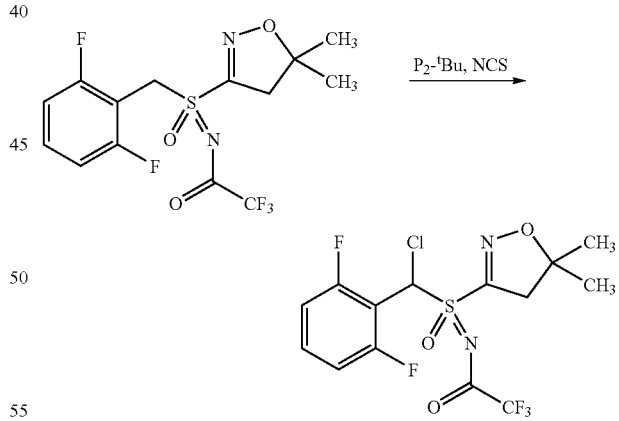

1-tert-Butyl-2,2,4,4,4-pentakis(dimethylamino)-2-lambda$^5$-5,4-lambda$^5$-5-catena-di(phosphazene) (P$_2$-$^t$Bu) (2M in THF) (0.14 ml, 0.29 mmol) was added to a solution of 3-{2,6-difluoro-phenylmethane(N-trifluoromethylcarbonyl)sulfoximinyl)-5,5-dimethyl-4,5-dihydroisoxazole (Compound No. 1.04 of Table 65) (100 mg, 0.26 mmol) in THF (3 ml) under nitrogen. After 10 minutes N-chlorosuccinimide (NCS) (38 mg, 0.29 mmol) was added and the mixture stirred for 10 minutes. The mixture was poured into aqueous hydrochloric acid (1M) and extracted several times with ethyl acetate. The combined organic phases were dried over magnesium sulfate, concentrated and purified by chromatography on silica gel (eluent: hexane/ethyl acetate) to give the product (Compound No. 1.05 of Table 65) as a white solid (50 mg, 46% yield).

Example P7

Preparation of 3-{2,6-difluoro-phenyl-methane(N-[formyl]sulfoximinyl)-5,5-dimethyl-4,5-dihydroisoxazole

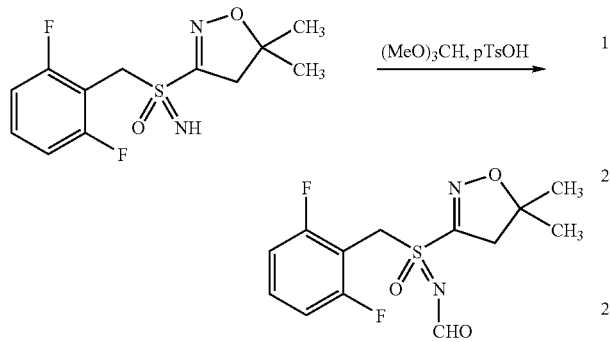

3-{2,6-Difluoro-phenylmethanesulfoximinyl)-5,5-dimethyl-4,5-dihydroisoxazole (Compound No. 1.01 of Table 65) (100 mg, 0.35 mmol) and a catalytic amount of p-toluenesulfonic acid was dissolved in trimethyl orthoformate (1 ml) and heated to 90° C. for 3.5 hours. The mixture was cooled to room temperature, concentrated and the crude product was purified by chromatography on silica gel (eluent: hexane/ethyl acetate) to give the product (Compound No. 1.13 of Table 65) (8 mg, 11% yield).

Example P8

Preparation of 3-{2,6-difluoro-phenyl-methane(N-[nitro]sulfoximinyl)-5,5-dimethyl-4,5-dihydroisoxazole

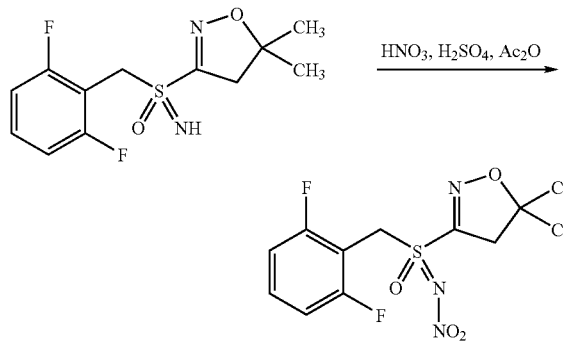

3-{2,6-Difluoro-phenylmethanesulfoximinyl)-5,5-dimethyl-4,5-dihydroisoxazole (Compound No. 1.01 of Table 65) (100 mg, 0.35 mmol) was dissolved in dichloro-methane (0.7 ml) and fuming nitric acid (15 μl, 0.35 mmol) was added. After 10 minutes the mixture was cooled to 0° C. and acetic anhydride (0.7 ml, 7.29 mmol) and 1 drop of concentrated sulfuric acid were added. The mixture was stirred for 20 minutes at 0° C. and for 1.5 hours at room temperature, was diluted with ethyl acetate and washed several times with water and saturated aqueous sodium bicarbonate solution. The aqueous phase was extracted with ethyl acetate, the combined organic phases were washed again with water, dried over magnesium sulfate and concentrated. Trituration with n-hexane furnished the product (Compound No. 1:15 of Table 65) (54.8 mg, 47% yield).

Example P9

Preparation of 3-{2,6-difluoro-phenyl-methane(N-[trifluoroacetyl]-sulfiliminyl)-5,5-dimethyl-4,5-dihydroisoxazole

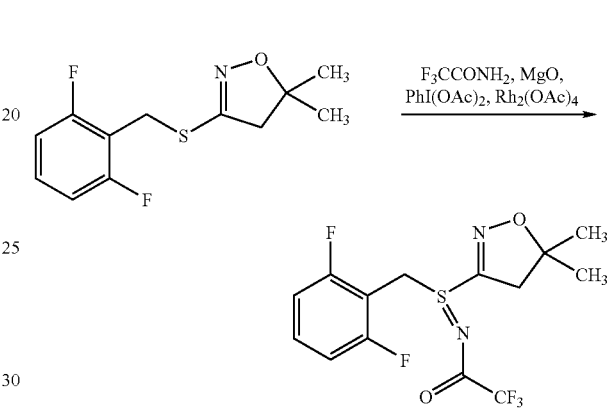

Trifluoroacetamide (4.4 g, 38.9 mmol), magnesium oxide (3.1 g, 77.7 mmol), rhodium(II) acetate dimer (217 mg, 0.49 mmol) and iodobenzene diacetate (9.4 g, 29.1 mmol) were added to a solution of 3-(2,6-difluoro-phenylmethanesulfanyl)-5,5-dimethyl-4,5-dihydroisoxazole (5 g, 19.4 mmol) in dichloromethane (150 ml) under nitrogen and the grey suspension was stirred for 12 hours at room temperature. The mixture was filtered and the filtrate was concentrated. The crude product was purified by chromatography on silica gel (eluent: hexane/ethyl acetate) to give the product (Compound No. 1.09 of Table 65) (6.7 g, 90% purity, 84% yield).

Example P10

Preparation of 3-{2,6-difluoro-phenylmethane-sulfoximinyl-5,5-dimethyl-4,5-dihydroisoxazole

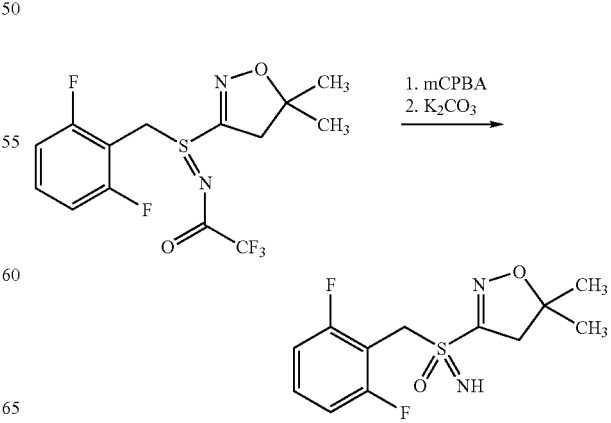

Potassium carbonate (5.3 g, 38.4 mmol) in water (13 ml) was added to a solution of 3-{2,6-difluoro-phenylmethane (N-trifluoromethylcarbonyl)sulfilimyl)-5,5-dimethyl-4,5-dihydrisoxazole (Compound No. 1.09 of Table 65) (6.7 g, 18.3 mmol) in ethanol (90 ml). A solution of m-chloroperoxybenzoic acid (50-70% weight) (8.84 g, 30.7 mmol) in ethanol (30 ml) was added dropwise and the mixture stirred for 1 hour at room temperature. The reaction was quenched by addition of 40% aqueous metabisulfite solution (50 ml). The mixture was stirred for 10 minutes before it was extracted several times with ethyl acetate. The combined organic phases were washed with saturated aqueous sodium bicarbonate and brine, dried over magnesium sulfate and concentrated to give the product (Compound No. 1.01 of Table 65) as a white solid (3.7 g, 70% yield).

The following compounds were synthesised as described in Example P9 followed by the procedure described in Example P10:

Compound No. 1.24 of Table 65 from 3-(2-trifluoromethoxy-phenylmethanesulfanyl)-5,5-dimethyl-4,5-dihydroisoxazole, Compound No. 1.25 of Table 65 from 3-(2-difluoromethoxy-phenylmethanesulfanyl)-5,5-dimethyl-4,5-dihydroisoxazole, Compound No. 1.26 of Table 65 from 3-(2-trifluoromethylthio-phenylmethanesulfanyl)-5,5-dimethyl-4,5-dihydroisoxazole, Compound No. 1.27 of Table 65 from 3-(2-tolyl-methanesulfanyl)-5,5-dimethyl-4,5-dihydroisoxazole, Compound No. 1.28 of Table 65 from 3-(2,6-difluoro-3-tolylmethanesulfanyl)-5,5-dimethyl-4,5-dihydroisoxazole, Compound No. 1.29 of Table 65 from 3-(2,3-difluoro-phenylmethanesulfanyl)-5,5-di-methyl-4,5-dihydroisoxazole, Compound No. 1.30 of Table 65 from 3-(2,4-difluoro-phenylmethanesulfanyl)-5,5-dimethyl-4,5-dihydroisoxazole, Compound No. 1.31 of Table 65 from 3-(2-trifluoromethyl-phenylmethanesulfanyl)-5,5-dimethyl-4,5-dihydro-isoxazole, Compound No. 1.32 of Table 65 from 3-(2-fluoro-6-trifluoromethylphenyl-methanesulfanyl)-5,5-dimethyl-4,5-dihydroisoxazole, Compound No. 1.33 of Table 65 from 3-(2-biphenylmethanesulfanyl)-5,5-dimethyl-4,5-dihydroisoxazole, Compound No. 1.34 of Table 65 from 3-(2,5-difluoro-phenylmethanesulfanyl)-5,5-dimethyl-4,5-dihydroisoxazole, Compound No. 1.39 of Table 65 from 3-(2-fluoro-phenylmethanesulfanyl)-5,5-dimethyl-4,5-dihydroisoxazole, Compound No. 1.40 of Table 65 from 3-(3,5-difluoro-phenylmethanesulfanyl)-5,5-dimethyl-4,5-dihydro-isoxazole, Compound No. 1.41 of Table 65 from 3-(2-cyano-phenylmethanesulfanyl)-5,5-dimethyl-4,5-dihydroisoxazole, Compound No. 1.42 of Table 65 from 3-phenyl-methanesulfanyl-5,5-dimethyl-4,5-dihydroisoxazole, Compound No. 1.46 of Table 65 from 3-(2-fluoro-4-methoxycarbonyl-phenylmethanesulfanyl)-5,5-dimethyl-4,5-dihydro-isoxazole, Compound No. 1.47 of Table 65 from 3-(4-ethoxycarbonyl-2-fluoro-phenyl-methanesulfanyl)-5,5-dimethyl-4,5-dihydroisoxazole, Compound No. 1.48 of Table 65 from 3-(6-fluoro-4H-benzo[1,3]dioxin-8-yl methanesulfanyl)-5,5-dimethyl-4,5-dihydroisoxazole, Compound No. 1.49 of Table 65 was isolated during the synthesis of Compound No. 1.48 of Table 65, Compound No. 1.59 of Table 65 from 3-(2-chloro-3-ethoxycarbonyl-6-methylsulfonyl-phenylmethanesulfanyl)-5,5-dimethyl-4,5-dihydroisoxazole.

Example P11

Preparation of 3-{2,6-difluoro-phenylfluoromethane (N-[4-nitrobenzoyl]-sulfoximinyl)-5,5-dimethyl-4,5-dihydroisoxazole

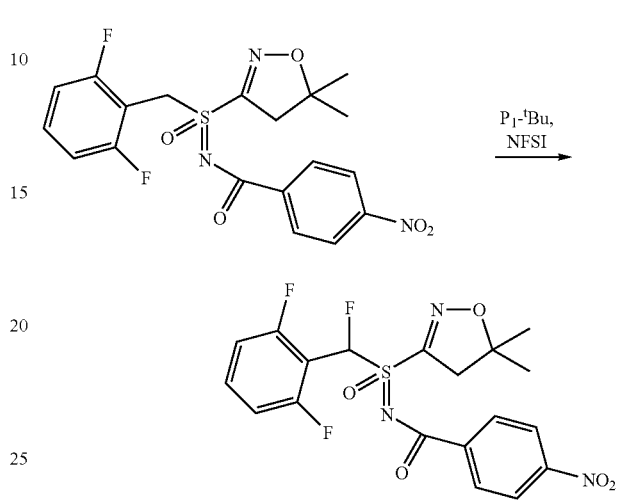

To a solution of 3-{2,6-difluoro-phenylmethane(N-[4-nitrobenzoyl]sulfoximinyl)-5,5-dimethyl-4,5-dihydroisoxazole (Compound No. 1.45 of Table 65) (500 mg, 1.14 mmol) in THF (5 ml) was added N'-tert-butyl-N,N,N',N',N'',N''-hexamethyl-phosphorimidic triamide ($P_1$-$^t$Bu) (0.31 ml, 1.2 mmol) dropwise. After 10 minutes N-fluorobenzenesulfonimide (NFSI) (378 mg, 2.58 mmol) was added and the mixture stirred for 5 hours. The mixture was concentrated and purified by chromatography on silica gel (eluent: hexane/ethyl acetate) to give diastereomer A (Compound No. 1.50 of Table 65) as a white solid (340 mg, 65% yield) and diastereomer B (Compound No. 1.51 of Table 65) as a white solid (103 mg, 20% yield).

The following compounds were synthesised as described in Example P11:

Compound No. 1.35 of Table 65 from Compound No. 1.36 of Table 65, and

Compound No. 1.43 of Table 65 from Compound No. 1.03 of Table 65.

Example P12

Preparation of 3-{2,6-difluoro-phenyldifluoromethane(N-[benzoyl]-sulfoximinyl)-5,5-dimethyl-4,5-dihydroisoxazole

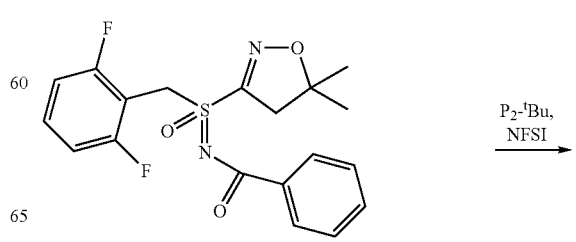

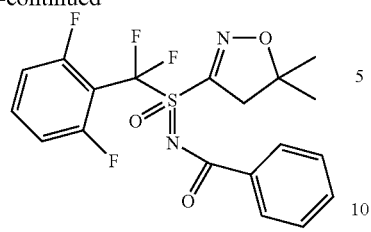

To a solution of 3-{2,6-difluoro-phenylmethane(N-[benzoyl]sulfoximinyl)-5,5-dimethyl-4,5-dihydroisoxazole (Compound No. 1.36 of Table 65) (155 mg, 0.39 mmol) in THF (5 ml) was added 1-tert-butyl-2,2,4,4,4-pentakis(dimethylamino)-2-lambda$^5$-5,4-lambda$^5$-5-catenadi(phosphazene) (P$_2$-$^t$Bu) (2M in THF) (0.44 ml, 0.87 mmol) dropwise. After 10 minutes N-fluorobenzenesulfonimide (NFSI) (274 mg, 0.87 mmol) was added and the mixture stirred for 30 minutes. The mixture was concentrated and purified by chromatography on silica gel (eluent: hexane/ethyl acetate) to give the product (Compound No. 1.37 of Table 65) as a white solid (94 mg, 56% yield).

Compound No. 1.38 of Table 65 was were synthesised as described in Example P12 from Compound No. 1.45 of Table 65.

Example P13

Preparation of 3-{2,6-difluoro-phenyldifluoromethane(N-[4-chloro-benzoyl]sulfoximinyl)-5,5-dimethyl-4,5-dihydroisoxazole

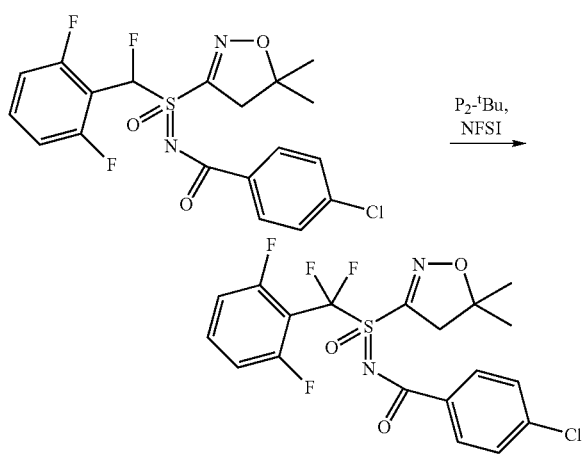

To a solution of 3-{2,6-difluoro-phenylfluoromethane(N-[4-chlorobenzoyl]-sulfoximinyl)-5,5-dimethyl-4,5-dihydroisoxazole (Compound No. 1.43 of Table 65) (450 mg, 1.0 mmol) in THF (5 ml) was added 1-tert-butyl-2,2,4,4,4-pentakis(dimethylamino)-2-lambda$^5$-5,4-lambda$^5$-5-catenadi (phosphazene) (P$_2$-$^t$Bu) (2M in THF) (0.55 ml, 1.1 mmol) dropwise. After 10 minutes N-fluorobenzenesulfonimide (NFSI) (350 mg, 1.1 mmol) was added and the mixture stirred for 30 minutes. The mixture was concentrated and purified by chromatography on silica gel (eluent: hexane/ethyl acetate) to give the product (Compound No. 1.44 of Table 65) as a white solid (200 mg, 53% yield).

Example P14

Preparation of 3-{2,6-difluoro-phenylfluorochloromethanesulfoximinyl-5,5-dimethyl-4,5-dihydroisoxazole

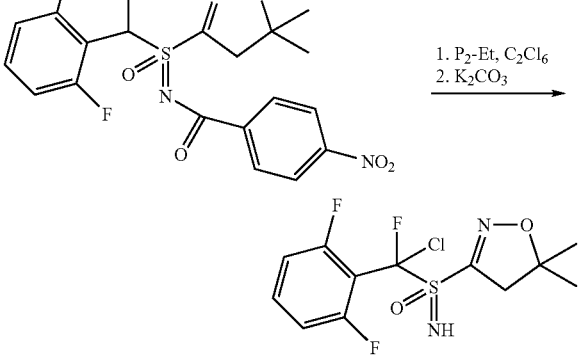

A diastereomeric mixture of 3-{2,6-difluoro-phenylfluoromethane(N-[4-nitrobenzoyl]sulfoximinyl)-5,5-dimethyl-4,5-dihydroisoxazole (Compound No. 1.50 of Table 65 and Compound No. 1.51 of Table 65) (300 mg, 0.66 mmol) and hexachloroethane (172 mg, 0.72 mmol) were dissolved in THF (5 ml) and 1-ethyl-2,2,4,4,4-pentakis(dimethylamino)-2-lambda$^5$-5,4-lambda$^5$-5-catenadi(phosphazene) (P$_2$-Et) (0.24 ml, 0.72 mmol) was added dropwise at 0° C. After 30 minutes several drops of saturated aqueous ammonium chloride solution was added and the mixture was concentrated. The residue was dissolved in methanol (5 ml) and potassium carbonate (100 mg, 0.72 mmol) was added. After 2 hours the mixture was concentrated, the residue dissolved in dichloromethane, washed several times with saturated aqueous sodium bicarbonate solution, and brine, and dried over magnesium sulfate. The mixture was concentrated and purified by chromatography on silica gel (eluent: hexane/ethyl acetate) to give diastereomer A (Compound No. 1.54 of Table 65) as a white solid (27 mg, 12% yield) and diastereomer B (Compound No. 1.55 of Table 65) as a white solid (57 mg, 25% yield).

Example P15

Preparation of 3-{1'-[2,6-difluoro-phenyl]ethane(N-[trifluoroacetyl]-sulfoximinyl)-5,5-dimethyl-4,5-dihydroisoxazole

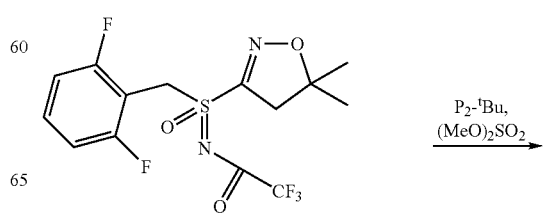

-continued

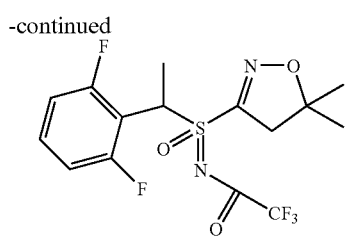

To a solution of 3-{2,6-difluoro-phenylmethane(N-trifluoromethyl-carbonyl)sulfoximinyl)-5,5-dimethyl-4,5-dihydroisoxazole (Compound No. 1.04 of Table 65) (227 mg, 0.59 mmol) in THF (10 m) was added 1-tert-butyl-2,2,4,4,4-pentakis-(dimethylamino)-2-lambda$^5$-5,4-lambda$^5$-5-catenadi (phosphazene) (P$_2$-$^t$Bu) (2M in THF) (0.3 ml, 0.65 mmol) under nitrogen at room temperature. After 5 minutes dimethyl sulfate (109 μL, 0.65 mmol) was added and the mixture stirred for 30 minutes. The reaction was quenched by addition of aqueous hydrochloric acid (2M) (0.5 ml) and extracted with ethyl acetate. The combined organic extracts were washed with brine, dried over magnesium sulfate, filtered through silica gel and concentrated. The residue was purified by preparative HPLC (20% ethyl acetate/hexane) to give diastereomer A (Compound No. 1.19 of Table 65) as a colourless gum (58 mg, 25% yield) and diastereomer B (Compound No. 1.20 of Table 65) as a colourless gum (45 mg, 19% yield).

Example P16

Preparation of 3-{2,6-difluoro-phenylmethane(N-trifluoromethylsulphonyl)-sulfoximinyl)-5,5-dimethyl-4,5-dihydroisoxazole

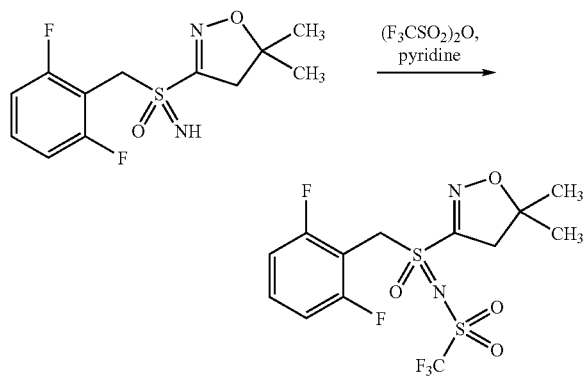

3-{2,6-difluoro-phenylmethanesulfoximinyl)-5,5-dimethyl-4,5-dihydroisoxazole (Compound No. 1.01 of Table 65) (100 mg, 0.35 mmol) and pyridine (0.08 ml, 1.04 mmol) were dissolved in dichloromethane (5 ml) and trifluoromethanesulfonic anhydride (0.09 ml, 0.52 mmol) was added dropwise at 0° C. The mixture was allowed to warm to room temperature and stirred for 4 h. The mixture was diluted with ethyl acetate (10 ml), washed with water (10 ml) and 2M HCl (10 ml), dried over MgSO4 and concentrated. Purification by chromatography on silica gel (eluent: hexane/ethyl acetate) gave the product (Compound No. 1.14 of Table 65) as a colourless gum (78 mg, 53% yield).

Example P17

Preparation of 3-{2,6-difluoro-phenylmethane(N-[4-trifluoromethyl-2-pyrimidyl])-sulfoximinyl)-5,5-dimethyl-4,5-dihydroisoxazole

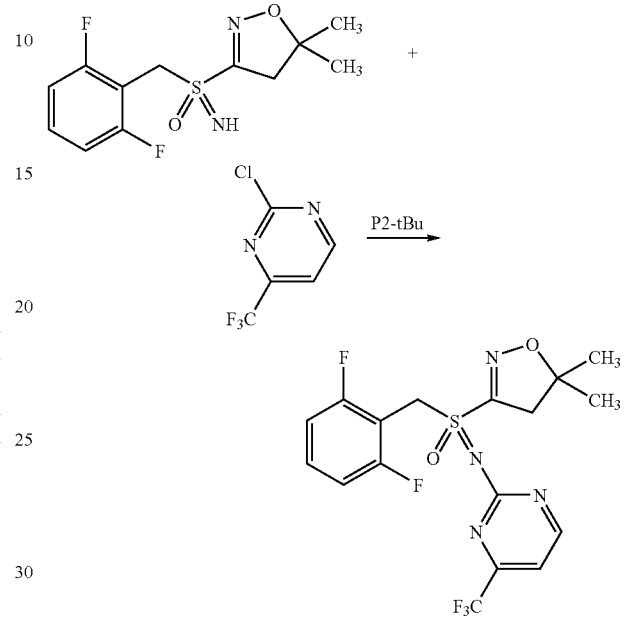

3-{2,6-difluoro-phenylmethanesulfoximinyl)-5,5-dimethyl-4,5-dihydroisoxazole (Compound No. 1.01 of Table 65) (200 mg, 0.69 mmol) was dissolved in tetrahydrofuran (3 ml) and 1-tert-Butyl-2,2,4,4,4-pentakis(dimethylamino)-2-lambda$^5$-5,4-lambda$^5$-5-catenadi(phosphazene) (P$_2$-$^t$Bu) (2M in THF) (0.42 ml, 0.83 mmol) was added dropwise, followed by 2-chloro-4-trifluoromethylpyrimidine (152 mg, 0.83 mmol). The mixture was stirred at room temperature for 24 h, then was heated to reflux for 5 h. After cooling, ethyl acetate (10 ml) was added and the mixture was washed with 2M HCl (10 ml), dried over MgSO$_4$ and concentrated. Purification by chromatography on silica gel (eluent: hexane/ethyl acetate) gave the product (Compound No. 1.16 of Table 65) as a white solid (83 mg, 28% yield).

Compound No. 1.23 of Table 65 was synthesised as described in Example P17 using 4-chloro-5-cyanopyrimidine as reagent,

Example P18

Preparation of 3-{2,6-difluoro-phenyl-methane(N-4-nitrophenylsulphonyl]sulfiliminyl)-5,5-dimethyl-4,5-dihydroisoxazole

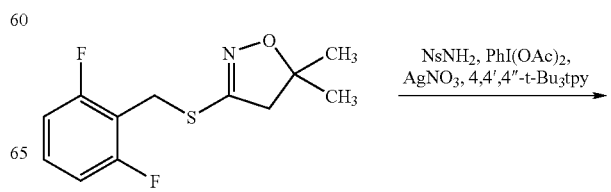

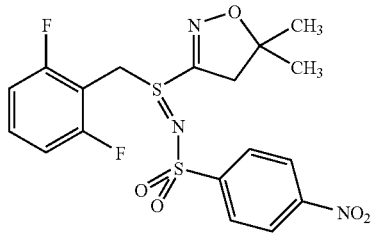

4-Nitrobenzenesulphonamide (189 mg, 0.93 mmol), silver nitrate (11 mg, 0.06 mmol), 4,4',4''-tri-tert-butyl-2,2':6',2''-terpyridine (25 mg, 0.06 mmol) and iodobenzene diacetate (375 mg, 1.17 mmol) were added to a solution of 3-(2,6-difluoro-phenylmethanesulfanyl)-5,5-dimethyl-4,5-dihydroisoxazole (200 mg, 0.8 mmol) in acetonitrile (5 ml) under nitrogen and the resulting dark red solution was stirred for 12 hours at room temperature, then heated for 5 min in a sealed tube to 100° C. in the microwave. The resulting pale yellow solution was concentrated and the crude product was purified by chromatography on silica gel (eluent: hexane/ethyl acetate) to give 3-{2,6-difluoro-phenyl-methane(N-[4-nitro-phenylsulphonyl]sulfiliminyl)-5,5-dimethyl-4,5-dihydroisoxazole as white solid (107 mg, 25% yield).

The compounds mentioned in the following table 65 below can be prepared in analogous manner. One of the compounds (1.18) in Table 65 was prepared by a different route as given in Example P19.

Example P19

Preparation of 3-{2,6-difluoro-phenylmethane(N-ethoxycarbonylmethyl)-sulfoximinyl)-5,5-dimethyl-4,5-dihydroisoxazole

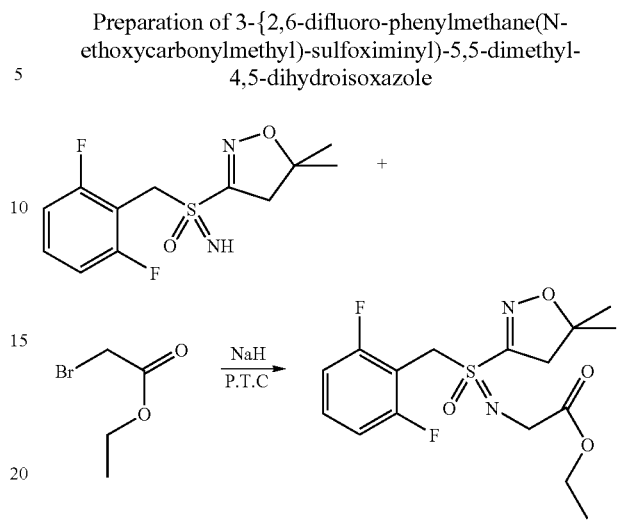

To a stirred suspension of sodium hydride (80% in mineral oil) (25 mg, 0.83 mmol) in dimethoxyethane (3 ml) was added 3-{2,6-difluoro-phenylmethanesulfoximinyl)-5,5-dimethyl-4,5-dihydroisoxazole (Compound No. 1.01 of Table 65) (200 mg, 0.69 mmol) as solution in dimethoxyethane (1.5 ml) at room temperature under nitrogen. After 5 min hexadecyl-tributyl phosphonium bromide (phase transfer catalyst, P.T.C.) (21 mg, 0.04 mmol) and ethyl bromoacetate (0.09 ml, 0.83 mmol) were added dropwise. After 2 h the mixture was poured into water (5 ml) and extracted several times with ethyl acetate. The combined organic phases were dried over MgSO$_4$ and concentrated. Purification by chromatography on silica gel (eluent: hexane/ethyl acetate) gave the product (Compound No. 1.18 of Table 65) as a yellow gum (103 mg, 40% yield).

TABLE 65

Compounds of formula Id (Id)

| Nr. | R | m | $R^5$ | $R^6$ | Q | n | M.p. [° C.] | $^1$H-NMR (400 MHz, CDCl$_3$) |
|---|---|---|---|---|---|---|---|---|
| 1.01 | 2,6-F | 1 | H | H | H | 1 | 89-91 | 1.45 (s, 3H, Me), 1.55 (s, 3H, Me), 2.9 (d, 1H, CH$_2$), 3.1 (d, 1H, CH$_2$), 3.28 (broad s, 1H, NH), 4.65 (d, 1H, CH$_2$), 4.80 (d, 1H, CH$_2$), 7.0 (m, 2H, CH), 7.4 (m, 1H, CH). |
| 1.02 | 2,6-F | 1 | Cl | H | H | 1 | 100 | 1:1 mixture of diastereomers: 1.42 (s, 3H, Me), 1.47 (s, 3H, Me), 1.52 (s, 3H, Me), 1.57 (s, 3H, Me), 2.95 (d, 1H, CH$_2$), 3.15 (d, 1H, CH$_2$), 3.2 (d, 1H, CH$_2$), 3.3 (d, 1H, CH$_2$), 3.53 (broad s, 1H, NH), 3.6 (broad s, 1H, NH), 6.42 (s, 1H, CHCl), 6.62 (s, 1H, CHCl), 7.02 (m, 4H, CH), 7.45 (m, 2H, CH). |

TABLE 65-continued

Compounds of formula Id (Id)

| Nr. | R | m | R⁵ | R⁶ | Q | n | M.p. [° C.] | ¹H-NMR (400 MHz, CDCl₃) |
|---|---|---|---|---|---|---|---|---|
| 1.03 | 2,6-F | 1 | H | H | —CO(4-ClPh) | 1 | 154-156 | 1.55 (s, 6H, Me), 3.15 (d, 1H, CH₂), 3.35 (d, 1H, CH₂), 5.0 (d, 1H, CH₂), 5.15 (d, 1H, CH₂), 7.02 (t, 2H, CH), 7.38 (d, 2H, CH), 7.45 (m, 1H, CH), 8.0 (d, 2H, CH). |
| 1.04 | 2,6-F | 1 | H | H | —COCF₃ | 1 | 143-144 | 1.55 (s, 6H, Me), 3.05 (d, 1H, CH₂), 3.25 (d, 1H, CH₂), 4.95 (d, 1H, CH₂), 5.2 (d, 1H, CH₂), 7.05 (m, 2H, CH), 7.5 (m, 1H, CH). |
| 1.05 | 2,6-F | 1 | Cl | H | —COCF₃ | 1 | | 1.60 (s, 6H, Me), 3.25 (d, 1H, CH₂), 3.45 (d, 1H, CH₂), 6.9 (m, 1H, CHCl), 7.05 (m, 2H, CH), 7.52 (m, 1H, CH). |
| 1.06 | 2,6-F | 1 | H | H | —(CO)OᵗBu | 1 | | 1.48-1.52 (m, 15H, Me), 3.0 (d, 1H, CH₂), 3.1 (d, 1H, CH₂), 4.8 (d, 1H, CH₂), 5.0 (d, 1H, CH₂), 7.0 (m, 2H, CH), 7.4 (m, 1H, CH). |
| 1.07 | 2,6-F | 1 | H | H | —COCH₃ | 1 | | 1.45 (s, 3H, Me), 1.55 (s, 3H, Me), 2.2 (s, 3H, Me), 3.05 (d, 1H, CH₂), 3.25 (d, 1H, CH₂), 4.85 (d, 1H, CH₂), 5.05 (d, 1H, CH₂), 7.0 (m, 2H, CH), 7.4 (m, 1H, CH). |
| 1.08 | 2,6-F | 1 | H | H | —CH₃ | 1 | | 1.45 (s, 3H, Me), 1.55 (s, 3H, Me), 2.85 (s, 3H, Me), 2.85 (d, 1H, CH₂), 3.05 (d, 1H, CH₂), 4.55 (d, 1H, CH₂), 4.75 (d, 1H, CH₂), 7.0 (m, 2H, CH), 7.4 (m, 1H, CH). |
| 1.09 | 2,6-F | 0 | H | H | —COCF₃ | 1 | | 1.5 (s, 6H, Me), 3.0 (d, 1H, CH₂), 3.2 (d, 1H, CH₂), 4.65 (d, 1H, CH₂), 4.85 (d, 1H, CH₂), 7.0 (m, 2H, CH), 7.45 (m, 1H, CH). |
| 1.10 | 2,6-F | 1 | H | H | —Si(CH₃)₃ | 1 | | 0.8 (s, 9H, Me), 1.5 (s, 6H, Me), 3.0 (d, 1H, CH₂), 3.1 (d, 1H, CH₂), 4.65 (s, 2H, CH₂), 7.0 (m, 2H, CH), 7.4 (m, 1H, CH). |
| 1.11 | 2,6-F | 1 | H | H | —SO₂(4-NO₂Ph) | 1 | | 1.55 (s, 6H, Me), 3.25 (d, 1H, CH₂), 3.35 (d, 1H, CH₂), 4.95 (d, 1H, CH₂), 5.1 (d, 1H, CH₂), 7.05 (m, 2H, CH), 7.5 (m, 1H, CH), 8.15 (m, 2H, CH), 8.35 (m, 2H, CH). |
| 1.12 | 2,6-F | 1 | H | H | —SO₂Me | 1 | | 1.50 (s, 3H, Me), 1.6 (s, 3H, Me), 3.1 (s, 3H, Me), 3.1 (d, 1H, CH₂), 3.3 (d, 1H, CH₂), 4.9 (d, 1H, CH₂), 5.0 (d, 1H, CH₂), 7.0 (m, 2H, CH), 7.45 (m, 1H, CH). |
| 1.13 | 2,6-F | 1 | H | H | —CHO | 1 | | 1.50 (s, 6H, Me), 3.1 (d, 1H, CH₂), 3.25 (d, 1H, CH₂), 5.0 (d, 1H, CH₂), 5.1 (d, 1H, CH₂), 7.02 (m, 2H, CH), 7.45 (m, 1H, CH), 8.4 (s, 1H, CHO). |

TABLE 65-continued

Compounds of formula Id

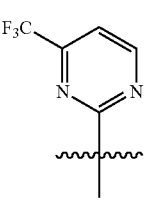

(Id)

| Nr. | R | m | $R^5$ | $R^6$ | Q | n | M.p. [° C.] | $^1$H-NMR (400 MHz, CDCl$_3$) |
|---|---|---|---|---|---|---|---|---|
| 1.14 | 2,6-F | 1 | H | H | —SO$_2$CF$_3$ | 1 | 108 | 1.57 (s, 3H, Me), 1.59 (s, 3H, Me), 3.15 (d, 1H, CH$_2$), 3.25 (d, 1H, CH$_2$), 5.05 (d, 1H, CH$_2$), 5.15 (d, 1H, CH$_2$), 7.05 (m, 2H, CH), 7.5 (m, 1H, CH). |
| 1.15 | 2,6-F | 1 | H | H | —NO$_2$ | 1 |  | 1.5 (s, 3H, Me), 1.6 (s, 3H, Me), 3.1 (d, 1H, CH$_2$), 3.3 (d, 1H, CH$_2$), 5.05 (s, 2H, CH$_2$), 7.05 (m, 2H, CH), 7.5 (m, 1H, CH). |
| 1.16 | 2,6-F | 1 | H | H | (4-CF$_3$-pyrimidin-2-yl) | 1 |  | 1.45 (s, 3H, Me), 1.5 (s, 3H, Me), 2.95 (d, 1H, CH$_2$), 3.3 (d, 1H, CH$_2$), 5.1 (d, 1H, CH$_2$), 5.18 (d, 1H, CH$_2$), 7.0 (m, 2H, CH), 7.2 (d, 1H, CH), 7.4-7.5 (m, 1H, CH), 8.7 (d, 1H, CH). |
| 1.17 | 2,6-F | 1 | H | H | —(CO)OCH$_2$ClCH$_3$ | 1 |  | 1:1 mixture of diastereoisomers: 1.5 (s, 6H, Me), 1.52 (s, 3H, Me), 1.55 (s, 3H, Me), 1.7 (s, 3H, Me), 1.75 (s, 3H, Me), 3.0 (d, 1H, CH$_2$), 3.03 (d, 1H, CH$_2$), 3.18 (d, 1H, CH$_2$), 3.2 (d, 1H, CH$_2$), 4.95 (d, 1H, CH$_2$), 5.0 (d, 1H, CH$_2$), 5.05 (d, 1H, CH$_2$), 5.1 (d, 1H, CH$_2$), 6.5 (q, 2H, CH), 7.0-7.1 (m, 4H, CH), 7.4-7.5 (m, 2H, CH). |
| 1.18 | 2,6-F | 1 | H | H | —CH$_2$(CO)OCH$_2$CH$_3$ | 1 |  | 1.25 (t, 3H, Me), 1.48 (s, 3H, Me), 1.5 (s, 3H, Me), 2.95 (d, 1H, CH$_2$), 3.1 (d, 1H, CH$_2$), 3.95 (s, 2H, CH$_2$), 4.2 (q, 2H, CH$_2$), 4.75 (d, 1H, CH$_2$), 4.8 (d, 1H, CH$_2$), 6.95-7.0 (m, 2H, CH), 7.35-7.4 (m, 1H, CH). |
| 1.19 | 2,6-F | 1 | H | —CH$_3$ | —COCF$_3$ | 1 |  | Diastereomer A: 1.54 (s, 3H, Me), 1.57 (s, 3H, Me), 2.02 (d, 3H, Me), 3.06 (d, 1H, CH$_2$), 3.31 (d, 1H, CH$_2$), 5.43 (q, 1H, CHMe), 7.00 (m, 2H, CH), 7.43 (m, 1H, CH). |
| 1.20 | 2,6-F | 1 | H | —CH$_3$ | —COCF$_3$ | 1 |  | Diastereomer B: 1.36 (s, 3H, Me), 1.48 (s, 3H, Me), 2.02 (d, 3H, Me), 2.67 (d, 1H, CH$_2$), 3.12 (d, 1H, CH$_2$), 5.35 (q, 1H, CHMe), 7.00 (m, 2H, CH), 7.43 (m, 1H, CH). |

TABLE 65-continued

Compounds of formula Id (Id)

[Structure: 5,5-dimethyl-4,5-dihydroisoxazol-3-yl group connected to S(=N-Q)(=O)$_m$-[CR$^5$R$^6$]$_n$-phenyl-R]

| Nr. | R | m | R$^5$ | R$^6$ | Q | n | M.p. [°C.] | $^1$H-NMR (400 MHz, CDCl$_3$) |
|---|---|---|---|---|---|---|---|---|
| 1.21 | 2,6-F | 1 | H | H | [3-carbonyl-2-chloropyridin-3-yl] | 1 | | 1.55 (s, 3H, Me), 1.57 (s, 3H, Me), 3.15 (d, 1H, CH$_2$), 3.35 (d, 1H, CH$_2$), 5.05 (d, 1H, CH$_2$), 5.2 (d, 1H, CH$_2$), 7.0-7.05 (m, 2H, CH), 7.3 (dd, 1H, CH), 7.4-7.5 (m, 1H, CH), 8.2 (dd, 1H, CH), 8.45 (dd, 1H, CH). |
| 1.22 | 2,6-F | 1 | F | F | H | 1 | 112 | 1.52 (s, 3H, Me), 1.55 (s, 3H, Me), 3.15 (d, 1H, CH$_2$), 3.26 (d, 1H, CH$_2$), 3.6 (broad s, 1H, NH) 7.05 (t, 2H, CH), 7.5-7.6 (m, 1H, CH). |
| 1.23 | 2,6-F | 1 | H | H | [5-cyanopyrimidin-4-yl] | 1 | | 1.48 (s, 3H, Me), 1.52 (s, 3H, Me), 3.1 (d, 1H, CH$_2$), 3.2 (d, 1H, CH$_2$), 5.1 (d, 1H, CH$_2$), 5.15 (d, 1H, CH$_2$), 7.0-7.05 (m, 2H, CH), 7.4-7.5 (m, 1H, CH), 8.2 (d, 1H, CH), 8.25 (d, 1H, CH). |
| 1.24 | 2-OCF$_3$ | 1 | H | H | H | 1 | | 1.4 (s, 3H, Me), 1.45 (s, 3H, Me), 2.9 (d, 1H, CH$_2$), 3.0 (d, 1H, CH$_2$), 2.9-3.1 (broad s, 1H, NH), 4.7 (d, 1H, CH$_2$), 4.78 (d, 1H, CH$_2$), 7.3-7.4 (m, 2H, CH), 7.4-7.5 (m, 1H, CH), 7.5-7.6 (m, 1H, CH). |
| 1.25 | 2-OCHF$_2$ | 1 | H | H | H | 1 | | 1.4 (s, 6H, Me), 2.9 (d, 1H, CH$_2$), 3.05 (d, 1H, CH$_2$), 4.72 (d, 1H, CH$_2$), 4.8 (d, 1H, CH$_2$), 6.6 (t, 1H, CH), 7.2-7.3 (m; 2H, CH), 7.4-7.45 (m, 1H, CH), 7.55-7.6 (m, 1H, CH). |
| 1.26 | 2-SCF$_3$ | 1 | H | H | H | 1 | | 1.4 (s, 3H, Me), 1.45 (s, 3H, Me), 2.9 (d, 1H, CH$_2$), 3.05 (d, 1H, CH$_2$), 5.0 (d, 1H, CH$_2$), 5.08 (d, 1H, CH$_2$), 7.5-7.6 (m, 2H, CH), 7.65 (d, 1H, CH), 7.85 (d, 1H, CH). |
| 1.27 | 2-CH$_3$ | 1 | H | H | H | 1 | | 1.4 (s, 3H, Me), 1.45 (s, 3H, Me), 2.5 (s, 3H, Me), 2.65 (d, 1H, CH$_2$), 2.95 (d, 1H, CH$_2$), 4.7 (d, 1H, CH$_2$), 4.85 (d, 1H, CH$_2$), 7.2-7.35 (m, 3H, CH), 7.4 (d, 1H, CH). |
| 1.28 | 2,6-F, 3-CH$_3$ | 1 | H | H | H | 1 | | 1.5 (s, 3H, Me), 1.51 (s, 3H, Me), 2.25 (s, 3H, Me), 3.0 (d, 1H, CH$_2$), 3.08 (d, 1H, CH$_2$), 4.7 (d, 1H, CH$_2$), 4.75 (d, 1H, CH$_2$), 6.9 (m, 1H, CH), 7.2-7.3 (m, 1H, CH). |
| 1.29 | 2,3-F | 1 | H | H | H | 1 | | 1.48 (s, 3H, Me), 1.5 (s, 3H, Me), 2.95 (d, 1H, CH$_2$), 3.05 (d, 1H, CH$_2$), 2.9-3.1 (broad s, 1H, NH), 4.7 (d, |

TABLE 65-continued

Compounds of formula Id (Id)

| Nr. | R | m | R⁵ | R⁶ | Q | n | M.p. [°C.] | ¹H-NMR (400 MHz, CDCl₃) |
|---|---|---|---|---|---|---|---|---|
| | | | | | | | | 1H, CH₂), 4.75 (d, 1H, CH₂), 7.1-7.3 (m, 3H, CH). |
| 1.30 | 2,4-F | 1 | H | H | H | 1 | | 1.48 (s, 3H, Me), 1.5 (s, 3H, Me), 2.95 (d, 1H, CH₂), 3.05 (d, 1H, CH₂), 4.65 (d, 1H, CH₂), 4.7 (d, 1H, CH₂), 6.9-7.0 (m, 2H, CH), 7.5-7.55 (m, 1H, CH). |
| 1.31 | 2-CF₃ | 1 | H | H | H | 1 | | 1.4 (s, 3H, Me), 1.45 (s, 3H, Me), 2.9 (d, 1H, CH₂), 3.05 (d, 1H, CH₂), 3.4-3.7 (broad s, 1H, NH), 4.9 (d, 1H, CH₂), 4.95 (d, 1H, CH₂), 7.55 (t, 1H, CH), 7.65 (t, 1H, CH), 7.75 (d, 1H, CH), 7.85 (d, 1H, CH). |
| 1.32 | 2-F, 6-CF₃ | 1 | H | H | H | 1 | | 1.55 (s, 6H, Me), 3.1 (d, 1H, CH₂), 3.15 (d, 1H, CH₂), 5.05 (d, 1H, CH₂), 5.08 (d, 1H, CH₂), 7.35-7.4 (m, 1H, CH), 7.5-7.6 (m, 2H, CH). |
| 1.33 | 2-Ph | 1 | H | H | H | 1 | | 1.4 (s, 3H, Me), 1.41 (s, 3H, Me), 2.7 (d, 1H, CH₂), 2.85 (d, 1H, CH₂), 3.1-3.3 (broad s, 1H, NH), 4.7 (d, 1H, CH₂), 4.8 (d, 1H, CH₂), 7.35-7.5 (m, 8H, CH), 7.7 (d, 1H, CH). |
| 1.34 | 2,5-F | 1 | H | H | H | 1 | | 1.48 (s, 3H, Me), 1.49 (s, 3H, Me), 2.95 (d, 1H, CH₂), 3.05 (d, 1H, CH₂), 4.65 (s, 2H, CH₂), 7.1-7.15 (m, 2H, CH), 7.2-7.3 (m, 1H, CH). |
| 1.35 | 2,6-F | 1 | H | F | —COPh | 1 | 128 | 1.6 (s, 6H, Me) 3.3 (d, 1H, CH₂), 3.6 (d, 1H, CH₂), 7.05-7.1 (m, 2H, CH), 7.25 (d, 1H, CH), 7.35-7.40 (m, 2H, CH), 7.5-7.6 (m, 2H, CH), 8.0 (d, 2H, CH). |
| 1.36 | 2,6-F | 1 | H | H | —COPh | 1 | 141 | 1.53 (s, 3H, Me), 1.54 (s, 3H, Me), 3.15 (d, 1H, CH₂), 3.4 (d, 1H, CH₂), 5.0 (d, 1H, CH₂), 5.15 (d, 1H, CH₂), 7.0-7.05 (m, 2H, CH), 7.35-7.45 (m, 3H, CH), 7.5-7.53 (m, 1H, CH), 8.1 (d, 2H, CH). |
| 1.37 | 2,6-F | 1 | F | F | —COPh | 1 | | 1.55 (s, 6H, Me), 3.2 (d, 1H, CH₂), 3.32 (d, 1H, CH₂), 7.05-7.1 (m, 2H, CH), 7.38-7.42 (m, 2H, CH), 7.5-7.55 (m, 1H, CH), 7.55-7.65 (m, 1H, CH), 8.03 (d, 2H, CH). |
| 1.38 | 2,6-F | 1 | F | F | —CO(4-NO₂Ph) | 1 | 159 | 1.6 (s, 6H, Me), 3.2 (d, 1H, CH₂), 3.39 (d, 1H, CH₂), 7.1-7.15 (m, 2H, CH), 7.6-7.7 (m, 1H, CH), 8.2 (d, 2H, CH), 8.25 (d, 2H, CH). |
| 1.39 | 2-F | 1 | H | H | H | 1 | | 1.38 (s, 3H, Me), 1.42 (s, 3H, Me), 2.85 (d, 1H, CH₂), 3.1 (d, 1H, CH₂), 4.95 (d, 1H, CH₂), 5.0 (d, 1H, CH₂), |

TABLE 65-continued

Compounds of formula Id (Id)

| Nr. | R | m | $R^5$ | $R^6$ | Q | n | M.p. [° C.] | $^1$H-NMR (400 MHz, CDCl$_3$) |
|---|---|---|---|---|---|---|---|---|
| 1.40 | 3,5-F | 1 | H | H | H | 1 | | 7.08-7.2 (m, 2H, CH), 7.38-7.43 (m, 2H, CH). 1.43 (s, 3H, Me), 1.48 (s, 3H, Me), 2.7-2.9 (broad s, 1H, NH), 2.85 (d, 1H, CH$_2$), 3.0 (d, 1H, CH$_2$), 4.55 (d, 1H, CH$_2$), 4.65 (d, 1H, CH$_2$), 6.85-6.9 (m, 1H, CH), 6.97-7.02 (m, 2H, CH). |
| 1.41 | 2-CN | 1 | H | H | H | 1 | 127 | 1.48 (s, 6H, Me), 3.1 (s, 2H, CH$_2$), 3.05-3.2 (broad s, 1H, NH), 4.85 (s, 2H, CH$_2$), 7.5-7.55 (m, 1H, CH), 7.65-7.7 (m, 1H, CH), 7.7-7.75 (m, 2H, CH). |
| 1.42 | H | 1 | H | H | H | 1 | 87 | 1.45 (s, 3H,Me), 1.53 (s, 3H, Me), 2.62 (d, 1H, CH$_2$), 2.9 (d, 1H, CH$_2$), 3.1-3.18 (broad s, 1H, NH), 4.55 (d, 1H, CH$_2$), 4.68 (d, 1H, CH$_2$), 7.4-7.5 (m, 5H, CH). |
| 1.43 | 2,6-F | 1 | H | F | —CO(4-ClPh) | 1 | 159 | 1.6 (s, 6H, Me), 3.3 (d, 1H, CH$_2$), 3.57 (d, 1H, CH$_2$), 7.05-7.1 (m, 2H, CH), 7.2 (d, 1H, CH), 7.35 (d, 2H, CH), 7.5-7.6 (m, 1H, CH), 7.9 (d, 2H, CH). |
| 1.44 | 2,6-F | 1 | F | F | —CO(4-ClPh) | 1 | | 1.6 (s, 6H, Me), 3.2 (d, 1H, CH$_2$), 3.5 (d, 1H, CH$_2$), 7.1 (t, 2H, CH), 7.38 (d, 2H, CH), 7.58-7.65 (m, 1H, CH), 7.95 (d, 2H, CH). |
| 1.45 | 2,6-F | 1 | H | H | —CO(4-NO$_2$Ph) | 1 | 164 | 1.55 (s, 6H, Me), 3.15 (d, 1H, CH$_2$), 3.4 (d, 1H, CH$_2$), 5.0 (d, 1H, CH$_2$), 5.15 (d, 1H, CH$_2$), 7.0-7.05 (m, 2H, CH), 7.4-7.5 (m, 1H, CH), 8.23 (s, 4H, CH). |
| 1.46 | 2-F,4-(CO)OCH$_3$ | 1 | H | H | H | 1 | | 1.45 (s, 6H, Me), 2.8-3.0 (broad s, 1H, NH), 2.95 (d, 1H, CH$_2$), 3.05 (d, 1H, CH$_2$), 3.95 (s, 3H, Me), 4.73 (s, 2H, CH$_2$), 7.6 (t, 1H, CH), 7.8 (d, 1H, CH), 7.9 (d, 1H, CH). |
| 1.47 | 2-F,4-(CO)OC$_2$H$_5$ | 1 | H | H | H | 1 | 125 | 1.4 (t, 3H, Me), 1.48 (s, 6H, Me), 2.6-2.9 (broad s, 1H, NH), 2.95 (d, 1H, CH$_2$), 3.05 (d, 1H, CH$_2$), 4.4 (q, 2H, CH$_2$), 4.72 (s, 2H, CH$_2$), 7.6 (t, 1H, CH), 7.8 (d, 1H, CH), 7.9 (d, 1H, CH). |
| 1.48 | 2,3-OCH$_2$OCH$_2$-, 5-F | 1 | H | H | H | 1 | 126 | 1.45 (s, 6H, Me), 2.95 (d, 1H, CH$_2$), 3.05 (d, 1H, CH$_2$), 3.2-3.4 (broad s, 1H, NH), 4.63 (d, 1H, CH$_2$), 4.68 (d, 1H, CH$_2$), 4.88 (s, 2H, CH$_2$), 5.25 (s, 2H, CH$_2$), 6.75 (dd, 1H, CH), 7.1 (dd, 1H, CH). |
| 1.49 | 2,3-OCH$_2$ | 1 | H | H | —COCF$_3$ | 1 | | 1.5 (s, 3H, Me), 1.51 (s, 3H, Me), 2.95 (d, 1H, CH$_2$), |

TABLE 65-continued

Compounds of formula Id (Id)

| Nr. | R | m | R⁵ | R⁶ | Q | n | M.p. [° C.] | ¹H-NMR (400 MHz, CDCl₃) |
|---|---|---|---|---|---|---|---|---|
| | OCH₂-, 5-F | | | | | | | 3.18 (d, 1H, CH₂), 4.9 (s, 2H, CH₂), 5.0 (s, 2H, CH₂), 5.32 (d, 1H, CH₂), 5.37 (d, 1H, CH₂), 6.82 (dd, 1H, CH), 7.05 (dd, 1H, CH). |
| 1.50 | 2,6-F | 1 | H | F | —CO(4-NO₂Ph) | 1 | | Diastereomer A: 1.6 (s, 6H, Me), 3.32 (d, 1H, CH₂), 3.6 (d, 1H, CH₂), 7.1-7.15 (m, 2H, CH), 7.2 (d, 1H, CH), 7.55-7.65 (m, 1H, CH), 8.12 (d, 2H, CH), 8.33 (d, 2H, CH). |
| 1.51 | 2,6-F | 1 | H | F | —CO(4-NO₂Ph) | 1 | | Diastereomer B: 1.48 (s, 3H, Me), 1.52 (s, 3H, Me), 3.15 (d, 1H, CH₂), 3.3 (d, 1H, CH₂), 6.85 (d, 1H, CH), 6.95-7.05 (m, 2H, CH), 7.45-7.5 (m, 1H, CH), 8.13 (d, 2H, CH), 8.17 (d, 2H, CH). |
| 1.52 | 2,6-F | 1 | H | F | H | 1 | | Diastereomer A: 1.55 (s, 6H, Me) 3.22 (d, 1H, CH₂), 3.3 (d, 1H, CH₂), 3.4 (broad s, 1H, NH), 6.9 (d, 1H, CH), 7.0-7.1 (m, 2H, CH), 7.45-7.55 (m, 1H, CH). |
| 1.53 | 2,6-F | 1 | H | F | H | 1 | | Diastereomer B: 1.55 (s, 6H, Me) 3.15 (d, 1H, CH₂), 3.22 (d, 1H, CH₂), 3.4 (broad s, 1H, NH), 6.65 (d, 1H, CH), 7.0-7.05 (m, 2H, CH), 7.45-7.55 (m, 1H, CH). |
| 1.54 | 2,6-F | 1 | Cl | F | H | 1 | | Diastereomer A: 1.5 (s, 3H, Me), 1.55 (s, 3H, Me), 3.2 (d, 1H, CH₂), 3.28 (d, 1H, CH₂), 3.85 (broad s, 1H, NH), 7.0 (t, 2H, CH), 7.45-7.52 (m, 1H, CH). |
| 1.55 | 2,6-F | 1 | Cl | F | H | 1 | | Diastereomer B: 1.5 (s, 3H, Me), 1.52 (s, 3H, Me), 3.02 (d, 1H, CH₂), 3.25 (d, 1H, CH₂), 3.65 (broad s, 1H, NH), 7.05 (t, 2H, CH), 7.45-7.55 (m, 1H, CH). |
| 1.56 | 2-OCF₃ | 1 | H | F | H | 1 | | 4:1 mixture of diastereomers (not separated) major isomer: 1.5 (s, 3H, Me), 1.55 (s, 3H, Me), 3.1 (d, 1H, CH₂), 3.12 (d, 1H, CH₂), 3.2-3.3 (broad s, 1H, NH), 6.7 (d, 1H, CH), 7.38-7.45 (m, 2H, CH), 7.6 (t, 1H, CH), 7.8 (d, 1H, CH). minor isomer: 1.5 (s, 3H, Me), 1.55 (s, 3H, Me), 3.2-3.3 (m, 3H, CH₂ & NH), 6.9 (d, 1H, CH), 7.38-7.45 (m, 2H, CH), 7.6 (t, 1H, CH), 7.65 (d, 1H, CH). |
| 1.57 | 2-OCF₃ | 1 | F | F | H | 1 | | 1.52 (s, 3H, Me), 1.55 (s, 3H, Me), 3.15 (d, 1H, CH₂), 3.28 (d, 1H, CH₂), 3.5 (broad s, 1H, NH), 7.45- |

TABLE 65-continued

Compounds of formula Id (Id)

| Nr. | R | m | $R^5$ | $R^6$ | Q | n | M.p. [° C.] | $^1$H-NMR (400 MHz, CDCl$_3$) |
|---|---|---|---|---|---|---|---|---|
| 1.58 | 2-Cl, 3-(CO)OC$_2$H$_5$, 6-SO$_2$CH$_3$ | 1 | H | H | —COCF$_3$ | 1 |  | 7.52 (m, 2H, CH), 7.67-7.72 (m, 1H, CH), 7.75 (d, 1H, CH), 1.43 (t, 3H, Me), 1.51 (s, 3H, Me), 1.55 (s, 3H, Me), 3.08 (d, 1H, CH$_2$), 3.23 (d, 1H, CH$_2$), 3.38 (s, 3H, Me), 4.46 (q, 2H, CH$_2$), 5.22 (d, 1H, CH$_2$), 6.01 (d, 1H, CH$_2$), 7.95 (d, 1H, CH), 8.15 (d, 1H, CH). |
| 1.59 | 2-Cl,3-(CO)OC$_2$H$_5$, 6-SO$_2$CH$_3$ | 1 | H | H | H | 1 | 44-47 | 1.41 (t, 3H, Me), 1.54 (s, 6H, Me), 3.17 (s, 2H, CH$_2$), 3.38 (s, 3H, Me), 4.45 (q, 2H, CH$_2$), 5.80 (broad s, 2H, CH$_2$), 7.86 (d, 1H, CH), 8.14 (d, 1H, CH). |

Key:
Me = methyl;
s = singlet;
m = multiplet;
d = doublet;
dd = double doublet;
t = triplet;
q = quartet.

TABLE 66

Compounds of formula Ie (Ie)

| Nr. | m | $R^5$ | $R^6$ | Q | $R^{17}$ | $R^{18}$ | $R^{19}$ | n | M.p. [° C.] | $^1$H-NMR (400 MHz, CDCl$_3$) |
|---|---|---|---|---|---|---|---|---|---|---|
| 2.01 | 1 | H | H | H | CH$_3$ | CF$_3$ | Cl | 1 | 101-103 | 1.50 (s, 6H, Me), 2.3 (broad s, 1H, NH), 3.0 (d, 1H, CH$_2$), 3.2 (d, 1H, CH$_2$), 3.8 (s, 3H, Me), 4.60 (d, 1H, CH$_2$), 4.7 (d, 1H, CH$_2$). |
| 2.02 | 1 | H | H | —COCF$_3$ | CH$_3$ | CF$_3$ | Cl | 1 |  | 1.55 (s, 6H, Me), 3.15 (d, 1H, CH$_2$), 3.35 (d, 1H, CH$_2$), 3.94 (s, 3H, Me), 4.22 (s, 2H, CH$_2$). |
| 2.03 | 1 | F | F | H | CH$_3$ | CF$_3$ | Cl | 1 |  | 1.52 (s, 3H, Me), 1.54 (s, 3H, Me), 3.15 (d, 1H, CH$_2$), 3.25 (d, 1H, CH$_2$), 3.55 (broad s, 1H, NH), 3.97 (s, 3H, Me). |

TABLE 66-continued

Compounds of formula Ie $$\text{(Ie)}$$

Structure: N-Q, S(=N)(O)_m with H3C, H3C dimethyl isoxazoline, linked via [CR^5R^6]_n to pyrazole ring bearing R^18, R^19, R^17.

| Nr. | m | R^5 | R^6 | Q | R^17 | R^18 | R^19 | n | M.p. [° C.] | $^1$H-NMR (400 MHz, CDCl$_3$) |
|---|---|---|---|---|---|---|---|---|---|---|
| 2.04 | 1 | H | H | H | CH$_3$ | OCHF$_2$ | CF$_3$ | 1 | | 1.5 (s, 3H, Me), 1.5 (s, 3H, Me), 3.1 (d, 1H, CH$_2$), 3.1 (d, 1H, CH$_2$), 3.93 (s, 3H, Me), 4.55 (d, 1H, CH$_2$), 4.55 (d, 1H, CH$_2$), 6.9 (t, J=75 Hz, 1H, CH). |
| 2.05 | 1 | H | H | —COCF$_3$ | CH$_3$ | CF$_3$ | H | 1 | | 1.51 (s, 3H, Me), 1.52 (s, 3H, Me), 3.07 (d, 1H, CH$_2$), 3.30 (d, 1H, CH$_2$), 4.00 (s, 3H, Me), 4.94 (s, 2H, CH$_2$), 7.70 (s, 1H, CH). |
| 2.06 | 1 | H | H | H | CH$_3$ | CF$_3$ | H | 1 | | 1.44 (s, 3H, Me), 1.47 (s, 3H, Me), 2.98 (d, 1H, CH$_2$), 3.08 (d, 1H, CH$_2$), 3.97 (s, 3H, Me), 4.56 (d, 1H, CH$_2$), 4.62 (d, 1H, CH$_2$), 7.75 (s, 1H, CH). |
| 2.07 | 1 | H | H | H | CH$_3$ | CHF$_2$ | H | 1 | | 1.43 (s, 3H, Me), 1.46 (s, 3H, Me), 2.99 (d, 1H, CH$_2$), 3.08 (d, 1H, CH$_2$), 3.93 (s, 3H, Me), 4.59 (d, 1H, CH$_2$), 4.65 (d, 1H, CH$_2$), 6.76 (t, 1H, CH), 7.70 (s, 1H, CH). |
| 2.08 | 1 | H | H | —COCF$_3$ | CH$_3$ | CHF$_2$ | H | 1 | | 1.50 (s, 3H, Me), 1.51 (s, 3H, Me), 3.00 (d, 1H, CH$_2$), 3.28 (d, 1H, CH$_2$), 3.96 (s, 3H, Me), 4.96 (s, 2H, CH$_2$), 6.76 (t, 1H, CH), 7.70 (s, 1H, CH). |

Key:
Me = methyl;
s = singlet;
d = doublet;
t = triplet.

BIOLOGICAL EXAMPLES

Example B1

Herbicidal Action

Monocotyledonous and dicotyledonous test plants were sown in sterilised standard soil in seed trays each having 96 cells. After one day (pre-emergence) or after 8 to 9 days cultivation (post-emergence) under controlled conditions in a climatic chamber (cultivation at 17/23° C.; 13 hours light; 50-60% humidity; after application at 19/24° C.), the plants were treated with an aqueous spray solution of 1000 mg/l of the active ingredient used (including 10% DMSO as solvent). The plants were grown on in the climatic chamber until the test was evaluated (10=total damage to plant, 0=no damage to plant) after 9 or 13 days.

TABLE B1

| | Application pre-emergence | | | |
|---|---|---|---|---|
| Comp. No. | [g/ha] | Digitaria | Agrostis | Poa | Setaria |
| 1.01 | 1000 | 10 | 10 | 10 | 9 |
| 1.02 | 1000 | 10 | 10 | 10 | 10 |
| 1.03 | 1000 | 8 | 7 | 10 | 8 |
| 1.04 | 1000 | 10 | 10 | 10 | 10 |

TABLE B1-continued

Application pre-emergence

| Comp. No. | [g/ha] | Digitaria | Agrostis | Poa | Setaria |
|---|---|---|---|---|---|
| 1.05 | 1000 | 9 | 10 | 10 | 9 |
| 1.06 | 1000 | 7 | 9 | 6 | 10 |
| 1.07 | 1000 | 9 | 10 | 10 | 9 |
| 1.08 | 1000 | 7 | 10 | 10 | 9 |
| 1.13 | 1000 | 9 | 10 | 10 | 9 |
| 1.14 | 1000 | 7 | 10 | 10 | 0 |
| 1.15 | 1000 | 9 | 10 | 10 | 8 |
| 1.17 | 1000 | 8 | 10 | 10 | 8 |
| 1.19 | 1000 | 9 | 10 | 6 | 9 |
| 1.20 | 1000 | 8 | 9 | 4 | 8 |
| 1.21 | 1000 | 9 | 10 | 10 | 9 |
| 1.22 | 1000 | 10 | 10 | 10 | 10 |
| 1.24 | 1000 | 9 | 10 | 0 | 8 |
| 1.25 | 1000 | 9 | 10 | 10 | 8 |
| 1.27 | 1000 | 8 | 5 | 0 | 5 |
| 1.28 | 1000 | 9 | 10 | 10 | 8 |
| 1.29 | 1000 | 8 | 10 | 10 | 6 |
| 1.30 | 1000 | 10 | 10 | 10 | 8 |
| 1.31 | 1000 | 8 | 10 | 8 | 8 |
| 1.32 | 1000 | 10 | 10 | 10 | 9 |
| 1.34 | 1000 | 9 | 10 | 10 | 8 |
| 1.35 | 1000 | 8 | 10 | 10 | 8 |
| 1.36 | 1000 | 5 | 10 | 0 | 7 |
| 1.48 | 1000 | 8 | 0 | 0 | 8 |
| 1.56 | 1000 | 9 | 10 | 10 | 8 |
| 2.01 | 1000 | 10 | 10 | 10 | 10 |

Example E1

Pre-emergent Safening Test on Maize

The test plants were sown in seed trays under greenhouse conditions. A standard earth was used as the culture substrate. In a pre-emergent stage, the herbicides were applied both by themselves and in a mixture with safeners to the soil surface. The application was carried out with an aqueous suspension of the test substances, prepared from a 25% wettable powder (Example F3, b according to WO 97/34485) or from a suspension concentrate (Example F8 according to WO 97/34485), to achieve a field equivalent of 200 l/ha. The tests were evaluated after 14 days (100%=plants completely dead; 0%=no phytotoxic action on the plants).

TABLE E1

Safener action on pre-emergent use on maize (Marista)

| Comp. 1.01 WP 25% AW/W | | Comp. 1.01 WP 25% AW/W 400 200 [g/ha] Benoxacor WP 25% AW/W | | Comp. 1.01 WP 25% AW/W 400 200 [g/ha] Dichlormid EC 250 GA/L | | Comp. 1.01 WP 25% AW/W 400 200 [g/ha] Furilazole WP 5% AW/W | |
|---|---|---|---|---|---|---|---|
| 400 | 200 [g/ha] | 100 | 50 [g/ha] | 100 | 50 [g/ha] | 100 | 50 [g/ha] |
| 62.5 | 67.5 [%] | 55 | 0 [%] | 57.5 | 7.5 [%] | 25 | 2.5 [%] |

The invention claimed is:

1. A compound of formula (I)

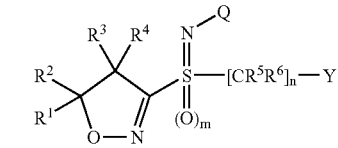

wherein
R$^1$ and R$^2$ are each independently of the other hydrogen, C$_1$-C$_{10}$alkyl, C$_1$-C$_{10}$haloalkyl, C$_3$-C$_8$cycloalkyl or C$_3$-C$_8$cycloalkyl-C$_1$-C$_3$alkyl, or
R$^1$ and R$^2$ together with the carbon atom to which they are bonded form a C$_3$-C$_7$ring,
R$^3$ and R$^4$ are each independently of the other hydrogen, C$_1$-C$_{10}$alkyl,
C$_1$-C$_{10}$haloalkyl, C$_3$-C$_8$cycloalkyl-C$_1$-C$_{10}$alkyl, C$_1$-C$_6$alkoxy-C$_1$-C$_{10}$alkyl or C$_3$-C$_8$cycloalkyl, or
R$^3$ and R$^4$ together with the carbon atom to which they are bonded form a C$_3$-C$_7$ring, or
R$^1$ with R$^3$ or R$^4$ and together with the carbon atoms to which they are bonded form a C$_5$-C$_8$ring, or
R$^2$ with R$^3$ or R$^4$ and together with the carbon atoms to which they are bonded form a C$_5$-C$_8$ring;
R$^5$ and R$^6$ are each independently of the other hydrogen, C$_1$-C$_6$alkyl, C$_3$-C$_6$cycloalkyl, 4,5-dihydropyrazole-CH$_2$—, C$_1$-C$_6$alkylcarbonyloxy-C$_2$-C$_6$alkenyl-, C$_3$-C$_6$cycloalkylcarbonyl, C$_1$-C$_6$alkoxy-C$_1$-C$_6$alkylcarbonyl, C$_1$-C$_6$alkoxycarbonyl, cyano, C$_1$-C$_6$haloalkyl, C$_1$-C$_6$hydroxyalkyl, pyrrolyl-CH$_2$—, pyrazolyl-CH$_2$—, triazolyl-CH$_2$—, imidazolyl-CH$_2$—, tetrazolyl-CH$_2$—, indolyl-CH$_2$—, indazolyl-CH$_2$—, benzotriazolyl-CH$_2$—, C$_2$-C$_6$alkenyl, C$_2$-C$_6$alkynyl, C$_2$-C$_6$haloalkenyl, C$_2$-C$_6$alkenyloxy, C$_2$-C$_6$alkynyloxy, C$_1$-C$_6$alkylcarbonyl, C$_1$-C$_6$haloalkylcarbonyl, phenylcarbonyl or phenylcarbonyl substituted by one to three R$^9$, or
R$^5$ and R$^6$ are each independently of the other phenoxycarbonyl or phenoxycarbonyl substituted by one to three R$^9$, or
R$^5$ and R$^6$ are each independently of the other benzyloxycarbonyl or benzyloxycarbonyl substituted by one to three R$^9$, or
R$^5$ and R$^6$ are each independently of the other nitro, formyl, carboxyl, halogen, azido, thiocyanato, tri(C$_1$-C$_6$alkyl)

silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)(OC$_1$-$C_6$alkyl)$_2$, $C_1$-$C_2$alkyl-NO$_2$, mercapto, phenylthio or phenylthio substituted by one to three $R^9$, or $R^5$ and $R^6$ are each independently of the other pyridylthio, $C_1$-$C_6$alkylthio, $C_1$-$C_6$haloalkylthio, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkylsulfonyl-$C_1$-$C_6$alkyl, $C_1$-$C_6$alkylsulphonyloxy-$C_1$-$C_6$alkyl, benzylsulfonyl or benzylsulfonyl substituted by one to three $R^9$, or $R^5$ and $R^6$ are each independently of the other phenylsulfinyl or phenylsulfinyl substituted by one to three $R^9$, or $R^5$ and $R^6$ are each independently of the other phenylsulfonyl or phenylsulfonyl substituted by one to three $R^9$, or $R^5$ and $R^6$ are each independently of the other hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, or $R^5$ and $R^6$ are each independently of the other benzyl or benzyl substituted by one to three $R^9$, or $R^5$ and $R^6$ are each independently of the other benzyloxy or benzyloxy substituted by one to three $R^9$, or $R^5$ and $R^6$ are each independently of the other —CONH—SO$_2$—$C_1$-$C_6$alkyl, —CONH—SO$_2$—$C_1$-$C_6$haloalkyl, —NHCHO, —NHCO—$C_1$-$C_6$alkyl, —NHCO—$C_1$-$C_6$haloalkyl, —NHCOO—$C_1$-$C_6$alkyl, —NHCONH—$C_1$-$C_6$alkyl, —NHCONH—$C_1$-$C_6$haloalkyl, —NHSO$_2$—$C_1$-$C_6$alkyl, —NHSO$_2$—$C_1$-$C_6$haloalkyl, —NHSO$_2$-phenyl or —NHSO$_2$-phenyl substituted by one to three $R^9$, or $R^5$ and $R^6$ are each independently of the other —OCO—$C_1$-$C_6$alkyl, —OCO—$C_1$-$C_6$haloalkyl, —OCO-phenyl or —OCO-phenyl substituted by one to three $R^9$, or $R^5$ and $R^6$ are each independently of the other —OCONH—$C_1$-$C_6$alkyl, —OCONH—$C_1$-$C_6$haloalkyl, —OCONH-phenyl or —OCONH-phenyl substituted by one to three $R^9$, or $R^5$ and $R^6$ are each independently of the other —CONR$^7$R$^8$ wherein $R^7$ and $R^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or $R^5$ and $R^6$ are each independently of the other phenyl or naphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, nitro, cyano, formyl, carboxyl, halogen, azido, thiocyanato, tri($C_1$-$C_6$alkyl)silyl, mercapto, phenylthio or phenylthio substituted by one to three $R^9$, phenylsulfinyl or phenylsulfinyl substituted by one to three $R^9$, —SF$_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH$_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or $R^5$ and $R^6$ are each independently of the other a 5- to 10-membered heterocycle containing one to three nitrogen, oxygen or sulfur atoms, which is optionally benzofused, and which is optionally substituted by one to three substituents independently selected from $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by, one to three $R^9$, phenylthio or phenylthio substituted by one to three $R^9$, phenylsulfinyl car phenylsulfinyl substituted by one to three $R^9$, nitro, cyano, formyl, carboxyl, halogen, azido, thiocyanato, tri($C_1$-$C_6$alkyl)silyl, mercapto, —SF$_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, $R^5$ and $R^6$ together with the carbon atom to which they are bonded form a 3- to 10-membered ring which optionally contains one to three nitrogen, oxygen or sulfur atoms and which is optionally substituted by one to three substituents independently selected from $C_1$-$C_6$alkyl, $C_1$-$C_6$haloalkyl, $C_1$-$C_6$alkoxy, $C_1$-$C_6$alkoxycarbonyl, $C_1$-$C_6$alkylcarbonyl, $C_1$-$C_6$alkylsulfonyl, $C_1$-$C_6$haloalkylsulfonyl, $C_1$-$C_6$haloalkylcarbonyl, $C_1$-$C_6$alkenyl, halogen, cyano, nitro, phenyl or phenyl substituted by $C_1$-$C_6$haloalkyl, nitro, cyano or by halogen, phenylcarbonyl or phenylcarbonyl substituted by $C_1$-$C_6$haloalkyl, nitro, cyano or by halogen, or $R^5$ and $R^6$ together with the carbon atom to which they are bonded form a group of the formula C=$CH_2$, C=CH—$C_1$-$C_6$alkyl, C=C(halogen)$_2$, C=CH—N($C_1$-$C_6$alkyl)$_2$, C=CH—NH($C_1$-$C_6$alkyl) or C=CH—$C_1$-$C_6$alkoxy;

m is 0 or 1;

n is 0, 1 or 2;

Q is hydrogen, $C_1$-$C_6$alkyl, $C_3$-$C_6$cycloalkyl, $C_1$-$C_6$alkoxycarbonyl, tri($C_1$-$C_6$alkyl)-silylethyloxycarbonyl, $C_1$-$C_6$haloalkoxycarbonyl, cyano, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by one to three $R^9$, or Q is benzylcarbonyl or benzylcarbonyl substituted by one to three $R^9$, or Q is pyridylcarbonyl or pyridylcarbonyl substituted by one to three $R^9$, or Q is phenoxycarbonyl or phenoxycarbonyl substituted by one to three $R^9$, or Q is benzyloxycarbonyl or benzyloxycarbonyl substituted by one to three $R^9$, or Q is nitro, formyl, tri($C_1$-$C_6$alkyl)silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)—(O$C_1$-$C_6$alkyl)$_2$, $C_1$-$C_2$alkyl-$NO_2$, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkylsulfonyl-$C_1$-$C_6$alkyl, benzylsulfonyl or benzylsulfonyl substituted by one to three $R^9$, or Q is phenylsulfinyl or phenylsulfinyl substituted by one to three $R^9$, or Q is phenylsulfonyl or phenylsulfonyl substituted by one to three $R^9$, or Q is benzyl or benzyl substituted by one to three $R^9$, or Q is —CONH—$SO_2$—$C_1$-$C_6$alkyl or —CONH—$SO_2$—$C_1$-$C_6$haloalkyl, or Q is —CON$R^7R^8$ wherein $R^7$ and $R^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or Q is phenyl or naphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, nitro, cyano, formyl, carboxyl, halogen, azido, thiocyanato, tri($C_1$-$C_6$alkyl)silyl, mercapto, phenylthio or phenylthio substituted by one to three $R^9$, phenylsulfinyl or phenylsulfinyl substituted by one to three $R^9$, —$SF_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(N$CH_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CON$R^7R^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or Q is a 3- to 10-membered heterocycle containing one or more nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, phenylthio or phenylthio substituted by one to three $R^9$, phenylsulfinyl or phenylsulfinyl substituted by one to three $R^9$, nitro, cyano, formyl, carboxyl, halogen, azido, thiocyanato, tri($C_1$-$C_6$alkyl)silyl, mercapto, —$SF_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CON$R^7R^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups; and Y is hydrogen, $C_1$-$C_6$alkyl, $C_3$-$C_6$cycloalkyl, $C_1$-$C_6$haloalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, nitro, cyano, formyl, hydroxyl, carboxyl, halogen, azido, thiocyanato, tri($C_1$-$C_6$alkyl)silyl, $C_1$-$C_6$alkylthio, $C_1$-$C_6$alkylsulfinyl, $C_1$-$C_6$alkylsulfonyl, benzylsulfonyl or benzylsulfonyl substituted by one to three $R^9$, or Y is phenylsulfonyl or phenylsulfonyl substituted by one to three $R^9$, or Y is $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, or Y is benzyloxy or benzyloxy substituted by one to three $R^9$, or Y is —CONH—$SO_2$—$C_1$-$C_6$alkyl or —CONH—$SO_2$—$C_1$-$C_6$haloalkyl, or Y is phenyl, naphthyl or tetrahydronaphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, benzyloxycarbonyl, nitro, cyano, formyl, carboxyl, halogen, azido, thiocyanato, tri($C_1$-$C_6$alkyl)silyl, mercapto, phenylthio, phenylsulfinyl, —$SF_5$, $C_1$-$C_6$alkylthio, $C_1$-$C_6$haloalkylthio, $C_1$-$C_6$haloalkylsulfinyl, $C_1$-$C_6$haloalkylsulfonyl, $C_1$-$C_6$alkylsulfinyl, $C_1$-$C_6$alkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —$CONR^7R^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ form a $C_3$-$C_8$alkylene group which optionally contains one oxygen or sulfur atom or one to two amino or $C_1$-$C_6$alkylamino groups, or Y is a 5- to 10-membered heterocycle containing one to three nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, nitro, cyano, formyl, carboxyl, halogen, azido, thiocyanato, tri($C_1$-$C_6$alkyl)silyl, mercapto, —$SF_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —$CONR^7R^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups;

$R^9$ are independently of each other $C_1$-$C_6$haloalkyl, $C_1$-$C_6$alkoxycarbonyl, nitro, cyano, formyl, carboxyl or halogen;

and to N-oxides, salts and optical isomers of compounds of formula I.

2. A compound as claimed in claim 1 in which $R^1$, $R^2$, $R^3$, $R^4$ are each independently hydrogen, methyl, fluoromethyl, chloromethyl, difluoromethyl or trifluoromethyl.

3. A compound as claimed in claim 1 in which $R^1$ and $R^2$ are both methyl.

4. A compound as claimed in claim 1 in which $R^3$ and $R^4$ are both hydrogen.

5. A compound as claimed in claim 1 in which $R^5$ and $R^6$ are independently of each other hydrogen, fluoro, chloro, methyl, acetyl or methoxycarbonyl.

6. A compound as claimed in claim 1 in which $R^5$ and $R^6$ are independently of each, other halogen.

7. A compound as claimed in claim 1 in which $R^5$ and $R^6$ are selected from chlorine and fluorine.

8. A compound as claimed in claim 7 in which $R^5$ and $R^6$ are fluorine.

9. A compound as claimed in claim 1 in which Q is hydrogen, formyl or acetyl.

10. A compound as claimed in claim 5 in which Q is hydrogen.

11. A compound as claimed in claim 1 in which m is 1.

12. A compound as claimed in claim 1 in which n is 1.

13. A process for the preparation of a compound of formula I wherein $R^1$, $R^2$, $R^3$, $R^4$, $R^5$, $R^6$, Q and Y are as defined in claim 1, m is 1 and n is 1, wherein a compound of formula Ic,

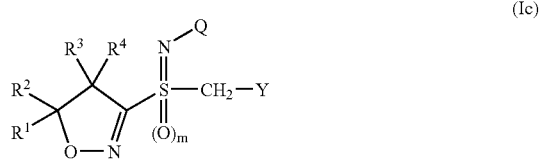

(Ic)

wherein $R^1$, $R^2$, $R^3$, $R^4$, Q and Y are as defined in claim 1 and m is 1, is reacted in an inert solvent in the presence of a base in a single step or stepwise in succession with compounds of formula $R^5$—$X^A$ and/or $R^6$—$X^A$, wherein $R^5$ and $R^6$ are as defined in claim 1 and $X^A$ is a leaving group.

14. A process according to claim 13 wherein $R^5$ and/or $R^6$ are halogen.

15. A process for the preparation of a compound of formula I wherein $R^1$, $R^2$, $R^3$, $R^4$, $R^5$, Q and Y are as defined in claim 1, $R^6$ is $C_1$-$C_{10}$alkyl or halogen, m is 1 and n is 1, wherein a compound of formula Id,

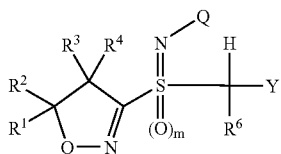

(Id)

wherein $R^1$, $R^2$, $R^3$, $R^4$, Q and Y are as defined in claim 1, $R^6$ is $C_1$-$C_{10}$alkyl or halogen and m is 1, is reacted in an inert solvent in the presence of a base with a compound of formula $R^5$—$X^A$, wherein $R^5$ is as defined in claim 1 and $X^A$ is a leaving group.

16. A process according to claim 15 wherein $R^5$ is halogen.

17. A process for the preparation of a compound of formula I wherein $R^1$, $R^2$, $R^3$, $R^4$, $R^5$, Q, n and Y are as defined in claim 1 and m is 0 or 1, wherein a compound of formula Ia,

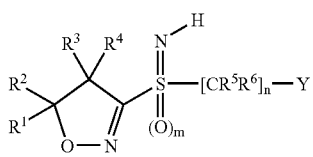

(Ia)

wherein $R^1$, $R^2$, $R^3$, $R^4$, $R^5$, $R^6$, n and Y are as defined in claim 1 and m is 0 or 1, is reacted in an inert solvent in the presence of a base with a compound of the formula Q-$X^A$, wherein Q is as defined in claim 1 and $X^A$ is a leaving group.

18. A process for the preparation of a compound of formula I wherein $R^1$, $R^2$, $R^3$, $R^4$, $R^5$, Q, n and Y are as defined in claim 1 and m is 1, wherein a compound of formula Ia,

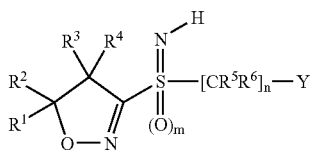

(Ia)

wherein $R^1$, $R^2$, $R^3$, $R^4$, $R^5$, $R^6$, n and Y are as defined in claim 1 and m is 1, is reacted in an inert solvent with a nitrating agent.

19. A process for the preparation of a compound of formula Ia wherein $R^1$, $R^2$, $R^3$, $R^4$, $R^5$, $R^6$, n and Y are as defined in claim 1 and m is 0 or 1, wherein a compound of formula Ib,

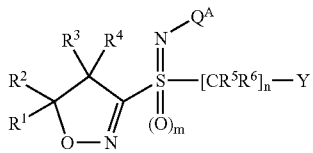

(Ib)

wherein $R^1$, $R^2$, $R^3$, $R^4$, $R^5$, $R^6$, n and Y are as defined in claim 1, m is 0 or 1 and $Q^A$ is an electron withdrawing group, is reacted in an inert solvent with either an acid, or a base, or a suitable nucleophile.

20. A process for the preparation of a compound of formula Ib wherein $R^1$, $R^2$, $R^3$, $R^4$, $R^5$, $R^6$, n and Y are as defined in claim 1 and m is 0 or 1, wherein a compound of formula II,

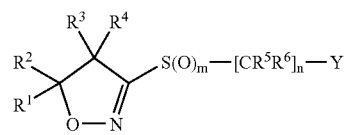

(II)

wherein $R^1$, $R^2$, $R^3$, $R^4$, $R^5$, $R^6$, n and Y are as defined in claim 1 and m is 0 or 1, is reacted in an inert solvent in the presence of a suitable transition metal catalyst, with an organic azide or with an imitation reagent of the formula ArI=$NQ^A$, wherein $Q^A$ is an electron withdrawing group and Ar is an optionally substituted phenyl.

21. A process for the preparation of a compound of formula I wherein $R^1$, $R^2$, $R^3$, $R^4$, $R^5$, $R^6$, Q, n and Y are as defined in claim 1 and m is 1, wherein a compound of formula I,

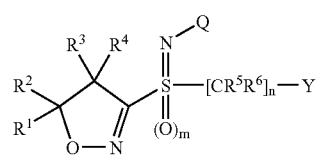

(I)

wherein $R^1$, $R^2$, $R^3$, $R^4$, $R^5$, $R^6$, Q, n and Y are as defined in claim 1 and m is 0, is reacted with an oxidant in an inert solvent.

22. A herbicidal composition which comprises a herbicidally effective amount of a compound of formula I in addition to formulation adjuvants.

23. A composition according to claim 22, which comprises a further herbicide in addition to the compound of formula I.

24. A composition according to claim 22, which comprises a safener in addition to the compound of formula I.

25. A method of controlling grasses and weeds in crops of useful plants, which comprises applying a herbicidally effective amount of a compound of formula I, or of a composition comprising such a compound, to the plants or to the locus thereof.

* * * * *